US012264190B2

(12) United States Patent
Moody et al.

(10) Patent No.: US 12,264,190 B2
(45) Date of Patent: Apr. 1, 2025

(54) COMPOSITIONS AND METHODS OF TREATING CANCER WITH CHIMERIC ANTIGEN RECEPTORS

(71) Applicant: ASTRAZENECA AB, Sodertalje (SE)

(72) Inventors: Gordon Moody, Gaithersburg, MD (US); Maria Letizia Giardino Torchia, Gaithersburg, MD (US); Michael Glen Overstreet, Gaithersburg, MD (US); Ryan Gilbreth, Gaithersburg, MD (US)

(73) Assignee: ASTRAZENECA AB, Sodertalje (SE)

( * ) Notice: Subject to any disclaimer, the term of this patent is extended or adjusted under 35 U.S.C. 154(b) by 83 days.

(21) Appl. No.: 17/237,498

(22) Filed: Apr. 22, 2021

(65) Prior Publication Data

US 2021/0332105 A1 Oct. 28, 2021

Related U.S. Application Data

(60) Provisional application No. 63/014,831, filed on Apr. 24, 2020.

(51) Int. Cl.

| | |
|---|---|
| ***C07K 14/725*** | (2006.01) |
| ***A61K 35/17*** | (2015.01) |
| ***A61K 38/17*** | (2006.01) |
| ***A61K 39/00*** | (2006.01) |
| ***A61K 39/395*** | (2006.01) |
| ***A61K 45/06*** | (2006.01) |
| ***A61P 35/00*** | (2006.01) |
| ***C07K 14/705*** | (2006.01) |
| ***C07K 14/71*** | (2006.01) |
| ***C07K 14/715*** | (2006.01) |
| ***C07K 16/28*** | (2006.01) |
| ***C07K 16/30*** | (2006.01) |
| ***C07K 16/32*** | (2006.01) |
| ***C12N 5/0783*** | (2010.01) |

(52) U.S. Cl.

CPC .............. *C07K 14/71* (2013.01); *A61K 35/17* (2013.01); *A61K 38/177* (2013.01); *A61K 38/1774* (2013.01); *A61K 38/179* (2013.01); *A61K 39/3955* (2013.01); *A61K 39/4611* (2023.05); *A61K 39/4613* (2023.05); *A61K 39/4631* (2023.05); *A61K 39/464474* (2023.05); *A61K 45/06* (2013.01); *A61P 35/00* (2018.01); *C07K 14/7051* (2013.01); *C07K 14/70521* (2013.01); *C07K 14/7056* (2013.01); *C07K 14/70578* (2013.01); *C07K 14/7151* (2013.01); *C07K 14/7153* (2013.01); *C07K 16/2803* (2013.01); *C07K 16/2827* (2013.01); *C07K 16/283* (2013.01); *C07K 16/2836* (2013.01); *C07K 16/2866* (2013.01); *C07K 16/2896* (2013.01); *C07K 16/30* (2013.01); *C07K 16/3007* (2013.01); *C07K 16/303* (2013.01); *C07K 16/3092* (2013.01); *C07K 16/32* (2013.01); *C12N 5/0636* (2013.01); *C12N 5/0637* (2013.01); *C12N 5/0638* (2013.01); *C12N 5/0646* (2013.01); *A61K 2239/21* (2023.05); *A61K 2239/53* (2023.05); *C07K 2317/53* (2013.01); *C07K 2317/55* (2013.01); *C07K 2317/622* (2013.01); *C07K 2319/02* (2013.01); *C07K 2319/03* (2013.01); *C07K 2319/30* (2013.01); *C07K 2319/32* (2013.01)

(58) Field of Classification Search

CPC ................ C07K 14/71; C07K 14/7051; C07K 14/70521; C07K 14/70578; C07K 14/7151; C07K 14/7153; C07K 16/2803; C07K 16/2827; C07K 16/283; C07K 16/2836; C07K 16/2866; C07K 16/2896; C07K 16/30; C07K 16/3007; C07K 16/303; C07K 16/3092; C07K 16/32; C07K 2317/53; C07K 2317/55; C07K 2319/02; C07K 2319/03; C07K 2319/30; C07K 2319/32; C07K 14/4702; C07K 2319/00; C07K 14/715; C07K 2317/565; C07K 2319/33; A61K 35/17; A61K 38/177; A61K 38/1774; A61K 38/179; A61K 39/3955; A61K 45/06; A61K 2039/5156; A61K 2039/844; A61K 39/001174; A61K 39/001111; A61P 35/00; C12N 2510/00; C12N 5/0636; C12N 5/0637; C12N 5/0638; C12N 5/0646

See application file for complete search history.

(56) References Cited

U.S. PATENT DOCUMENTS

2020/0369767 A1* 11/2020 Gibbs .................... A61K 35/17

FOREIGN PATENT DOCUMENTS

| | | | | |
|---|---|---|---|---|
| EP | 3845564 | A1 | 7/2021 | |
| WO | 2015173112 | A1 | 11/2015 | |
| WO | 2018018958 | A1 | 2/2018 | |
| WO | WO-2020042647 | A1 * | 3/2020 | ............. A61K 35/17 |

(Continued)

OTHER PUBLICATIONS

Arrese M., et al., "TGF- [beta] and Hepatocellular Carcinoma: When A Friend Becomes An Enemy", Current Protein and Peptide Science, vol. 19, No. 12, Oct. 4, 2018 (Oct. 4, 2018), pp. 1172-1179, XP055824646, ISSN: 1389-2037, DOI: 10.2174/1389203718666171117112619.

(Continued)

*Primary Examiner* — Emily A Cordas
*Assistant Examiner* — Constantina E Stavrou

(57) ABSTRACT

This disclosure relates to compositions and methods for treating cancer using armored chimeric antigen receptor cells.

24 Claims, 23 Drawing Sheets

Specification includes a Sequence Listing.

(56) References Cited

FOREIGN PATENT DOCUMENTS

WO WO-2021051390 A1 * 3/2021 ............ A61K 35/17

OTHER PUBLICATIONS

Bollard C.M., et al., "Tumor-Specific T-Cells Engineered to Overcome Tumor Immune Evasion Induce Clinical Responses in Patients With Relapsed Hodgkin Lymphoma," Journal of Clinical Oncology, vol. 36. No. 11, Apr. 10, 2018 (Apr. 10, 2018), pp. 1128-1139, ISSN: 1527-7755, XP9528705.

Boyerinas B., et al., "A Novel TGF-[beta]2/Interleukin Receptor Signal Conversion Platform That Protects CAR/TCR T Cells from TGF-[beta]2-Mediated Immune Suppression and Induces T Cell Supportive Signaling Networks," Blood, 59th Annual Meeting of the American Society of Hematology, Atlanta, GA, USA, Dec. 8, 2017, vol. 130, (Suppl_1): 1911, 3 Pages, XP086630647, DOI: 10.1182/BLOOD.V130.SUPPL_1.1911.1911, ISSN: 0006-4971.

Chu N., et al., "Dominant-Negative TGF.beta. Receptor 2 Enhances GPC3-Targeting CAR-T Cell Efficacy Against Hepatocellular Carcinoma," Journal for Immunotherapy of Cancer, vol. 8. No. 3, 109, Nov. 9, 2020, p. A68. XP055824652. 35th Annual Meeting of the Society for Immunotherapy of Cancer; Nov. 9-14, 2020 ISSN: 2051-1426. DOI: 10.1136/jitc-2020-SITC2020.0109.

Hu W., et al., "Chimeric Antigen Receptor Modified T Cell (CAR-T) Co-expressed with ICOSL-41BB Promote CAR-T Proliferation and Tumor Rejection," Biomedicine and Pharmacotherapy, Aug. 22, 2019, vol. 118, No. 109333, XP085828890, DOI: 10.1016/J.BIOPHA.2019.109333, ISSN: 0753-3322.

International Search Report and Written Opinion for International Application No. PCT/EP2021/060622, dated Aug. 16, 2021, 14 Pages.

Kloss C.C., et al., "Dominant-Negative TGF-[beta] Receptor Enhances PSMA-Targeted Human CART Cell Proliferation And Augments Prostate Cancer Eradication," Molecular Therapy, May 8, 2018, vol. 26. No. 7, pp. 1855-1866, XP055649123, DOI: 10.1016/j.ymthe.2018.05.003, ISSN: 1525-0016.

Li D., et al., "Persistent Polyfunctional Chimeric Antigen Receptor T Cells That Target Glypican 3 Eliminate Orthotopic Hepatocellular Carcinomas in Mice," Gastroenterology, Feb. 12, 2020, vol. 158, No. 8, pp. 2250-2285, XP086171057, DOI: 10.1053/J.GASTR0.2020.02.011, ISSN: 0016-5085.

Liu Y., et al., "Armored Inducible Expression of IL-12 Enhances Antitumor Activity of Glypican-3-Targeted Chimeric Antigen Receptor-Engineered T Cells in Hepatocellular Carcinoma," The Journal of Immunology., vol. 203. No. 1, May 29, 2019, pp. 198-207. XP055796753. ISSN: 0022-1767. DOI: 10.4049/jimmunol.1800033.

Yu M., et al., "Development of GPC3-Specific Chimeric Antigen Receptor-Engineered Natural Killer Cells for the Treatment of Hepatocellular Carcinoma," Molecular Therapy, Dec. 19, 2017, vol. 26, No. 2, pp. 366-378, ISSN: 1525-0016. DOI: 10.1016jj.ymthe.2017.12.012, XP055565104.

Zhang Q., et al., "Efficacy Against Human Prostate Cancer by Prostate-specific Membrane Antigen-specific, Transforming Growth Factor-β Insensitive Genetically Targeted CD8 + T-cells Derived from Patients with Metastatic Castrate-resistant Disease," European Urology, May 2018, vol. 73. No. 5, pp. 648-652, ISSN: 0302-2838. DOI: 10.1016/j.eururo.2017.12.008 the whole document, XP055825163.

* cited by examiner

*Order of Bars in each 3-Bar Group (L to R):
Unarmored / Armored AZ / Armored LN Figs. 8A, 8B, and 8C Ex vivo analysis: higher IFNg in the serum of mice treated with armored CART

SEQUENCE LISTING

<160> NUMBER OF SEQ ID NOS: 48

<210> SEQ ID NO 1
<211> LENGTH: 241
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Glu Val Gln Leu Leu Glu Ser Gly Gly Gly Leu Val Gln Pro Gly Gly

-continued

```
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Arg Tyr Phe Asp Tyr Trp Gly Gln Gly Thr Met Val
            100                 105                 110

Thr Val Ser Ser Gly Gly Gly Gly Ser Gly Gly Gly Gly Ser Gly Gly
        115                 120                 125

Gly Gly Ser Ser Tyr Glu Leu Thr Gln Pro Pro Ser Ala Ser Gly Thr
    130                 135                 140

Pro Gly Gln Arg Val Thr Ile Ser Cys Ser Gly Gly Ser Ser Asn Ile
145                 150                 155                 160

Gly Ser Asn Thr Val Asn Trp Phe Arg Gln Leu Pro Gly Thr Ala Pro
                165                 170                 175

Lys Leu Leu Val Tyr Phe Asn Asn Gln Arg Pro Ser Gly Val Pro Asp
            180                 185                 190

Arg Phe Ser Gly Ser Lys Ser Gly Thr Ser Ala Ser Leu Ala Ile Gly
        195                 200                 205

Gly Leu Gln Ser Asp Asp Glu Ala Asp Tyr Tyr Cys Val Ala Trp Asp
    210                 215                 220

Asp Ser Leu Asn Ala Pro Val Phe Gly Gly Gly Thr Lys Val Thr Val
225                 230                 235                 240

Leu


<210> SEQ ID NO 2
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Lys Arg Tyr Phe Asp Tyr Trp Gly Gln Gly Thr Met Val
            100                 105                 110

Thr Val Ser Ser Gly Gly Gly Gly Ser Gly Gly Gly Gly Ser Gly Gly
```

```
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Ser Gly Gly Ser Ser Asp Ile
145                 150                 155                 160

Gly Ser Asn Thr Val Asn Trp Tyr Gln Gln Leu Pro Gly Thr Ala Pro
                165                 170                 175

Lys Leu Leu Ile Tyr Tyr Asn Asn Gln Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Ala Thr Trp Asp
    210                 215                 220

Asp Arg Met Tyr Ser Pro Val Phe Gly Gly Gly Thr Lys Leu Thr Val
225                 230                 235                 240

Leu


<210> SEQ ID NO 3
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Leu Leu Leu Val Thr Ser Leu Leu Leu Cys Glu Leu Pro His Pro
1               5                   10                  15

Ala Phe Leu Leu Ile Pro Gly Val His Ser Glu Val Gln Leu Leu Glu
            20                  25                  30

Ser Gly Gly Gly Leu Val Gln Pro Gly Gly Ser Leu Arg Leu Ser Cys
        35                  40                  45

Ala Ala Ser Gly Phe Thr Phe Ser Ser Tyr Ala Met Ser Trp Val Arg
    50                  55                  60

Gln Ala Pro Gly Lys Gly Leu Glu Trp Val Ser Ala Ile Ser Gly Ser
65                  70                  75                  80

Gly Gly Ser Thr Tyr Tyr Ala Asp Ser Val Lys Gly Arg Phe Thr Ile
                85                  90                  95

Ser Arg Asp Asn Ser Lys Asn Thr Leu Tyr Leu Gln Met Asn Ser Leu
            100                 105                 110

Arg Ala Glu Asp Thr Ala Val Tyr Tyr Cys Ala Arg Gly Lys Arg Tyr
        115                 120                 125

Phe Asp Tyr Trp Gly Gln Gly Thr Met Val Thr Val Ser Ser Gly Gly
    130                 135                 140

Gly Gly Ser Gly Gly Gly Gly Ser Gly Gly Gly Gly Ser Ser Tyr Glu
145                 150                 155                 160

Leu Thr Gln Pro Pro Ser Ala Ser Gly Thr Pro Gly Gln Arg Val Thr
                165                 170                 175

Ile Ser Cys Ser Gly Gly Ser Ser Asn Ile Gly Ser Asn Thr Val Asn
            180                 185                 190

Trp Phe Arg Gln Leu Pro Gly Thr Ala Pro Lys Leu Leu Val Tyr Phe
        195                 200                 205

Asn Asn Gln Arg Pro Ser Gly Val Pro Asp Arg Phe Ser Gly Ser Lys
    210                 215                 220

Ser Gly Thr Ser Ala Ser Leu Ala Ile Gly Gly Leu Gln Ser Asp Asp
```

```
225                 230                 235                 240

Glu Ala Asp Tyr Tyr Cys Val Ala Trp Asp Asp Ser Leu Asn Ala Pro
                245                 250                 255

Val Phe Gly Gly Gly Thr Lys Val Thr Val Leu Glu Ser Lys Tyr Gly
            260                 265                 270

Pro Pro Cys Pro Pro Cys Pro Phe Trp Val Leu Val Val Val Gly Gly
        275                 280                 285

Val Leu Ala Cys Tyr Ser Leu Leu Val Thr Val Ala Phe Ile Ile Phe
    290                 295                 300

Trp Val Lys Arg Gly Arg Lys Lys Leu Leu Tyr Ile Phe Lys Gln Pro
305                 310                 315                 320

Phe Met Arg Pro Val Gln Thr Thr Gln Glu Glu Asp Gly Cys Ser Cys
                325                 330                 335

Arg Phe Pro Glu Glu Glu Glu Gly Gly Cys Glu Leu Arg Val Lys Phe
            340                 345                 350

Ser Arg Ser Ala Asp Ala Pro Ala Tyr Gln Gln Gly Gln Asn Gln Leu
        355                 360                 365

Tyr Asn Glu Leu Asn Leu Gly Arg Arg Glu Glu Tyr Asp Val Leu Asp
    370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
            420                 425                 430

Gly His Asp Gly Leu Tyr Gln Gly Leu Ser Thr Ala Thr Lys Asp Thr
        435                 440                 445

Tyr Asp Ala Leu His Met Gln Ala Leu Pro Pro Arg
    450                 455                 460


<210> SEQ ID NO 4
<211> LENGTH: 318
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Leu Leu Leu Val Thr Ser Leu Leu Leu Cys Glu Leu Pro His Pro
1               5                   10                  15

Ala Phe Leu Leu Ile Pro Gly Val His Ser Glu Val Gln Leu Leu Glu
            20                  25                  30

Ser Gly Gly Gly Leu Val Gln Pro Gly Gly Ser Leu Arg Leu Ser Cys
        35                  40                  45

Ala Ala Ser Gly Phe Thr Phe Ser Ser Tyr Ala Met Ser Trp Val Arg
    50                  55                  60

Gln Ala Pro Gly Lys Gly Leu Glu Trp Val Ser Ala Ile Ser Gly Ser
65                  70                  75                  80

Gly Gly Ser Thr Tyr Tyr Ala Asp Ser Val Lys Gly Arg Phe Thr Ile
                85                  90                  95

Ser Arg Asp Asn Ser Lys Asn Thr Leu Tyr Leu Gln Met Asn Ser Leu
            100                 105                 110

Arg Ala Glu Asp Thr Ala Val Tyr Tyr Cys Ala Arg Gly Lys Arg Tyr
        115                 120                 125
```

```
Phe Asp Tyr Trp Gly Gln Gly Thr Met Val Thr Val Ser Ser Gly Gly
    130                 135                 140

Gly Gly Ser Gly Gly Gly Gly Ser Gly Gly Gly Gly Ser Ser Tyr Glu
145                 150                 155                 160

Leu Thr Gln Pro Pro Ser Ala Ser Gly Thr Pro Gly Gln Arg Val Thr
                165                 170                 175

Ile Ser Cys Ser Gly Gly Ser Ser Asn Ile Gly Ser Asn Thr Val Asn
            180                 185                 190

Trp Phe Arg Gln Leu Pro Gly Thr Ala Pro Lys Leu Leu Val Tyr Phe
        195                 200                 205

Asn Asn Gln Arg Pro Ser Gly Val Pro Asp Arg Phe Ser Gly Ser Lys
    210                 215                 220

Ser Gly Thr Ser Ala Ser Leu Ala Ile Gly Gly Leu Gln Ser Asp Asp
225                 230                 235                 240

Glu Ala Asp Tyr Tyr Cys Val Ala Trp Asp Asp Ser Leu Asn Ala Pro
                245                 250                 255

Val Phe Gly Gly Gly Thr Lys Val Thr Val Leu Glu Ser Lys Tyr Gly
            260                 265                 270

Pro Pro Cys Pro Pro Cys Pro Phe Trp Val Leu Val Val Val Gly Gly
        275                 280                 285

Val Leu Ala Cys Tyr Ser Leu Leu Val Thr Val Ala Phe Ile Ile Phe
    290                 295                 300

Trp Val Arg Val Lys Phe Ser Arg Ser Ala Asp Ala Pro Ala
305                 310                 315


<210> SEQ ID NO 5
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Leu Leu Leu Val Thr Ser Leu Leu Leu Cys Glu Leu Pro His Pro
1               5                   10                  15

Ala Phe Leu Leu Ile Pro Gly Val His Ser Glu Val Gln Leu Leu Glu
            20                  25                  30

Ser Gly Gly Gly Leu Val Gln Pro Gly Gly Ser Leu Arg Leu Ser Cys
        35                  40                  45

Ala Ala Ser Gly Phe Thr Phe Ser Ser Tyr Ala Met Ser Trp Val Arg
    50                  55                  60

Gln Ala Pro Gly Lys Gly Leu Glu Trp Val Ser Ala Ile Ser Gly Ser
65                  70                  75                  80

Gly Gly Ser Thr Tyr Tyr Ala Asp Ser Val Lys Gly Arg Phe Thr Ile
                85                  90                  95

Ser Arg Asp Asn Ser Lys Asn Thr Leu Tyr Leu Gln Met Asn Ser Leu
            100                 105                 110

Arg Ala Glu Asp Thr Ala Val Tyr Tyr Cys Ala Arg Gly Lys Arg Tyr
        115                 120                 125

Phe Asp Tyr Trp Gly Gln Gly Thr Met Val Thr Val Ser Ser Gly Gly
    130                 135                 140

Gly Gly Ser Gly Gly Gly Gly Ser Gly Gly Gly Gly Ser Ser Tyr Glu
145                 150                 155                 160

Leu Thr Gln Pro Pro Ser Ala Ser Gly Thr Pro Gly Gln Arg Val Thr
                165                 170                 175
```

Ile Ser Cys Ser Gly Gly Ser Ser Asn Ile Gly Ser Asn Thr Val Asn
180 185 190

Trp Phe Arg Gln Leu Pro Gly Thr Ala Pro Lys Leu Leu Val Tyr Phe
195 200 205

Asn Asn Gln Arg Pro Ser Gly Val Pro Asp Arg Phe Ser Gly Ser Lys
210 215 220

Ser Gly Thr Ser Ala Ser Leu Ala Ile Gly Gly Leu Gln Ser Asp Asp
225 230 235 240

Glu Ala Asp Tyr Tyr Cys Val Ala Trp Asp Asp Ser Leu Asn Ala Pro
245 250 255

Val Phe Gly Gly Gly Thr Lys Val Thr Val Leu Glu Ser Lys Tyr Gly
260 265 270

Pro Pro Cys Pro Pro Cys Pro Phe Trp Val Leu Val Val Val Gly Gly
275 280 285

Val Leu Ala Cys Tyr Ser Leu Leu Val Thr Val Ala Phe Ile Ile Phe
290 295 300

Trp Val Arg Ser Lys Arg Ser Arg Leu Leu His Ser Asp Tyr Met Asn
305 310 315 320

Met Thr Pro Arg Arg Pro Gly Pro Thr Arg Lys His Tyr Gln Pro Tyr
325 330 335

Ala Pro Pro Arg Asp Phe Ala Ala Tyr Arg Ser Arg Val Lys Phe Ser
340 345 350

Arg Ser Ala Asp Ala Pro Ala Tyr Gln Gln Gly Gln Asn Gln Leu Tyr
355 360 365

Asn Glu Leu Asn Leu Gly Arg Arg Glu Glu Tyr Asp Val Leu Asp Lys
370 375 380

Arg Arg Gly Arg Asp Pro Glu Met Gly Gly Lys Pro Arg Arg Lys Asn
385 390 395 400

Pro Gln Glu Gly Leu Tyr Asn Glu Leu Gln Lys Asp Lys Met Ala Glu
405 410 415

Ala Tyr Ser Glu Ile Gly Met Lys Gly Glu Arg Arg Arg Gly Lys Gly
420 425 430

His Asp Gly Leu Tyr Gln Gly Leu Ser Thr Ala Thr Lys Asp Thr Tyr
435 440 445

Asp Ala Leu His Met Gln Ala Leu Pro Pro Arg
450 455

<210> SEQ ID NO 6
<211> LENGTH: 501
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

Met Leu Leu Leu Val Thr Ser Leu Leu Leu Cys Glu Leu Pro His Pro
1 5 10 15

Ala Phe Leu Leu Ile Pro Gly Val His Ser Glu Val Gln Leu Leu Glu
20 25 30

Ser Gly Gly Gly Leu Val Gln Pro Gly Gly Ser Leu Arg Leu Ser Cys
35 40 45

Ala Ala Ser Gly Phe Thr Phe Ser Ser Tyr Ala Met Ser Trp Val Arg
50 55 60

Gln Ala Pro Gly Lys Gly Leu Glu Trp Val Ser Ala Ile Ser Gly Ser

-continued

```
65                  70                  75                  80

Gly Gly Ser Thr Tyr Tyr Ala Asp Ser Val Lys Gly Arg Phe Thr Ile
                85                  90                  95

Ser Arg Asp Asn Ser Lys Asn Thr Leu Tyr Leu Gln Met Asn Ser Leu
            100                 105                 110

Arg Ala Glu Asp Thr Ala Val Tyr Tyr Cys Ala Arg Gly Lys Arg Tyr
        115                 120                 125

Phe Asp Tyr Trp Gly Gln Gly Thr Met Val Thr Val Ser Ser Gly Gly
    130                 135                 140

Gly Gly Ser Gly Gly Gly Gly Ser Gly Gly Gly Gly Ser Ser Tyr Glu
145                 150                 155                 160

Leu Thr Gln Pro Pro Ser Ala Ser Gly Thr Pro Gly Gln Arg Val Thr
                165                 170                 175

Ile Ser Cys Ser Gly Gly Ser Ser Asn Ile Gly Ser Asn Thr Val Asn
            180                 185                 190

Trp Phe Arg Gln Leu Pro Gly Thr Ala Pro Lys Leu Leu Val Tyr Phe
        195                 200                 205

Asn Asn Gln Arg Pro Ser Gly Val Pro Asp Arg Phe Ser Gly Ser Lys
    210                 215                 220

Ser Gly Thr Ser Ala Ser Leu Ala Ile Gly Gly Leu Gln Ser Asp Asp
225                 230                 235                 240

Glu Ala Asp Tyr Tyr Cys Val Ala Trp Asp Asp Ser Leu Asn Ala Pro
                245                 250                 255

Val Phe Gly Gly Gly Thr Lys Val Thr Val Leu Glu Ser Lys Tyr Gly
            260                 265                 270

Pro Pro Cys Pro Pro Cys Pro Phe Trp Val Leu Val Val Val Gly Gly
        275                 280                 285

Val Leu Ala Cys Tyr Ser Leu Leu Val Thr Val Ala Phe Ile Ile Phe
    290                 295                 300

Trp Val Arg Ser Lys Arg Ser Arg Leu Leu His Ser Asp Tyr Met Asn
305                 310                 315                 320

Met Thr Pro Arg Arg Pro Gly Pro Thr Arg Lys His Tyr Gln Pro Tyr
                325                 330                 335

Ala Pro Pro Arg Asp Phe Ala Ala Tyr Arg Ser Lys Arg Gly Arg Lys
            340                 345                 350

Lys Leu Leu Tyr Ile Phe Lys Gln Pro Phe Met Arg Pro Val Gln Thr
        355                 360                 365

Thr Gln Glu Glu Asp Gly Cys Ser Cys Arg Phe Pro Glu Glu Glu Glu
    370                 375                 380

Gly Gly Cys Glu Leu Arg Val Lys Phe Ser Arg Ser Ala Asp Ala Pro
385                 390                 395                 400

Ala Tyr Gln Gln Gly Gln Asn Gln Leu Tyr Asn Glu Leu Asn Leu Gly
                405                 410                 415

Arg Arg Glu Glu Tyr Asp Val Leu Asp Lys Arg Arg Gly Arg Asp Pro
            420                 425                 430

Glu Met Gly Gly Lys Pro Arg Arg Lys Asn Pro Gln Glu Gly Leu Tyr
        435                 440                 445

Asn Glu Leu Gln Lys Asp Lys Met Ala Glu Ala Tyr Ser Glu Ile Gly
    450                 455                 460

Met Lys Gly Glu Arg Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
                485                 490                 495
```

Ala Leu Pro Pro Arg
500

<210> SEQ ID NO 7
<211> LENGTH: 456
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 7

Met Leu Leu Leu Val Thr Ser Leu Leu Leu Cys Glu Leu Pro His Pro
1 5 10 15

Ala Phe Leu Leu Ile Pro Glu Val Gln Leu Leu Glu Ser Gly Gly Gly
20 25 30

Leu Val Gln Pro Gly Gly Ser Leu Arg Leu Ser Cys Ala Ala Ser Gly
35 40 45

Phe Thr Phe Ser Ser Tyr Ala Met Ser Trp Val Arg Gln Ala Pro Gly
50 55 60

Lys Gly Leu Glu Trp Val Ser Ala Ile Ser Gly Ser Gly Gly Ser Thr
65 70 75 80

Tyr Tyr Ala Asp Ser Val Lys Gly Arg Phe Thr Ile Ser Arg Asp Asn
85 90 95

Ser Lys Asn Thr Leu Tyr Leu Gln Met Asn Ser Leu Arg Ala Glu Asp
100 105 110

Thr Ala Val Tyr Tyr Cys Ala Lys Gly Lys Arg Tyr Phe Asp Tyr Trp
115 120 125

Gly Gln Gly Thr Met Val Thr Val Ser Ser Gly Gly Gly Gly Ser Gly
130 135 140

Gly Gly Gly Ser Gly Gly Gly Gly Ser Gln Ser Val Leu Thr Gln Pro
145 150 155 160

Pro Ser Ala Ser Gly Thr Pro Gly Gln Arg Val Thr Ile Ser Cys Ser
165 170 175

Gly Gly Ser Ser Asp Ile Gly Ser Asn Thr Val Asn Trp Tyr Gln Gln
180 185 190

Leu Pro Gly Thr Ala Pro Lys Leu Leu Ile Tyr Tyr Asn Asn Gln Arg
195 200 205

Pro Ser Gly Val Pro Asp Arg Phe Ser Gly Ser Lys Ser Gly Thr Ser
210 215 220

Ala Ser Leu Ala Ile Ser Gly Leu Gln Ser Glu Asp Glu Ala Asp Tyr
225 230 235 240

Tyr Cys Ala Thr Trp Asp Asp Arg Met Tyr Ser Pro Val Phe Gly Gly
245 250 255

Gly Thr Lys Leu Thr Val Leu Glu Ser Lys Tyr Gly Pro Pro Cys Pro
260 265 270

Pro Cys Pro Phe Trp Val Leu Val Val Val Gly Gly Val Leu Ala Cys
275 280 285

Tyr Ser Leu Leu Val Thr Val Ala Phe Ile Ile Phe Trp Val Lys Arg
290 295 300

Gly Arg Lys Lys Leu Leu Tyr Ile Phe Lys Gln Pro Phe Met Arg Pro
305 310 315 320

Val Gln Thr Thr Gln Glu Glu Asp Gly Cys Ser Cys Arg Phe Pro Glu
325 330 335

Glu Glu Glu Gly Gly Cys Glu Leu Arg Val Lys Phe Ser Arg Ser Ala

```
            340                 345                 350

Asp Ala Pro Ala Tyr Gln Gln Gly Gln Asn Gln Leu Tyr Asn Glu Leu
        355                 360                 365

Asn Leu Gly Arg Arg Glu Glu Tyr Asp Val Leu Asp Lys Arg Arg Gly
    370                 375                 380

Arg Asp Pro Glu Met Gly Gly Lys Pro Arg Arg Lys Asn Pro Gln Glu
385                 390                 395                 400

Gly Leu Tyr Asn Glu Leu Gln Lys Asp Lys Met Ala Glu Ala Tyr Ser
                405                 410                 415

Glu Ile Gly Met Lys Gly Glu Arg Arg Arg Gly Lys Gly His Asp Gly
            420                 425                 430

Leu Tyr Gln Gly Leu Ser Thr Ala Thr Lys Asp Thr Tyr Asp Ala Leu
        435                 440                 445

His Met Gln Ala Leu Pro Pro Arg
    450                 455


<210> SEQ ID NO 8
<211> LENGTH: 314
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Leu Leu Leu Val Thr Ser Leu Leu Leu Cys Glu Leu Pro His Pro
1               5                   10                  15

Ala Phe Leu Leu Ile Pro Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ala Ile Ser Gly Ser Gly Gly Ser Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Gly Lys Arg Tyr Phe Asp Tyr Trp
        115                 120                 125

Gly Gln Gly Thr Met Val Thr Val Ser Ser Gly Gly Gly Gly Ser Gly
    130                 135                 140

Gly Gly Gly Ser Gly Gly Gly Gly Ser Gln Ser Val Leu Thr Gln Pro
145                 150                 155                 160

Pro Ser Ala Ser Gly Thr Pro Gly Gln Arg Val Thr Ile Ser Cys Ser
                165                 170                 175

Gly Gly Ser Ser Asp Ile Gly Ser Asn Thr Val Asn Trp Tyr Gln Gln
            180                 185                 190

Leu Pro Gly Thr Ala Pro Lys Leu Leu Ile Tyr Tyr Asn Asn Gln Arg
        195                 200                 205

Pro Ser Gly Val Pro Asp Arg Phe Ser Gly Ser Lys Ser Gly Thr Ser
    210                 215                 220

Ala Ser Leu Ala Ile Ser Gly Leu Gln Ser Glu Asp Glu Ala Asp Tyr
225                 230                 235                 240
```

-continued

```
Tyr Cys Ala Thr Trp Asp Asp Arg Met Tyr Ser Pro Val Phe Gly Gly
                245                 250                 255

Gly Thr Lys Leu Thr Val Leu Glu Ser Lys Tyr Gly Pro Pro Cys Pro
            260                 265                 270

Pro Cys Pro Phe Trp Val Leu Val Val Val Gly Gly Val Leu Ala Cys
        275                 280                 285

Tyr Ser Leu Leu Val Thr Val Ala Phe Ile Ile Phe Trp Val Arg Val
    290                 295                 300

Lys Phe Ser Arg Ser Ala Asp Ala Pro Ala
305                 310


<210> SEQ ID NO 9
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Leu Leu Leu Val Thr Ser Leu Leu Leu Cys Glu Leu Pro His Pro
1               5                   10                  15

Ala Phe Leu Leu Ile Pro Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ala Ile Ser Gly Ser Gly Gly Ser Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Gly Lys Arg Tyr Phe Asp Tyr Trp
        115                 120                 125

Gly Gln Gly Thr Met Val Thr Val Ser Ser Gly Gly Gly Gly Ser Gly
    130                 135                 140

Gly Gly Gly Ser Gly Gly Gly Gly Ser Gln Ser Val Leu Thr Gln Pro
145                 150                 155                 160

Pro Ser Ala Ser Gly Thr Pro Gly Gln Arg Val Thr Ile Ser Cys Ser
                165                 170                 175

Gly Gly Ser Ser Asp Ile Gly Ser Asn Thr Val Asn Trp Tyr Gln Gln
            180                 185                 190

Leu Pro Gly Thr Ala Pro Lys Leu Leu Ile Tyr Tyr Asn Asn Gln Arg
        195                 200                 205

Pro Ser Gly Val Pro Asp Arg Phe Ser Gly Ser Lys Ser Gly Thr Ser
    210                 215                 220

Ala Ser Leu Ala Ile Ser Gly Leu Gln Ser Glu Asp Glu Ala Asp Tyr
225                 230                 235                 240

Tyr Cys Ala Thr Trp Asp Asp Arg Met Tyr Ser Pro Val Phe Gly Gly
                245                 250                 255

Gly Thr Lys Leu Thr Val Leu Glu Ser Lys Tyr Gly Pro Pro Cys Pro
            260                 265                 270

Pro Cys Pro Phe Trp Val Leu Val Val Val Gly Gly Val Leu Ala Cys
        275                 280                 285
```

```
Tyr Ser Leu Leu Val Thr Val Ala Phe Ile Ile Phe Trp Val Arg Ser
    290                 295                 300

Lys Arg Ser Arg Leu Leu His Ser Asp Tyr Met Asn Met Thr Pro Arg
305                 310                 315                 320

Arg Pro Gly Pro Thr Arg Lys His Tyr Gln Pro Tyr Ala Pro Pro Arg
                325                 330                 335

Asp Phe Ala Ala Tyr Arg Ser Arg Val Lys Phe Ser Arg Ser Ala Asp
            340                 345                 350

Ala Pro Ala Tyr Gln Gln Gly Gln Asn Gln Leu Tyr Asn Glu Leu Asn
        355                 360                 365

Leu Gly Arg Arg Glu Glu Tyr Asp Val Leu Asp Lys Arg Arg Gly Arg
    370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                405                 410                 415

Ile Gly Met Lys Gly Glu Arg Arg Arg Gly Lys Gly His Asp Gly Leu
            420                 425                 430

Tyr Gln Gly Leu Ser Thr Ala Thr Lys Asp Thr Tyr Asp Ala Leu His
        435                 440                 445

Met Gln Ala Leu Pro Pro Arg
    450                 455


<210> SEQ ID NO 10
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Leu Leu Leu Val Thr Ser Leu Leu Leu Cys Glu Leu Pro His Pro
1               5                   10                  15

Ala Phe Leu Leu Ile Pro Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ala Ile Ser Gly Ser Gly Gly Ser Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Gly Lys Arg Tyr Phe Asp Tyr Trp
        115                 120                 125

Gly Gln Gly Thr Met Val Thr Val Ser Ser Gly Gly Gly Gly Ser Gly
    130                 135                 140

Gly Gly Gly Ser Gly Gly Gly Gly Ser Gln Ser Val Leu Thr Gln Pro
145                 150                 155                 160

Pro Ser Ala Ser Gly Thr Pro Gly Gln Arg Val Thr Ile Ser Cys Ser
                165                 170                 175

Gly Gly Ser Ser Asp Ile Gly Ser Asn Thr Val Asn Trp Tyr Gln Gln
```

```
            180                 185                 190

Leu Pro Gly Thr Ala Pro Lys Leu Leu Ile Tyr Tyr Asn Asn Gln Arg
        195                 200                 205

Pro Ser Gly Val Pro Asp Arg Phe Ser Gly Ser Lys Ser Gly Thr Ser
    210                 215                 220

Ala Ser Leu Ala Ile Ser Gly Leu Gln Ser Glu Asp Glu Ala Asp Tyr
225                 230                 235                 240

Tyr Cys Ala Thr Trp Asp Asp Arg Met Tyr Ser Pro Val Phe Gly Gly
                245                 250                 255

Gly Thr Lys Leu Thr Val Leu Glu Ser Lys Tyr Gly Pro Pro Cys Pro
            260                 265                 270

Pro Cys Pro Phe Trp Val Leu Val Val Val Gly Gly Val Leu Ala Cys
        275                 280                 285

Tyr Ser Leu Leu Val Thr Val Ala Phe Ile Ile Phe Trp Val Arg Ser
    290                 295                 300

Lys Arg Ser Arg Leu Leu His Ser Asp Tyr Met Asn Met Thr Pro Arg
305                 310                 315                 320

Arg Pro Gly Pro Thr Arg Lys His Tyr Gln Pro Tyr Ala Pro Pro Arg
                325                 330                 335

Asp Phe Ala Ala Tyr Arg Ser Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg


<210> SEQ ID NO 11
<211> LENGTH: 1383
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

atgctgctgc tggtgacaag cctgctgctg tgcgaactgc cccatcccgc cttcctgctg      60

attcctggtg tacactccga ggtgcagctg ttggagtctg ggggaggctt ggtacagcct     120

ggggggtccc tgagactctc ctgtgcagcc tctggattca cctttagcag ctatgccatg     180

agctgggtcc gccaggctcc agggaagggg ctggagtggg tctcagctat tagtggtagt     240
```

```
ggtggtagca catactacgc agactccgtg aagggccggt tcaccatctc cagagacaat    300

tccaagaaca cgctgtatct gcaaatgaac agcctgagag ccgaggacac ggccgtgtat    360

tactgtgcga gaggaaagcg atactttgac tactggggcc aggggacaat ggtcaccgtc    420

tcgagtggtg gggggggcag cggtggtgga ggctctggtg gaggagggag ctcctatgag    480

ctgactcagc caccctcagc gtctgggacc cccgggcaga gggtcaccat ctcttgttct    540

ggaggcagct ccaacatcgg aagtaatact gtaaactggt tccggcagct cccaggaacg    600

gcccccaaac tcctcgttta ttttaataat cagcgaccct caggggtccc tgaccgattc    660

tctggctcca agtctggcac ctcggcctcc ctggccatcg gtgggctcca gtctgacgat    720

gaggctgact attactgtgt agcatgggat gactctctga atgctccggt gttcggcgga    780

gggaccaagg tcaccgtcct agagagcaaa tatggaccac catgccctcc atgtcctttt    840

tgggtcctgg tggtcgtggg aggcgtgctg gcatgttatt ctctgctggt cacagtggct    900

ttcatcatct tctgggtcaa gcgaggccgg aagaaactgc tgtacatctt caaacagcct    960

tttatgcgcc cagtgcagac aactcaggag gaagacggct gctcttgtcg gttccccgag   1020

gaagaggaag ggggatgtga gctgcgcgtg aagttttctc gaagtgccga tgctcctgca   1080

tatcagcagg gacagaacca gctgtacaac gagctgaatc tgggccggag agaggaatac   1140

gacgtgctgg ataagaggcg cggcagagac ccagaaatgg gcgggaagcc acgacggaaa   1200

aacccccagg aggggctgta taatgaactg cagaaggaca aaatggccga ggcttacagc   1260

gaaatcggga tgaagggaga gagaaggcgc ggaaaaggcc acgatggact gtatcagggc   1320

ctgagcactg ccaccaagga cacctacgat gctctgcaca tgcaggcact gccacccagg   1380

tga                                                                 1383
```

<210> SEQ ID NO 12
<211> LENGTH: 957
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
atgctgctgc tggtgacaag cctgctgctg tgcgaactgc cccatcccgc cttcctgctg     60

attcctggtg tacactccga ggtgcagctg ttggagtctg gggaggcttt ggtacagcct    120

ggggggtccc tgagactctc ctgtgcagcc tctggattca cctttagcag ctatgccatg    180

agctgggtcc gccaggctcc agggaagggg ctggagtggg tctcagctat tagtggtagt    240

ggtggtagca catactacgc agactccgtg aagggccggt tcaccatctc cagagacaat    300

tccaagaaca cgctgtatct gcaaatgaac agcctgagag ccgaggacac ggccgtgtat    360

tactgtgcga gaggaaagcg atactttgac tactggggcc aggggacaat ggtcaccgtc    420

tcgagtggtg gggggggcag cggtggtgga ggctctggtg gaggagggag ctcctatgag    480

ctgactcagc caccctcagc gtctgggacc cccgggcaga gggtcaccat ctcttgttct    540

ggaggcagct ccaacatcgg aagtaatact gtaaactggt tccggcagct cccaggaacg    600

gcccccaaac tcctcgttta ttttaataat cagcgaccct caggggtccc tgaccgattc    660

tctggctcca agtctggcac ctcggcctcc ctggccatcg gtgggctcca gtctgacgat    720

gaggctgact attactgtgt agcatgggat gactctctga atgctccggt gttcggcgga    780

gggaccaagg tcaccgtcct agagagcaaa tatggaccac catgccctcc atgtcctttt    840
```

tgggtcctgg tggtcgtggg aggcgtgctg gcatgttatt ctctgctggt cacagtggct 900
ttcatcatct tctgggtccg cgtgaagttt tctcgaagtg ccgatgctcc tgcatga 957

<210> SEQ ID NO 13
<211> LENGTH: 1380
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
atgctgctgc tggtgacaag cctgctgctg tgcgaactgc cccatcccgc cttcctgctg 60
attcctggtg tacactccga ggtgcagctg ttggagtctg ggggaggctt ggtacagcct 120
ggggggtccc tgagactctc ctgtgcagcc tctggattca cctttagcag ctatgccatg 180
agctgggtcc gccaggctcc agggaagggg ctggagtggg tctcagctat tagtggtagt 240
ggtggtagca catactacgc agactccgtg aagggccggt tcaccatctc cagagacaat 300
tccaagaaca cgctgtatct gcaaatgaac agcctgagag ccgaggacac ggccgtgtat 360
tactgtgcga gaggaaagcg atactttgac tactggggcc aggggacaat ggtcaccgtc 420
tcgagtggtg gggggggcag cggtggtgga ggctctggtg gaggagggag ctcctatgag 480
ctgactcagc caccctcagc gtctgggacc cccgggcaga gggtcaccat ctcttgttct 540
ggaggcagct ccaacatcgg aagtaatact gtaaactggt tccggcagct cccaggaacg 600
gcccccaaac tcctcgttta ttttaataat cagcgaccct caggggtccc tgaccgattc 660
tctggctcca agtctggcac ctcggcctcc ctggccatcg gtgggctcca gtctgacgat 720
gaggctgact attactgtgt agcatgggat gactctctga atgctccggt gttcggcgga 780
gggaccaagg tcaccgtcct agagagcaaa tatggaccac catgccctcc atgtcctttt 840
tgggtcctgg tggtcgtggg aggcgtgctg gcatgttatt ccctgctggt cactgtggcc 900
ttcatcatct tctgggtgcg gagcaagcgg agccggctgc tgcactctga ctacatgaac 960
atgactccac ggagacccgg ccctacccgg aaacattatc agccctacgc cccacccaga 1020
gattttgccg cttataggtc cagggtgaag ttttctcgca gtgcagatgc ccctgcttat 1080
cagcagggac agaatcagct gtacaacgag ctgaatctgg gcaggcgcga ggaatacgac 1140
gtgctggata agcgacgggg cagagacccc gaaatgggag ggaagcccag aaggaaaaac 1200
cctcaggagg ggctgtataa tgaactgcag aaggacaaaa tggcagaggc ctacagtgaa 1260
atcgggatga agggagagcg ccgacgggga aaaggccacg atggactgta tcagggcctg 1320
tctactgcca ccaaggacac ctacgatgcc ctgcacatgc aggctctgcc tccacgctga 1380

<210> SEQ ID NO 14
<211> LENGTH: 1506
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14
atgctgctgc tggtgacaag cctgctgctg tgcgaactgc cccatcccgc cttcctgctg 60
attcctggtg tacactccga ggtgcagctg ttggagtctg ggggaggctt ggtacagcct 120
ggggggtccc tgagactctc ctgtgcagcc tctggattca cctttagcag ctatgccatg 180

-continued

```
agctgggtcc gccaggctcc agggaagggg ctggagtggg tctcagctat tagtggtagt    240

ggtggtagca catactacgc agactccgtg aagggccggt tcaccatctc cagagacaat    300

tccaagaaca cgctgtatct gcaaatgaac agcctgagag ccgaggacac ggccgtgtat    360

tactgtgcga gaggaaagcg atactttgac tactggggcc aggggacaat ggtcaccgtc    420

tcgagtggtg gggggggcag cggtggtgga ggctctggtg gaggagggag ctcctatgag    480

ctgactcagc caccctcagc gtctgggacc cccgggcaga gggtcaccat ctcttgttct    540

ggaggcagct ccaacatcgg aagtaatact gtaaactggt tccggcagct cccaggaacg    600

gcccccaaac tcctcgttta ttttaataat cagcgaccct caggggtccc tgaccgattc    660

tctggctcca agtctggcac ctcggcctcc ctggccatcg gtgggctcca gtctgacgat    720

gaggctgact attactgtgt agcatgggat gactctctga atgctccggt gttcggcgga    780

gggaccaagg tcaccgtcct agagagcaaa tatggaccac catgccctcc atgtcctttt    840

tgggtcctgg tggtcgtggg aggcgtgctg gcatgttatt ccctgctggt cactgtggcc    900

ttcatcatct tctgggtgcg gagcaagcgg agccggctgc tgcactctga ctacatgaac    960

atgactccac ggagacccgg ccctacccgg aaacattatc agccctacgc cccacccaga   1020

gattttgccg cttataggtc caagcgcggc cgaaagaaac tgctgtacat cttcaaacag   1080

cccttcatga gacccgtcca gacaactcag gaggaagacg gctgcagctg taggttcccc   1140

gaggaagagg aagggggatg tgagctgagg gtgaagtttt ctcgcagtgc agatgcccct   1200

gcttatcagc agggacagaa tcagctgtac aacgagctga atctgggcag gcgcgaggaa   1260

tacgacgtgc tggataagcg acggggcaga gaccccgaaa tgggagggaa gcccagaagg   1320

aaaaaccctc aggaggggct gtataatgaa ctgcagaagg acaaaatggc agaggcctac   1380

agtgaaatcg ggatgaaggg agagcgccga cggggaaaag gccacgatgg actgtatcag   1440

ggcctgtcta ctgccaccaa ggacacctac gatgccctgc acatgcaggc tctgcctcca   1500

cgctga                                                              1506
```

<210> SEQ ID NO 15
<211> LENGTH: 1371
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
atgctgctgc tggtgacaag cctgctgctg tgcgaactgc cccatcccgc cttcctgctg     60

attcctgagg tccagctgct ggagagcgga ggaggactgg tgcagcctgg aggaagtctg    120

cgactgtcat gcgccgctag cggcttcacc ttcagctcct atgcaatgag ctgggtgcga    180

caggcaccag gcaaggggct ggagtgggtc tccgctatct ccggctctgg aggctctact    240

tactatgcag acagtgtgaa ggggcggttc acaatctcca gagataactc taagaacact    300

ctgtacctgc agatgaactc tctgagagct gaggacaccg cagtgtacta ttgcgccaag    360

ggcaaaaggt actttgatta ttggggacag ggcactatgg tgaccgtctc tagtggagga    420

ggaggaagcg gaggaggagg atccggcgga ggaggcagtc agtcagtgct gacacagcca    480

cctagcgcct ccggaacccc aggacagcgg gtcacaatct cttgtagtgg gggatcaagc    540

gacattggga gcaacaccgt gaattggtat cagcagctgc ctggaacagc tccaaagctg    600

ctgatctact ataacaatca gaggccctcc ggcgtccctg atcgcttctc aggcagcaaa    660
```

-continued

```
tccgggactt ctgcaagtct ggccattagt ggcctgcagt cagaggacga agccgattac    720

tattgtgcta cctgggacga taggatgtac tctcccgtgt tcggcggggg aacaaagctg    780

actgtcctgg agagcaaata tggaccacca tgccctccat gtccttttg ggtcctggtg    840

gtcgtgggag gcgtgctggc atgttattct ctgctggtca cagtggcttt catcatcttc    900

tgggtcaagc gaggccggaa gaaactgctg tacatcttca aacagccttt tatgcgccca    960

gtgcagacaa ctcaggagga agacggctgc tcttgtcggt tccccgagga agaggaaggg   1020

ggatgtgagc tgcgcgtgaa gttttctcga agtgccgatg ctcctgcata tcagcaggga   1080

cagaaccagc tgtacaacga gctgaatctg ggccggagag aggaatacga cgtgctggat   1140

aagaggcgcg gcagagaccc agaaatgggc gggaagccac gacggaaaaa cccccaggag   1200

gggctgtata atgaactgca gaaggacaaa atggccgagg cttacagcga aatcgggatg   1260

aagggagaga gaaggcgcgg aaaaggccac gatggactgt atcagggcct gagcactgcc   1320

accaaggaca cctacgatgc tctgcacatg caggcactgc cacccaggtg a            1371
```

<210> SEQ ID NO 16
<211> LENGTH: 945
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
atgctgctgc tggtgacaag cctgctgctg tgcgaactgc cccatcccgc cttcctgctg     60

attcctgagg tccagctgct ggagagcgga ggaggactgg tgcagcctgg aggaagtctg    120

cgactgtcat gcgccgctag cggcttcacc ttcagctcct atgcaatgag ctgggtgcga    180

caggcaccag gcaaggggct ggagtgggtc tccgctatct ccggctctgg aggctctact    240

tactatgcag acagtgtgaa ggggcggttc acaatctcca gagataactc taagaacact    300

ctgtacctgc agatgaactc tctgagagct gaggacaccg cagtgtacta ttgcgccaag    360

ggcaaaaggt actttgatta ttggggacag ggcactatgg tgaccgtctc tagtggagga    420

ggaggaagcg gaggaggagg atccggcgga ggaggcagtc agtcagtgct gacacagcca    480

cctagcgcct ccggaacccc aggacagcgg gtcacaatct cttgtagtgg gggatcaagc    540

gacattggga gcaacaccgt gaattggtat cagcagctgc ctggaacagc tccaaagctg    600

ctgatctact ataacaatca gaggccctcc ggcgtccctg atcgcttctc aggcagcaaa    660

tccgggactt ctgcaagtct ggccattagt ggcctgcagt cagaggacga agccgattac    720

tattgtgcta cctgggacga taggatgtac tctcccgtgt tcggcggggg aacaaagctg    780

actgtcctgg agagcaaata tggaccacca tgccctccat gtccttttg ggtcctggtg    840

gtcgtgggag gcgtgctggc atgttactcc ctgctggtca ctgtggcctt catcatcttc    900

tgggtgcggg tgaagttttc tcgcagtgcc gacgctcccg catga                    945
```

<210> SEQ ID NO 17
<211> LENGTH: 1368
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
atgctgctgc tggtgacaag cctgctgctg tgcgaactgc cccatcccgc cttcctgctg     60
```

```
attcctgagg tccagctgct ggagagcgga ggaggactgg tgcagcctgg aggaagtctg    120
cgactgtcat gcgccgctag cggcttcacc ttcagctcct atgcaatgag ctgggtgcga    180
caggcaccag gcaaggggct ggagtgggtc tccgctatct ccggctctgg aggctctact    240
tactatgcag acagtgtgaa ggggcggttc acaatctcca gagataactc taagaacact    300
ctgtacctgc agatgaactc tctgagagct gaggacaccg cagtgtacta ttgcgccaag    360
ggcaaaaggt actttgatta ttggggacag ggcactatgg tgaccgtctc tagtggagga    420
ggaggaagcg gaggaggagg atccggcgga ggaggcagtc agtcagtgct gacacagcca    480
cctagcgcct ccggaacccc aggacagcgg gtcacaatct cttgtagtgg gggatcaagc    540
gacattggga gcaacaccgt gaattggtat cagcagctgc ctggaacagc tccaaagctg    600
ctgatctact ataacaatca gaggccctcc ggcgtccctg atcgcttctc aggcagcaaa    660
tccgggactt ctgcaagtct ggccattagt ggcctgcagt cagaggacga agccgattac    720
tattgtgcta cctgggacga taggatgtac tctcccgtgt tcggcggggg aacaaagctg    780
actgtcctgg agagcaaata tggaccacca tgccctccat gtcctttttg ggtcctggtg    840
gtcgtgggag gcgtgctggc atgttattcc ctgctggtca cagtggcctt catcatcttc    900
tgggtgcgga gcaagcggag ccggctgctg cactctgact acatgaacat gacccccccgg   960
agacccggcc ctacaagaaa gcattatcag ccttacgccc cacccaggga cttcgcagct   1020
tatcgctccc gagtgaaatt ttctcgcagt gcagatgccc ccgcttatca gcagggccag   1080
aatcagctgt acaacgagct gaatctgggg aggcgcgagg aatacgacgt gctggataag   1140
cgacggggcc gggaccccga aatgggagga aagcctagaa ggaaaaaccc acaggagggc   1200
ctgtataatg aactgcagaa ggacaaaatg gcagaggcct acagcgaaat cggaatgaag   1260
ggagagcgcc gacggggcaa aggacacgat ggcctgtatc aggggctgag caccgccaca   1320
aaggacacct acgatgccct gcacatgcag gctctgcctc cacgctga                1368
```

```
<210> SEQ ID NO 18
<211> LENGTH: 1494
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
```

```
atgctgctgc tggtgacaag cctgctgctg tgcgaactgc cccatcccgc cttcctgctg     60
attcctgagg tccagctgct ggagagcgga ggaggactgg tgcagcctgg aggaagtctg    120
cgactgtcat gcgccgctag cggcttcacc ttcagctcct atgcaatgag ctgggtgcga    180
caggcaccag gcaaggggct ggagtgggtc tccgctatct ccggctctgg aggctctact    240
tactatgcag acagtgtgaa ggggcggttc acaatctcca gagataactc taagaacact    300
ctgtacctgc agatgaactc tctgagagct gaggacaccg cagtgtacta ttgcgccaag    360
ggcaaaaggt actttgatta ttggggacag ggcactatgg tgaccgtctc tagtggagga    420
ggaggaagcg gaggaggagg atccggcgga ggaggcagtc agtcagtgct gacacagcca    480
cctagcgcct ccggaacccc aggacagcgg gtcacaatct cttgtagtgg gggatcaagc    540
gacattggga gcaacaccgt gaattggtat cagcagctgc ctggaacagc tccaaagctg    600
ctgatctact ataacaatca gaggccctcc ggcgtccctg atcgcttctc aggcagcaaa    660
tccgggactt ctgcaagtct ggccattagt ggcctgcagt cagaggacga agccgattac    720
```

```
tattgtgcta cctgggacga taggatgtac tctcccgtgt tcggcggggg aacaaagctg    780

actgtcctgg agagcaaata tggaccacca tgccctccat gtcctttttg ggtcctggtg    840

gtcgtgggag gcgtgctggc atgttattcc ctgctggtca ctgtggcctt catcatcttc    900

tgggtgcgga gcaagcggag ccggctgctg cactctgact acatgaacat gactccacgg    960

agacccggcc ctacccggaa acattatcag ccctacgccc cacccagaga ttttgccgct   1020

tataggtcca agcgcggccg aaagaaactg ctgtacatct tcaaacagcc cttcatgaga   1080

cccgtccaga caactcagga ggaagacggc tgcagctgta ggttccccga ggaagaggaa   1140

gggggatgtg agctgagggt gaagttttct cgcagtgcag atgcccctgc ttatcagcag   1200

ggacagaatc agctgtacaa cgagctgaat ctgggcaggc gcgaggaata cgacgtgctg   1260

gataagcgac ggggcagaga ccccgaaatg ggagggaagc ccagaaggaa aaaccctcag   1320

gaggggctgt ataatgaact gcagaaggac aaaatggcag aggcctacag tgaaatcggg   1380

atgaagggag agcgccgacg gggaaaaggc cacgatggac tgtatcaggg cctgtctact   1440

gccaccaagg acacctacga tgccctgcac atgcaggctc tgcctccacg ctga         1494
```

```
<210> SEQ ID NO 19
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Leu Leu Leu Val Thr Ser Leu Leu Leu Cys Glu Leu Pro His Pro
1               5                   10                  15

Ala Phe Leu Leu Ile Pro Asp Val Val Met Thr Gln Ser Pro Leu Ser
            20                  25                  30

Leu Pro Val Thr Pro Gly Glu Pro Ala Ser Ile Ser Cys Arg Ser Ser
        35                  40                  45

Gln Ser Leu Val His Ser Asn Arg Asn Thr Tyr Leu His Trp Tyr Leu
    50                  55                  60

Gln Lys Pro Gly Gln Ser Pro Gln Leu Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Ser Gln Asn Thr His Val Pro Pro Thr Phe Gly Gln Gly
        115                 120                 125

Thr Lys Leu Glu Ile Lys Gly Gly Gly Gly Ser Gly Gly Gly Gly Ser
    130                 135                 140

Gly Gly Gly Gly Ser Gln Val Gln Leu Val Gln Ser Gly Ala Glu Val
145                 150                 155                 160

Lys Lys Pro Gly Ala Ser Val Lys Val Ser Cys Lys Ala Ser Gly Tyr
                165                 170                 175

Thr Phe Thr Asp Tyr Glu Met His Trp Val Arg Gln Ala Pro Gly Gln
            180                 185                 190

Gly Leu Glu Trp Met Gly Ala Leu Asp Pro Lys Thr Gly Asp Thr Ala
        195                 200                 205

Tyr Ser Gln Lys Phe Lys Gly Arg Val Thr Leu Thr Ala Asp Lys Ser
    210                 215                 220
```

```
Thr Ser Thr Ala Tyr Met Glu Leu Ser Ser Leu Thr Ser Glu Asp Thr
225                 230                 235                 240

Ala Val Tyr Tyr Cys Thr Arg Phe Tyr Ser Tyr Thr Tyr Trp Gly Gln
                245                 250                 255

Gly Thr Leu Val Thr Val Ser Ser Asp Lys Thr His Thr Cys Pro Pro
            260                 265                 270

Cys Pro Phe Trp Val Leu Val Val Val Gly Gly Val Leu Ala Cys Tyr
        275                 280                 285

Ser Leu Leu Val Thr Val Ala Phe Ile Ile Phe Trp Val Lys Arg Gly
    290                 295                 300

Arg Lys Lys Leu Leu Tyr Ile Phe Lys Gln Pro Phe Met Arg Pro Val
305                 310                 315                 320

Gln Thr Thr Gln Glu Glu Asp Gly Cys Ser Cys Arg Phe Pro Glu Glu
                325                 330                 335

Glu Glu Gly Gly Cys Glu Leu Arg Val Lys Phe Ser Arg Ser Ala Asp
            340                 345                 350

Ala Pro Ala Tyr Gln Gln Gly Gln Asn Gln Leu Tyr Asn Glu Leu Asn
        355                 360                 365

Leu Gly Arg Arg Glu Glu Tyr Asp Val Leu Asp Lys Arg Arg Gly Arg
    370                 375                 380

Asp Pro Glu Met Gly Gly Lys Pro Gln Arg Arg Lys Asn Pro Gln Glu
385                 390                 395                 400

Gly Leu Tyr Asn Glu Leu Gln Lys Asp Lys Met Ala Glu Ala Tyr Ser
                405                 410                 415

Glu Ile Gly Met Lys Gly Glu Arg Arg Arg Gly Lys Gly His Asp Gly
            420                 425                 430

Leu Tyr Gln Gly Leu Ser Thr Ala Thr Lys Asp Thr Tyr Asp Ala Leu
        435                 440                 445

His Met Gln Ala Leu Pro Pro Arg
    450                 455


<210> SEQ ID NO 20
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Leu Leu Leu Val Thr Ser Leu Leu Leu Cys Glu Leu Pro His Pro
1               5                   10                  15

Ala Phe Leu Leu Ile Pro Asp Val Val Met Thr Gln Ser Pro Leu Ser
            20                  25                  30

Leu Pro Val Thr Pro Gly Glu Pro Ala Ser Ile Ser Cys Arg Ser Ser
        35                  40                  45

Gln Ser Leu Val His Ser Asn Arg Asn Thr Tyr Leu His Trp Tyr Leu
    50                  55                  60

Gln Lys Pro Gly Gln Ser Pro Gln Leu Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Ser Gln Asn Thr His Val Pro Pro Thr Phe Gly Gln Gly
```

-continued

```
        115                 120                 125

Thr Lys Leu Glu Ile Lys Gly Gly Gly Gly Ser Gly Gly Gly Ser
    130                 135                 140

Gly Gly Gly Gly Ser Gln Val Gln Leu Val Gln Ser Gly Ala Glu Val
145                 150                 155                 160

Lys Lys Pro Gly Ala Ser Val Lys Val Ser Cys Lys Ala Ser Gly Tyr
                165                 170                 175

Thr Phe Thr Asp Tyr Glu Met His Trp Val Arg Gln Ala Pro Gly Gln
            180                 185                 190

Gly Leu Glu Trp Met Gly Ala Leu Asp Pro Lys Thr Gly Asp Thr Ala
        195                 200                 205

Tyr Ser Gln Lys Phe Lys Gly Arg Val Thr Leu Thr Ala Asp Lys Ser
    210                 215                 220

Thr Ser Thr Ala Tyr Met Glu Leu Ser Ser Leu Thr Ser Glu Asp Thr
225                 230                 235                 240

Ala Val Tyr Tyr Cys Thr Arg Phe Tyr Ser Tyr Thr Tyr Trp Gly Gln
                245                 250                 255

Gly Thr Leu Val Thr Val Ser Ser Asp Lys Thr His Thr Cys Pro Pro
            260                 265                 270

Cys Pro Phe Trp Val Leu Val Val Val Gly Gly Val Leu Ala Cys Tyr
        275                 280                 285

Ser Leu Leu Val Thr Val Ala Phe Ile Ile Phe Trp Val Arg Ser Lys
    290                 295                 300

Arg Ser Arg Leu Leu His Ser Asp Tyr Met Asn Met Thr Pro Arg Arg
305                 310                 315                 320

Pro Gly Pro Thr Arg Lys His Tyr Gln Pro Tyr Ala Pro Pro Arg Asp
                325                 330                 335

Phe Ala Ala Tyr Arg Ser Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
    370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Gln Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg
```

<210> SEQ ID NO 21
<211> LENGTH: 457
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 21

```
Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Tyr Gly Leu His Trp Val Arg Gln Ala Pro Gly
    50                  55                  60

Lys Gly Leu Glu Trp Val Ala Ala Ile Ser Tyr Asp Gly Ser Lys Lys
65                  70                  75                  80

Tyr Tyr Ala Asp Ser Val Lys Gly Arg Leu Thr Ile Ser Arg Asp Asn
                85                  90                  95

Ser Lys Asn Thr Leu Tyr Leu Gln Met Asn Ser Leu Arg Pro Asp Asp
            100                 105                 110

Thr Ala Leu Tyr Phe Cys Ala Arg Gly Trp Phe Val Glu Pro Leu Ser
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Gly Ser Gln Ser Val Leu Thr Gln
145                 150                 155                 160

Pro Pro Ser Ala Ser Gly Thr Pro Gly Gln Arg Val Thr Ile Ser Cys
                165                 170                 175

Ser Gly Ser Ser Ser Asn Ile Gly Ser Asn Thr Val Asn Trp Tyr Gln
            180                 185                 190

Gln Leu Pro Gly Thr Ala Pro Lys Leu Leu Ile Tyr Ser Asn Asn Gln
        195                 200                 205

Arg Pro Ser Gly Val Pro Asp Arg Phe Ser Gly Ser Lys Ser Gly Thr
    210                 215                 220

Ser Ala Ser Leu Ala Ile Ser Gly Leu Gln Ser Glu Asp Glu Ala Asp
225                 230                 235                 240

Tyr Tyr Cys Ala Ala Trp Asp Asp Ser Leu Asn Gly Tyr Val Phe Gly
                245                 250                 255

Thr Gly Thr Lys Leu Thr Val Leu Glu Ser Lys Tyr Gly Pro Pro Cys
            260                 265                 270

Pro Pro Cys Pro Phe Trp Val Leu Val Val Val Gly Gly Val Leu Ala
        275                 280                 285

Cys Tyr Ser Leu Leu Val Thr Val Ala Phe Ile Ile Phe Trp Val Lys
    290                 295                 300

Arg Gly Arg Lys Lys Leu Leu Tyr Ile Phe Lys Gln Pro Phe Met Arg
305                 310                 315                 320

Pro Val Gln Thr Thr Gln Glu Glu Asp Gly Cys Ser Cys Arg Phe Pro
                325                 330                 335

Glu Glu Glu Glu Gly Gly Cys Glu Leu Arg Val Lys Phe Ser Arg Ser
            340                 345                 350

Ala Asp Ala Pro Ala Tyr Gln Gln Gly Gln Asn Gln Leu Tyr Asn Glu
        355                 360                 365

Leu Asn Leu Gly Arg Arg Glu Glu Tyr Asp Val Leu Asp Lys Arg Arg
    370                 375                 380

Gly Arg Asp Pro Glu Met Gly Gly Lys Pro Arg Arg Lys Asn Pro Gln
385                 390                 395                 400
```

Glu Gly Leu Tyr Asn Glu Leu Gln Lys Asp Lys Met Ala Glu Ala Tyr
405 410 415

Ser Glu Ile Gly Met Lys Gly Glu Arg Arg Arg Gly Lys Gly His Asp
420 425 430

Gly Leu Tyr Gln Gly Leu Ser Thr Ala Thr Lys Asp Thr Tyr Asp Ala
435 440 445

Leu His Met Gln Ala Leu Pro Pro Arg
450 455

<210> SEQ ID NO 22
<211> LENGTH: 1371
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22
atgctgctgc tggtgacaag cctgctgctg tgcgaactgc cccatcccgc cttcctgctg 60
attcctgatg tcgtgatgac gcagagccct ctctctcttc ccgttacccc tggtgaaccc 120
gcatcaataa gttgccgctc cagtcaatca cttgtacatt caaatcgcaa tacctacctg 180
cactggtatt tgcagaagcc gggacaatcc cctcaattgt tgatatataa ggtatccaat 240
cgcttttctg gagttcctga tagattcagc ggatccgggt ctggtactga tttcactctg 300
aaaatatcca gggtcgaagc tgaggacgta ggcgtatatt attgctctca gaacacgcat 360
gtcccgccga ctttcggcca gggcactaaa cttgagatca agggtggggg gggcagcggt 420
ggtggaggct ctggtggagg agggagccag gtccaactcg ttcaaagtgg cgcagaggtc 480
aaaaagccag gcgcgagcgt taaagtatca tgtaaggcca gcggttatac tttcactgat 540
tatgaaatgc actgggtgcg acaagccccc gggcaaggtc ttgagtggat gggtgcactt 600
gatccaaaaa ctggggatac tgcctatagc cagaaattca aagggcgcgt cacactcact 660
gccgacaaaa gtacgagcac agcttatatg gaattgagtt cactgacgag cgaggatacg 720
gcagtttatt actgtacgcg cttctactct tacacttatt gggggcaagg cactttggtt 780
actgtgtcct ctgacaagac ccatacgtgt ccaccgtgtc ccttctgggt attggttgtg 840
gtcggcggtg tccttgcttg ttacagcctt ctcgtgacag tcgcattcat aattttttgg 900
gtgaaaagag gtcggaaaaa gttgctgtat attttcaaac aaccctttat gagacctgta 960
caaacgactc aggaagagga tggttgtagt tgcaggtttc cggaggagga ggaaggtggg 1020
tgcgaactgc gggtgaaatt tagtagaagc gctgacgcac cagcttacca acaaggacag 1080
aaccaattgt acaacgagct taacttgggt aggagggagg aatatgatgt actggacaaa 1140
aggcgaggtc gcgatccgga aatgggaggc aagccacagc gccggaaaaa cccgcaggaa 1200
ggcttgtaca acgaacttca gaaagataaa atggcagaag catactccga aatagggatg 1260
aaaggtgaac ggcggcgagg caagggccac gacggtctgt accaagggtt gtcaacggca 1320
actaaagaca cgtatgatgc acttcatatg caagctctgc cacccaggtg a 1371

<210> SEQ ID NO 23
<211> LENGTH: 1494
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23
atgctgctgc tggtgacaag cctgctgctg tgcgaactgc cccatcccgc cttcctgctg 60
attcctgatg tcgtgatgac gcagagccct ctctctcttc ccgttacccc tggtgaaccc 120
gcatcaataa gttgccgctc cagtcaatca cttgtacatt caaatcgcaa tacctacctg 180
cactggtatt tgcagaagcc gggacaatcc cctcaattgt tgatatataa ggtatccaat 240
cgcttttctg gagttcctga tagattcagc ggatccgggt ctggtactga tttcactctg 300
aaaatatcca gggtcgaagc tgaggacgta ggcgtatatt attgctctca gaacacgcat 360
gtcccgccga ctttcggcca gggcactaaa cttgagatca agggtggggg gggcagcggt 420
ggtggaggct ctggtggagg agggagccag gtccaactcg ttcaaagtgg cgcagaggtc 480
aaaaagccag gcgcgagcgt taaagtatca tgtaaggcca gcggttatac tttcactgat 540
tatgaaatgc actgggtgcg acaagccccc gggcaaggtc ttgagtggat gggtgcactt 600
gatccaaaaa ctggggatac tgcctatagc cagaaattca aagggcgcgt cacactcact 660
gccgacaaaa gtacgagcac agcttatatg gaattgagtt cactgacgag cgaggatacg 720
gcagtttatt actgtacgcg cttctactct tacacttatt gggggcaagg cactttggtt 780
actgtgtcct ctgacaagac ccatacgtgt ccaccgtgtc ccttctgggt attggttgtg 840
gtcggcggtg tccttgcttg ttacagcctt ctcgtgacag tcgcattcat aattttttgg 900
gtgcggagca agcggagccg gctgctgcac tctgactaca tgaacatgac tccacggaga 960
cccggcccta cccggaaaca ttatcagccc tacgccccac ccagagattt tgccgcttat 1020
aggtccaaaa gaggtcggaa aaagttgctg tatattttca aacaaccctt tatgagacct 1080
gtacaaacga ctcaggaaga ggatggttgt agttgcaggt ttccggagga ggaggaaggt 1140
gggtgcgaac tgcgggtgaa atttagtaga agcgctgacg caccagctta ccaacaagga 1200
cagaaccaat tgtacaacga gcttaacttg ggtaggaggg aggaatatga tgtactggac 1260
aaaaggcgag gtcgcgatcc ggaaatggga ggcaagccac agcgccggaa aaacccgcag 1320
gaaggcttgt acaacgaact tcagaaagat aaaatggcag aagcatactc cgaaataggg 1380
atgaaaggtg aacggcggcg aggcaagggc cacgacggtc tgtaccaagg gttgtcaacg 1440
gcaactaaag acacgtatga tgcacttcat atgcaagctc tgccacccag gtga 1494

<210> SEQ ID NO 24
<211> LENGTH: 1374
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 24
atgctgctgc tggtgacaag cctgctgctg tgcgaactgc cccatcccgc cttcctgctg 60
attcctcagg tccagcttgt gcaaagcgga ggaggagtgg tacagcctgg ccgctctttg 120
agactgtctt gtgcggccag tggatttaca ttctcttctt atgggttgca ttgggtcaga 180
caagcaccgg gcaaaggatt ggaatgggtc gcggccatta gctatgatgg ctcaaagaaa 240
tattatgccg attccgtaaa agggaggttg acaataagcc gggataacag caagaacact 300
ttgtatcttc agatgaatag cctccgaccg gacgacacgg cactgtattt ttgcgcacgc 360
gggtggtttg tagaacccct gagttgggga caaggtactc ttgtcacggt atcttctggc 420
ggaggtggga gtggtggggg tggcagtggc gggggtgggt cacaaagcgt gcttacacaa 480

-continued

```
cctccttctg cgagcggaac tccgggacaa cgggttacga tttcatgctc cggctcaagt    540

agcaatatag gatcaaatac agtgaattgg tatcaacaac tccctggcac agcgcccaag    600

ctgctgatct actctaataa ccagaggccg agtggtgtgc cagataggtt cagtggctct    660

aaatcaggta ctagcgcgag cctcgccatt tcaggacttc aatcagagga tgaagcggac    720

tactactgtg ccgcgtggga tgattcactt aatggatatg ttttcgggac cggaacaaaa    780

ttgacggtat tggagagcaa atatggacca ccatgccctc catgtccttt ttgggtcctg    840

gtggtcgtgg gaggcgtgct ggcatgttat tctctgctgg tcacagtggc tttcatcatc    900

ttctgggtca agcgaggccg gaagaaactg ctgtacatct tcaaacagcc ttttatgcgc    960

ccagtgcaga caactcagga ggaagacggc tgctcttgtc ggttccccga ggaagaggaa   1020

gggggatgtg agctgcgcgt gaagttttct cgaagtgccg atgctcctgc atatcagcag   1080

ggacagaacc agctgtacaa cgagctgaat ctgggccgga gagaggaata cgacgtgctg   1140

gataagaggc gcggcagaga cccagaaatg ggcgggaagc cacgacggaa aaacccccag   1200

gaggggctgt ataatgaact gcagaaggac aaaatggccg aggcttacag cgaaatcggg   1260

atgaagggag agagaaggcg cggaaaaggc cacgatggac tgtatcaggg cctgagcact   1320

gccaccaagg acacctacga tgctctgcac atgcaggcac tgccacccag gtga         1374
```

```
<210> SEQ ID NO 25
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Leu Leu Leu Val Thr Ser Leu Leu Leu Cys Glu Leu Pro His Pro
1               5                   10                  15

Ala Phe Leu Leu Ile Pro Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ala Ile Ser Gly Ser Gly Gly Ser Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Gly Lys Arg Tyr Phe Asp Tyr Trp
        115                 120                 125

Gly Gln Gly Thr Met Val Thr Val Ser Ser Gly Gly Gly Gly Ser Gly
    130                 135                 140

Gly Gly Gly Ser Gly Gly Gly Gly Ser Ser Tyr Glu Leu Thr Gln Pro
145                 150                 155                 160

Pro Ser Ala Ser Gly Thr Pro Gly Gln Arg Val Thr Ile Ser Cys Ser
                165                 170                 175

Gly Gly Ser Ser Asn Ile Gly Ser Asn Thr Val Asn Trp Phe Arg Gln
            180                 185                 190

Leu Pro Gly Thr Ala Pro Lys Leu Leu Val Tyr Phe Asn Asn Gln Arg
        195                 200                 205
```

```
Pro Ser Gly Val Pro Asp Arg Phe Ser Gly Ser Lys Ser Gly Thr Ser
    210                 215                 220

Ala Ser Leu Ala Ile Gly Gly Leu Gln Ser Asp Asp Glu Ala Asp Tyr
225                 230                 235                 240

Tyr Cys Val Ala Trp Asp Asp Ser Leu Asn Ala Pro Val Phe Gly Gly
                245                 250                 255

Gly Thr Lys Val Thr Val Leu Glu Ser Lys Tyr Gly Pro Pro Cys Pro
            260                 265                 270

Pro Cys Pro Phe Trp Val Leu Val Val Val Gly Gly Val Leu Ala Cys
        275                 280                 285

Tyr Ser Leu Leu Val Thr Val Ala Phe Ile Ile Phe Trp Val Lys Arg
    290                 295                 300

Gly Arg Lys Lys Leu Leu Tyr Ile Phe Lys Gln Pro Phe Met Arg Pro
305                 310                 315                 320

Val Gln Thr Thr Gln Glu Glu Asp Gly Cys Ser Cys Arg Phe Pro Glu
                325                 330                 335

Glu Glu Glu Gly Gly Cys Glu Leu Arg Val Lys Phe Ser Arg Ser Ala
            340                 345                 350

Asp Ala Pro Ala Tyr Gln Gln Gly Gln Asn Gln Leu Tyr Asn Glu Leu
        355                 360                 365

Asn Leu Gly Arg Arg Glu Glu Tyr Asp Val Leu Asp Lys Arg Arg Gly
    370                 375                 380

Arg Asp Pro Glu Met Gly Gly Lys Pro Arg Arg Lys Asn Pro Gln Glu
385                 390                 395                 400

Gly Leu Tyr Asn Glu Leu Gln Lys Asp Lys Met Ala Glu Ala Tyr Ser
                405                 410                 415

Glu Ile Gly Met Lys Gly Glu Arg Arg Arg Gly Lys Gly His Asp Gly
            420                 425                 430

Leu Tyr Gln Gly Leu Ser Thr Ala Thr Lys Asp Thr Tyr Asp Ala Leu
        435                 440                 445

His Met Gln Ala Leu Pro Pro Arg
    450                 455
```

<210> SEQ ID NO 26
<211> LENGTH: 1368
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
atgctgctgc tggtgacaag cctgctgctg tgcgaactgc cccatcccgc cttcctgctg      60

attcctgagg tgcagctgtt ggagtctggg ggaggcttgg tacagcctgg ggggtccctg     120

agactctcct gtgcagcctc tggattcacc tttagcagct atgccatgag ctgggtccgc     180

caggctccag ggaaggggct ggagtgggtc tcagctatta gtggtagtgg tggtagcaca     240

tactacgcag actccgtgaa gggccggttc accatctcca gagacaattc caagaacacg     300

ctgtatctgc aaatgaacag cctgagagcc gaggacacgg ccgtgtatta ctgtgcgaga     360

ggaaagcgat actttgacta ctggggccag ggacaatgg tcaccgtctc gagtggtggg     420

gggggcagcg gtggtggagg ctctggtgga ggagggagct cctatgagct gactcagcca     480

ccctcagcgt ctgggacccc cgggcagagg gtcaccatct cttgttctgg aggcagctcc     540

aacatcggaa gtaatactgt aaactggttc cggcagctcc caggaacggc ccccaaactc     600
```

```
ctcgtttatt ttaataatca gcgaccctca ggggtccctg accgattctc tggctccaag    660

tctggcacct cggcctccct ggccatcggt gggctccagt ctgacgatga ggctgactat    720

tactgtgtag catgggatga ctctctgaat gctccggtgt tcggcggagg gaccaaggtc    780

accgtcctag agagcaaata tggaccacca tgccctccat gtcctttttg ggtcctggtg    840

gtcgtgggag gcgtgctggc atgttattct ctgctggtca cagtggcttt catcatcttc    900

tgggtcaagc gaggccggaa gaaactgctg tacatcttca aacagccttt tatgcgccca    960

gtgcagacaa ctcaggagga agacggctgc tcttgtcggt tccccgagga agaggaaggg   1020

ggatgtgagc tgcgcgtgaa gttttctcga agtgccgatg ctcctgcata tcagcaggga   1080

cagaaccagc tgtacaacga gctgaatctg ggccggagag aggaatacga cgtgctggat   1140

aagaggcgcg gcagagaccc agaaatgggc gggaagccac gacggaaaaa cccccaggag   1200

gggctgtata atgaactgca gaaggacaaa atggccgagg cttacagcga aatcgggatg   1260

aagggagaga gaaggcgcgg aaaaggccac gatggactgt atcagggcct gagcactgcc   1320

accaaggaca cctacgatgc tctgcacatg caggcactgc cacccagg                1368
```

<210> SEQ ID NO 27
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Arg Tyr Phe Asp Tyr Trp Gly Gln Gly Thr Met Val
            100                 105                 110

Thr Val Ser Ser
        115
```

<210> SEQ ID NO 28
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Ser Tyr Glu Leu Thr Gln Pro Pro Ser Ala Ser Gly Thr Pro Gly Gln
1               5                   10                  15

Arg Val Thr Ile Ser Cys Ser Gly Gly Ser Ser Asn Ile Gly Ser Asn
            20                  25                  30
```

Thr Val Asn Trp Phe Arg Gln Leu Pro Gly Thr Ala Pro Lys Leu Leu
35 40 45

Val Tyr Phe Asn Asn Gln Arg Pro Ser Gly Val Pro Asp Arg Phe Ser
50 55 60

Gly Ser Lys Ser Gly Thr Ser Ala Ser Leu Ala Ile Gly Gly Leu Gln
65 70 75 80

Ser Asp Asp Glu Ala Asp Tyr Tyr Cys Val Ala Trp Asp Asp Ser Leu
85 90 95

Asn Ala Pro Val Phe Gly Gly Gly Thr Lys Val Thr Val Leu
100 105 110

<210> SEQ ID NO 29
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Lys Arg Tyr Phe Asp Tyr Trp Gly Gln Gly Thr Met Val
100 105 110

Thr Val Ser Ser
115

<210> SEQ ID NO 30
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Gln Ser Val Leu Thr Gln Pro Pro Ser Ala Ser Gly Thr Pro Gly Gln
1 5 10 15

Arg Val Thr Ile Ser Cys Ser Gly Gly Ser Ser Asp Ile Gly Ser Asn
20 25 30

Thr Val Asn Trp Tyr Gln Gln Leu Pro Gly Thr Ala Pro Lys Leu Leu
35 40 45

Ile Tyr Tyr Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Thr Trp Asp Asp Arg Met
85 90 95

Tyr Ser Pro Val Phe Gly Gly Gly Thr Lys Leu Thr Val Leu
100 105 110

<210> SEQ ID NO 31
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Asp Val Val Met Thr Gln Ser Pro Leu Ser Leu Pro Val Thr Pro Gly
1 5 10 15

Glu Pro Ala Ser Ile Ser Cys Arg Ser Ser Gln Ser Leu Val His Ser
20 25 30

Asn Arg Asn Thr Tyr Leu His Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Asn
85 90 95

Thr His Val Pro Pro Thr Phe Gly Gln Gly Thr Lys Leu Glu Ile Lys
100 105 110

Gly Gly Gly Gly Ser Gly Gly Gly Gly Ser Gly Gly Gly Gly Ser Gln
115 120 125

Val Gln Leu Val Gln Ser Gly Ala Glu Val Lys Lys Pro Gly Ala Ser
130 135 140

Val Lys Val Ser Cys Lys Ala Ser Gly Tyr Thr Phe Thr Asp Tyr Glu
145 150 155 160

Met His Trp Val Arg Gln Ala Pro Gly Gln Gly Leu Glu Trp Met Gly
165 170 175

Ala Leu Asp Pro Lys Thr Gly Asp Thr Ala Tyr Ser Gln Lys Phe Lys
180 185 190

Gly Arg Val Thr Leu Thr Ala Asp Lys Ser Thr Ser Thr Ala Tyr Met
195 200 205

Glu Leu Ser Ser Leu Thr Ser Glu Asp Thr Ala Val Tyr Tyr Cys Thr
210 215 220

Arg Phe Tyr Ser Tyr Thr Tyr Trp Gly Gln Gly Thr Leu Val Thr Val
225 230 235 240

Ser Ser

<210> SEQ ID NO 32
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

Gln Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Leu His Trp Val Arg Gln Ala Pro Gly Lys Gly Leu Glu Trp Val

-continued

```
        35                  40                  45

Ala Ala Ile Ser Tyr Asp Gly Ser Lys Lys Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Pro Asp Asp Thr Ala Leu Tyr Phe Cys
                85                  90                  95

Ala Arg Gly Trp Phe Val Glu Pro Leu Ser Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Gln Ser Val Leu Thr Gln Pro Pro Ser Ala Ser Gly
    130                 135                 140

Thr Pro Gly Gln Arg Val Thr Ile Ser Cys Ser Gly Ser Ser Ser Asn
145                 150                 155                 160

Ile Gly Ser Asn Thr Val Asn Trp Tyr Gln Gln Leu Pro Gly Thr Ala
                165                 170                 175

Pro Lys Leu Leu Ile Tyr Ser Asn Asn Gln Arg Pro Ser Gly Val Pro
            180                 185                 190

Asp Arg Phe Ser Gly Ser Lys Ser Gly Thr Ser Ala Ser Leu Ala Ile
        195                 200                 205

Ser Gly Leu Gln Ser Glu Asp Glu Ala Asp Tyr Tyr Cys Ala Ala Trp
    210                 215                 220

Asp Asp Ser Leu Asn Gly Tyr Val Phe Gly Thr Gly Thr Lys Leu Thr
225                 230                 235                 240

Val Leu
```

<210> SEQ ID NO 33
<211> LENGTH: 723
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

```
gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcaaatga acagcctgag agccgaggac acggccgtgt attactgtgc gagaggaaag    300

cgatactttg actactgggg ccaggggaca atggtcaccg tctcgagtgg tggggggggc    360

agcggtggtg gaggctctgg tggaggaggg agctcctatg agctgactca gccaccctca    420

gcgtctggga cccccgggca gagggtcacc atctcttgtt ctggaggcag ctccaacatc    480

ggaagtaata ctgtaaactg gttccggcag ctcccaggaa cggcccccaa actcctcgtt    540

tattttaata atcagcgacc ctcaggggtc cctgaccgat tctctggctc caagtctggc    600

acctcggcct ccctggccat cggtgggctc cagtctgacg atgaggctga ctattactgt    660

gtagcatggg atgactctct gaatgctccg gtgttcggcg gagggaccaa ggtcaccgtc    720

cta                                                                   723
```

<210> SEQ ID NO 34

<211> LENGTH: 723
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 34
gaggtccagc tgctggagag cggaggagga ctggtgcagc ctggaggaag tctgcgactg 60
tcatgcgccg ctagcggctt caccttcagc tcctatgcaa tgagctgggt gcgacaggca 120
ccaggcaagg ggctggagtg ggtctccgct atctccggct ctggaggctc tacttactat 180
gcagacagtg tgaaggggcg gttcacaatc tccagagata actctaagaa cactctgtac 240
ctgcagatga actctctgag agctgaggac accgcagtgt actattgcgc caagggcaaa 300
aggtactttg attattgggg acagggcact atggtgaccg tctctagtgg aggaggagga 360
agcggaggag gaggatccgg cggaggaggc agtcagtcag tgctgacaca gccacctagc 420
gcctccggaa ccccaggaca gcgggtcaca atctcttgta gtgggggatc aagcgacatt 480
gggagcaaca ccgtgaattg gtatcagcag ctgcctggaa cagctccaaa gctgctgatc 540
tactataaca atcagaggcc ctccggcgtc cctgatcgct tctcaggcag caaatccggg 600
acttctgcaa gtctggccat tagtggcctg cagtcagagg acgaagccga ttactattgt 660
gctacctggg acgataggat gtactctccc gtgttcggcg gggaacaaa gctgactgtc 720 ctg 723

<210> SEQ ID NO 35
<211> LENGTH: 726
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 35
gatgtcgtga tgacgcagag ccctctctct cttcccgtta cccctggtga acccgcatca 60
ataagttgcc gctccagtca atcacttgta cattcaaatc gcaataccta cctgcactgg 120
tatttgcaga agccgggaca atcccctcaa ttgttgatat ataaggtatc caatcgcttt 180
tctggagttc ctgatagatt cagcggatcc gggtctggta ctgatttcac tctgaaaata 240
tccagggtcg aagctgagga cgtaggcgta tattattgct ctcagaacac gcatgtcccg 300
ccgactttcg gccagggcac taaacttgag atcaagggtg gggggggcag cggtggtgga 360
ggctctggtg gaggagggag ccaggtccaa ctcgttcaaa gtggcgcaga ggtcaaaaag 420
ccaggcgcga gcgttaaagt atcatgtaag gccagcggtt atactttcac tgattatgaa 480
atgcactggg tgcgacaagc ccccgggcaa ggtcttgagt ggatgggtgc acttgatcca 540
aaaactgggg atactgccta tagccagaaa ttcaaagggc gcgtcacact cactgccgac 600
aaaagtacga gcacagctta tatggaattg agttcactga cgagcgagga tacggcagtt 660
tattactgta cgcgcttcta ctcttacact tattgggggc aaggcacttt ggttactgtg 720
tcctct 726

<210> SEQ ID NO 36
<211> LENGTH: 726
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36
caggtccagc ttgtgcaaag cggaggagga gtggtacagc ctggccgctc tttgagactg 60
tcttgtgcgg ccagtggatt tacattctct tcttatgggt tgcattgggt cagacaagca 120
ccgggcaaag gattggaatg ggtcgcggcc attagctatg atggctcaaa gaaatattat 180
gccgattccg taaaagggag gttgacaata agccgggata acagcaagaa cactttgtat 240
cttcagatga atagcctccg accggacgac acggcactgt atttttgcgc acgcgggtgg 300
tttgtagaac ccctgagttg gggacaaggt actcttgtca cggtatcttc tggcggaggt 360
gggagtggtg ggggtggcag tggcgggggt gggtcacaaa gcgtgcttac acaacctcct 420
tctgcgagcg gaactccggg acaacgggtt acgatttcat gctccggctc aagtagcaat 480
ataggatcaa atacagtgaa ttggtatcaa caactccctg gcacagcgcc caagctgctg 540
atctactcta ataaccagag gccgagtggt gtgccagata ggttcagtgg ctctaaatca 600
ggtactagcg cgagcctcgc catttcagga cttcaatcag aggatgaagc ggactactac 660
tgtgccgcgt gggatgattc acttaatgga tatgttttcg ggaccggaac aaaattgacg 720
gtattg 726

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Gly Phe Thr Phe Ser Ser Tyr Ala Met Ser
1 5 10

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Ala Ile Ser Gly Ser Gly Gly Ser Thr Tyr Tyr Ala Asp Ser Val Lys
1 5 10 15

Gly

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Gly Lys Arg Tyr Phe Asp Tyr
1 5

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Ser Gly Gly Ser Ser Asn Ile Gly Ser Asn Thr Val Asn
1 5 10

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Phe Asn Asn Gln Arg Pro Ser
1 5

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Val Ala Trp Asp Asp Ser Leu Asn Ala Pro Val
1 5 10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Ser Gly Gly Ser Ser Asp Ile Gly Ser Asn Thr Val Asn
1 5 10

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Tyr Asn Asn Gln Arg Pro Ser
1 5

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Ala Thr Trp Asp Asp Arg Met Tyr Ser Pro Val
1 5 10

```
<210> SEQ ID NO 46
<211> LENGTH: 2013
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

atgctgctgc tggtgacaag cctgctgctg tgcgaactgc cccatcccgc cttcctgctg     60

attcctgagg tgcagctgtt ggagtctggg ggaggcttgg tacagcctgg ggggtccctg    120

agactctcct gtgcagcctc tggattcacc tttagcagct atgccatgag ctgggtccgc    180

caggctccag ggaaggggct ggagtgggtc tcagctatta gtggtagtgg tggtagcaca    240

tactacgcag actccgtgaa gggccggttc accatctcca gagacaattc caagaacacg    300

ctgtatctgc aaatgaacag cctgagagcc gaggacacgg ccgtgtatta ctgtgcgaga    360

ggaaagcgat actttgacta ctggggccag ggacaatgg tcaccgtctc gagtggtggg    420

gggggcagcg gtggtggagg ctctggtgga ggagggagct cctatgagct gactcagcca    480

ccctcagcgt ctgggacccc cgggcagagg gtcaccatct cttgttctgg aggcagctcc    540

aacatcggaa gtaatactgt aaactggttc cggcagctcc caggaacggc ccccaaactc    600

ctcgtttatt ttaataatca gcgaccctca ggggtccctg accgattctc tggctccaag    660

tctggcacct cggcctccct ggccatcggt gggctccagt ctgacgatga ggctgactat    720

tactgtgtag catgggatga ctctctgaat gctccggtgt tcggcggagg gaccaaggtc    780

accgtcctag agagcaaata tggaccacca tgccctccat gtccttttg ggtcctggtg    840

gtcgtgggag gcgtgctggc atgttattct ctgctggtca cagtggcttt catcatcttc    900

tgggtcaagc gaggccggaa gaaactgctg tacatcttca aacagccttt tatgcgccca    960

gtgcagacaa ctcaggagga agacggctgc tcttgtcggt tccccgagga agaggaaggg   1020

ggatgtgagc tgcgcgtgaa gttttctcga agtgccgatg ctcctgcata tcagcaggga   1080

cagaaccagc tgtacaacga gctgaatctg ggccggagag aggaatacga cgtgctggat   1140

aagaggcgcg gcagagaccc agaaatgggc gggaagccac gacggaaaaa cccccaggag   1200

gggctgtata atgaactgca gaaggacaaa atggccgagg cttacagcga aatcgggatg   1260

aagggagaga gaaggcgcgg aaaaggccac gatggactgt atcagggcct gagcactgcc   1320

accaaggaca cctacgatgc tctgcacatg caggcactgc cacccagggg tagcggcgag   1380

ggcagaggaa gtcttctaac atgcggtgac gtggaggaga atcccggccc tatgggtcgg   1440

gggctgctca ggggcctgtg gccgctgcac atcgtcctgt ggacgcgtat cgccagcacg   1500

atcccaccgc acgttcagaa gtcggttaat aacgacatga tagtcactga caacaacggt   1560

gcagtcaagt ttccacaact gtgtaaattt tgtgatgtga gattttccac ctgtgacaac   1620

cagaaatcct gcatgagcaa ctgcagcatc acctccatct gtgagaagcc acaggaagtc   1680

tgtgtggctg tatggagaaa gaatgacgag aacataacac tagagacagt ttgccatgac   1740

cccaagctcc cctaccatga ctttattctg gaagatgctg cttctccaaa gtgcattatg   1800

aaggaaaaaa aaaagcctgg tgagactttc ttcatgtgtt cctgtagctc tgatgagtgc   1860

aatgacaaca tcatcttctc agaagaatat aacaccagca atcctgactt gttgctagtc   1920

atatttcaag tgacaggcat cagcctcctg ccaccactgg gagttgccat atctgtcatc   1980

atcatcttct actgctaccg cgttaaccgg cag                                2013
```

<210> SEQ ID NO 47
<211> LENGTH: 671
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

Met Leu Leu Leu Val Thr Ser Leu Leu Leu Cys Glu Leu Pro His Pro
1               5                   10                  15

Ala Phe Leu Leu Ile Pro Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ala Ile Ser Gly Ser Gly Gly Ser Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Gly Lys Arg Tyr Phe Asp Tyr Trp
        115                 120                 125

Gly Gln Gly Thr Met Val Thr Val Ser Ser Gly Gly Gly Gly Ser Gly
    130                 135                 140

Gly Gly Gly Ser Gly Gly Gly Gly Ser Ser Tyr Glu Leu Thr Gln Pro
145                 150                 155                 160

Pro Ser Ala Ser Gly Thr Pro Gly Gln Arg Val Thr Ile Ser Cys Ser
                165                 170                 175

Gly Gly Ser Ser Asn Ile Gly Ser Asn Thr Val Asn Trp Phe Arg Gln
            180                 185                 190

Leu Pro Gly Thr Ala Pro Lys Leu Leu Val Tyr Phe Asn Asn Gln Arg
        195                 200                 205

Pro Ser Gly Val Pro Asp Arg Phe Ser Gly Ser Lys Ser Gly Thr Ser
    210                 215                 220

Ala Ser Leu Ala Ile Gly Gly Leu Gln Ser Asp Asp Glu Ala Asp Tyr
225                 230                 235                 240

Tyr Cys Val Ala Trp Asp Asp Ser Leu Asn Ala Pro Val Phe Gly Gly
                245                 250                 255

Gly Thr Lys Val Thr Val Leu Glu Ser Lys Tyr Gly Pro Pro Cys Pro
            260                 265                 270

Pro Cys Pro Phe Trp Val Leu Val Val Val Gly Gly Val Leu Ala Cys
        275                 280                 285

Tyr Ser Leu Leu Val Thr Val Ala Phe Ile Ile Phe Trp Val Lys Arg
    290                 295                 300

Gly Arg Lys Lys Leu Leu Tyr Ile Phe Lys Gln Pro Phe Met Arg Pro
305                 310                 315                 320

Val Gln Thr Thr Gln Glu Glu Asp Gly Cys Ser Cys Arg Phe Pro Glu
                325                 330                 335

Glu Glu Glu Gly Gly Cys Glu Leu Arg Val Lys Phe Ser Arg Ser Ala
            340                 345                 350

Asp Ala Pro Ala Tyr Gln Gln Gly Gln Asn Gln Leu Tyr Asn Glu Leu
        355                 360                 365

```
Asn Leu Gly Arg Arg Glu Glu Tyr Asp Val Leu Asp Lys Arg Arg Gly
    370                 375                 380

Arg Asp Pro Glu Met Gly Gly Lys Pro Arg Arg Lys Asn Pro Gln Glu
385                 390                 395                 400

Gly Leu Tyr Asn Glu Leu Gln Lys Asp Lys Met Ala Glu Ala Tyr Ser
                405                 410                 415

Glu Ile Gly Met Lys Gly Glu Arg Arg Arg Gly Lys Gly His Asp Gly
            420                 425                 430

Leu Tyr Gln Gly Leu Ser Thr Ala Thr Lys Asp Thr Tyr Asp Ala Leu
        435                 440                 445

His Met Gln Ala Leu Pro Pro Arg Gly Ser Gly Glu Gly Arg Gly Ser
    450                 455                 460

Leu Leu Thr Cys Gly Asp Val Glu Glu Asn Pro Gly Pro Met Gly Arg
465                 470                 475                 480

Gly Leu Leu Arg Gly Leu Trp Pro Leu His Ile Val Leu Trp Thr Arg
                485                 490                 495

Ile Ala Ser Thr Ile Pro Pro His Val Gln Lys Ser Val Asn Asn Asp
            500                 505                 510

Met Ile Val Thr Asp Asn Asn Gly Ala Val Lys Phe Pro Gln Leu Cys
        515                 520                 525

Lys Phe Cys Asp Val Arg Phe Ser Thr Cys Asp Asn Gln Lys Ser Cys
    530                 535                 540

Met Ser Asn Cys Ser Ile Thr Ser Ile Cys Glu Lys Pro Gln Glu Val
545                 550                 555                 560

Cys Val Ala Val Trp Arg Lys Asn Asp Glu Asn Ile Thr Leu Glu Thr
                565                 570                 575

Val Cys His Asp Pro Lys Leu Pro Tyr His Asp Phe Ile Leu Glu Asp
            580                 585                 590

Ala Ala Ser Pro Lys Cys Ile Met Lys Glu Lys Lys Lys Pro Gly Glu
        595                 600                 605

Thr Phe Phe Met Cys Ser Cys Ser Ser Asp Glu Cys Asn Asp Asn Ile
    610                 615                 620

Ile Phe Ser Glu Glu Tyr Asn Thr Ser Asn Pro Asp Leu Leu Leu Val
625                 630                 635                 640

Ile Phe Gln Val Thr Gly Ile Ser Leu Leu Pro Pro Leu Gly Val Ala
                645                 650                 655

Ile Ser Val Ile Ile Ile Phe Tyr Cys Tyr Arg Val Asn Arg Gln
            660                 665                 670
```

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: SITE
<222> LOCATION: (1)..(15)
<223> OTHER INFORMATION: This sequence may encompass 1-3 "Gly Gly Gly Gly Ser" repeating units
<220> FEATURE:
<223> OTHER INFORMATION: See specification as filed for detailed description of substitutions and preferred embodiments -continued

<400> SEQUENCE: 48

```
Gly Gly Gly Gly Ser Gly Gly Gly Gly Ser Gly Gly Gly Gly Ser
1               5                   10                  15
```

COMPOSITIONS AND METHODS OF TREATING CANCER WITH CHIMERIC ANTIGEN RECEPTORS

SEQUENCE LISTING

This application claims benefit under 35 U.S.C. § 119(e) of the following U.S. Provisional Application No. 63/014,831 filed Apr. 24, 2020. Each of the above listed applications is incorporated by reference herein in its entirety for all purposes.

BACKGROUND OF DISCLOSURE

Field of Invention

This disclosure relates to treatment of cancer using chimeric antigen receptor T cells.

Technical Background

1. Chimeric Antigen Receptor T Cell Therapy

Chimeric antigen receptor (CAR) T cell therapy is a specific form of cell-based immunotherapy that uses engineered T cells to fight cancer. In CAR-T cell therapy, T cells are harvested from a patient's blood, engineered ex vivo to express CARs containing both antigen-binding and T cell-activating domains, expanded into a larger population, and administered to the patient. The CAR-T cells act as a living drug, binding to cancer cells and bringing about their destruction. When successful, the effects of CAR-T cell treatment tend to be long lasting, as evidenced by detection of CAR-T cell persistence and expansion in the patients long after clinical remission.

2. CAR Structure and Function

The antigen-binding domain of a CAR is an extracellular region that targets a surface antigen on tumor cells. Appropriate target antigens can be proteins, phosphorylated proteins, peptide-MHC, carbohydrates, or glycolipid molecules. Ideal target antigens are widely expressed on tumor cells to enable targeting of a high percentage of the cancer cells. Ideal candidate target antigens are also minimally expressed on normal tissues, limiting off-tumor, on-target toxicity. The antigen-binding domain of a CAR comprises a targeting moiety, such as an antibody single chain variable fragment (scFv), which is directed against the target antigen.

The T cell-activating domain of a CAR is intracellular and activates the T cell in response to the antigen-binding domain interacting with its target antigen. A T cell activating domain can contain one or more co-stimulatory domains, which are the intracellular domains of known activating T cell receptors. The selection and positioning of costimulatory domains within a CAR construct influence CAR-T cell function and fate, as costimulatory domains have differential impacts on CAR-T cell kinetics, cytotoxic function, and safety profile.

The extracellular antigen-binding and intracellular T cell-activating domains of CARs are linked by a transmembrane domain, hinge, and optionally, a spacer region. The hinge domain is a short peptide fragment that provides conformational freedom to facilitate binding to the target antigen on the tumor cell. It may be used alone or in conjunction with a spacer domain that projects the scFv away from the T cell surface. The optimal length of the spacer depends on the proximity of the binding epitope to the cell surface.

CAR-T therapy against the B-lymphocyte antigen CD19 (Kymriah®, Novartis) has shown promise in pediatric acute lymphocytic leukemia, and CAR-T therapy against B-cell maturation antigen ("bb2121," a Celgene® and Bluebird-bio® collaboration) has shown promise against relapsed/refractory multiple myeloma. More recent data suggest that the CAR approach can be efficacious against solid tumors. A GD2 CAR natural killer T cell (NKT) therapy has shown activity in neuroblastoma (Heczey A, et al. Invariant NKT cells with chimeric antigen receptor provide a novel platform for safe and effective cancer immunotherapy. *Blood;* 124(18):2824-33, 2014), and mesothelin CAR-T with pembrolizumab has demonstrated anti-tumor activity in mesothelioma. However, additional targets for treating solid tumors are needed.

3. Challenges of CAR-T Cell Therapy

Unfortunately, the complexities of CAR-T cell-based therapy can lead to undesirable and unsafe effects. Toxic effects such as neurotoxicity and acute respiratory distress syndrome are potential adverse effects of CAR-T cell therapy and are potentially fatal. Cytokine release syndrome (CRS) is the most common acute toxicity associated with CAR-T cells. CRS occurs when lymphocytes are highly activated and release excessive amounts of inflammatory cytokines. Serum elevations of interleukin 2, interleukin 6, interleukin 1 beta, GM-CSF, and/or C-reactive protein are sometimes observed in patients with CRS when these factors are assayed. CRS is graded in severity and is diagnosed as one of grades 1-4 (mild to severe), with more serious cases clinically characterized by high fever, hypotension, hypoxia, and/or multi-organ toxicity in the patient. One study reported that 92% of acute lymphocytic leukemia patients treated with an anti-CD19 CAR-T cell therapy experienced CRS, and 50% of these patients developed grade 3-4 symptoms (Fitzgerald et al., *Crit Care Med.* 45(2): e124-e131 (2017)).

Another challenge to successful CAR-T cell immunotherapy is immunosuppression caused by characteristics of the tumor microenvironment (TME) of solid tumors. For example, Transforming Growth Factor beta (TGF-β) is a pleiotropic cytokine produced by many cell types in the liver (e.g., liver sinusoidal endothelial cells, Kupffer cells, intrahepatic natural killer (NK) cells, etc.) and in large amounts within cancer microenvironments (Dahmani et al., TGF-β in T Cell Biology: Implications for Cancer Immunotherapy. *Cancers* 2018, 10, 194, 1-21). TGF-β binds to TGFβR2, which recruits and phosphorylates TGFβR1, which once phosphorylated, in turn phosphorylates receptor-regulated SMADs (R-SMADs). The phosphorylated SMADs complex with coSMADs translocate to the nucleus to help regulate gene expression. In the context of T cells, TGF-β signaling suppresses CAR-T cell therapy effectiveness by inhibition of T cell proliferation, activation, and effector functions and by favoring regulatory T-cell differentiation. Therefore, TGF-β-associated immunosuppression is a significant hurdle that must be overcome to obtain effective and persistent CAR-T cell therapy for solid tumors.

4. Armoring

A recent approach to making CAR-T cells that are more resistant to tumor-associated immunosuppression is called "armoring." Armoring is the molecular manipulation of a CAR-T cell to express one or more "armoring molecules" that can counter immunosuppression. For example, investigators recently reported modifying CAR-T cells to secrete PD-1-blocking single-chain variable fragments (scFv), which improved CAR-T cell anti-tumor activity in mouse models of PD-L1$^+$ hematologic and solid tumors (Rafiq, S., Yeku, O., Jackson, H. et al. Targeted delivery of a PD-1-blocking scFv by CAR-T cells enhances anti-tumor efficacy in vivo. *Nat Biotechnol* 36, 847-856 (2018)). Others studies have demonstrated the effectiveness of armoring T cells with a dominant-negative TGF-β receptor type 2 (TGFβRIIDN) armoring molecule to neutralize the suppressive effects of TGF-β on T cells (Bollard et al., Tumor-Specific T-Cells Engineered to Overcome Tumor Immune Evasion Induce Clinical Responses in Patients With Relapsed Hodgkin Lymphoma, *J Clin Oncol* 36(11):1128-1139 (2018)). Currently, at least one clinical study is investigating the effectiveness of armoring anti-PSMA-CAR-T cells with a TGFβRIIDN armoring molecule for treating castrate-resistant prostate cancer (NCT03089203).

Therefore, additional CAR-T cell therapies are needed to augment the armamentarium of effective cancer treatments. Such therapies should include CAR-T cells that effectively treat cancer while minimizing the risk of developing dangerous inflammatory responses, such as CRS. In addition, such therapies should include CAR-T cells that can persist in the immunosuppressive TME of solid tumors.

BRIEF SUMMARY OF THE INVENTION

This disclosure describes compositions and methods for using CAR-T cells to treat cancer. As described below, in a first aspect, an isolated nucleic acid sequence encoding (a) a chimeric antigen receptor (CAR), wherein the CAR comprises an antigen-binding domain specific for a cell surface antigen; and (b) an armoring molecule, wherein the armoring molecule counters immunosuppression of a cell in a tumor microenvironment when expressed on a surface of the cell.

In another aspect, the disclosure describes a cell comprising a nucleic acid sequence encoding a chimeric antigen receptor (CAR), and a TGFβRIIDN armoring molecule expressed on a surface of the cell.

In a further aspect, the disclosure describes a cell, comprising: an anti-GPC3 chimeric antigen receptor (CAR) comprising an antigen binding domain, wherein the antigen binding domain comprises an antibody, Fab, or an scFv comprising a heavy chain variable region (VH) and a light chain variable region (VL), wherein the VH comprises a CDR1 comprising the amino acid sequence of SEQ ID NO: 37, a CDR2 comprising the amino acid sequence of SEQ ID NO: 38, and a CDR3 comprising the amino acid sequence of SEQ ID NO: 39, and wherein the VL comprises a CDR1 comprising the amino acid sequence of SEQ ID NO: 40 or SEQ ID NO: 43, a CDR2 comprising the amino acid sequence of SEQ ID NO: 41 or SEQ ID NO: 44, and a CDR3 comprising the amino acid sequence of SEQ ID NO: 42 or SEQ ID NO: 45; and a TGFβRIIDN armoring molecule.

In yet another aspect, the disclosure describes a method of treating cancer, comprising: administering to a subject in need thereof a cell, wherein the cell comprises (a) an chimeric antigen receptor (CAR) specific for a cell surface antigen, and (b) an armoring molecule, wherein the armoring molecule counters immunosuppression of the cell in a tumor microenvironment of the cancer.

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The accompanying drawings are included to provide a further understanding of the methods and compositions of the disclosure. The drawings illustrate one or more embodiment(s) of the disclosure and together with the description serve to explain the principles and operation of the disclosure.

DETAILED DESCRIPTION

1. Definitions

Figures 1A, 1B, 1C, 1D:
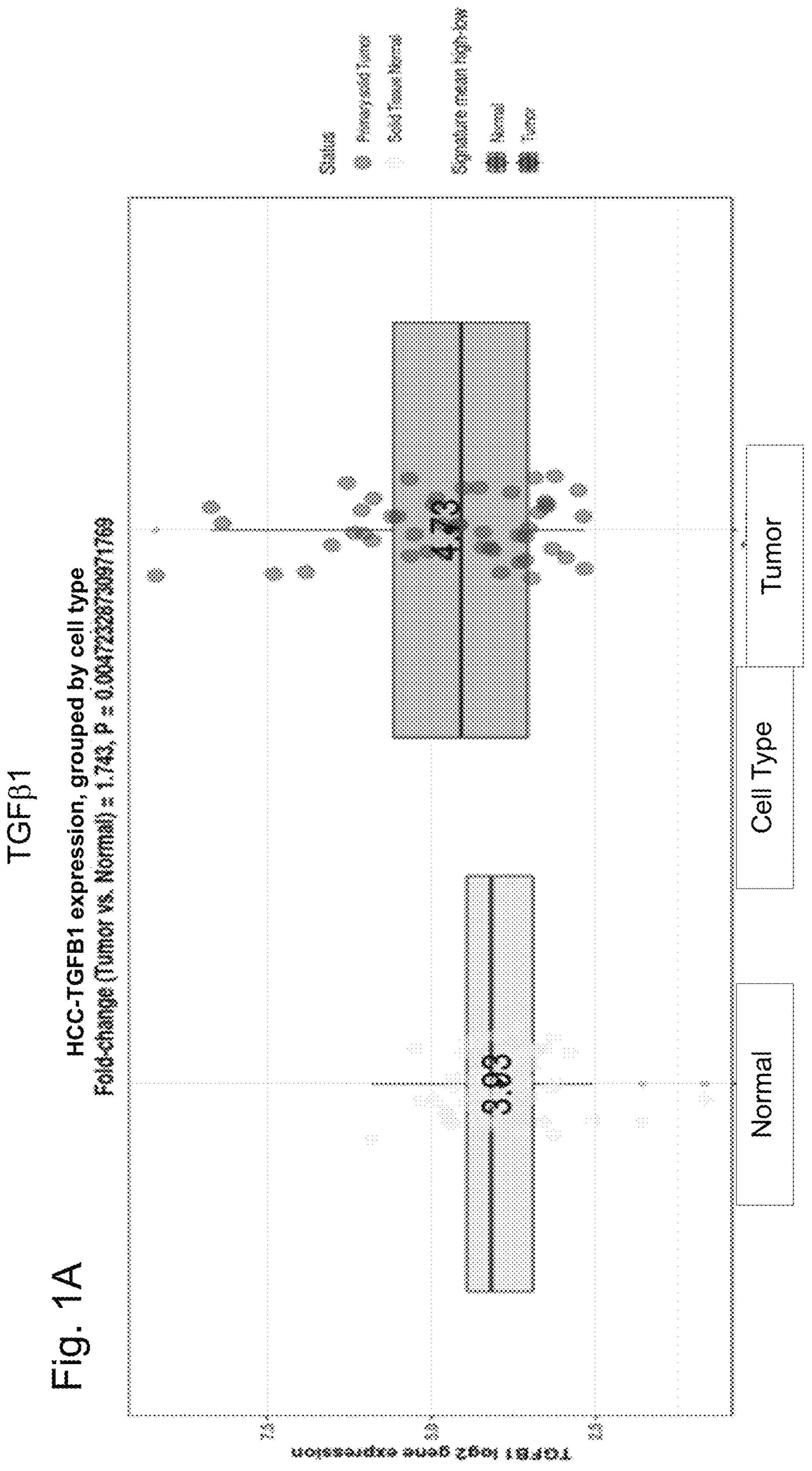
FIGS. 1A-1D. TGFβ1 and TGFβ gene signature and HCC development and survival. 1A. Fold change ($log_2$) of TGFβ1 gene expression in normal solid tissue (left) and primary solid tumor of hepatocellular carcinoma (HCC, right). 1B. Survival curves (OS=overall survival) of TGFβ1 high expression versus TGFβ1 low expression in HCC. 1C. Fold change ($log_2$) of TGFβ signaling in normal solid tissue (left) and solid tumor tissue (right). 1D. Survival curves of TGFβ high signaling versus low signaling.
Figures 1A, 1B, 1C, 1D:
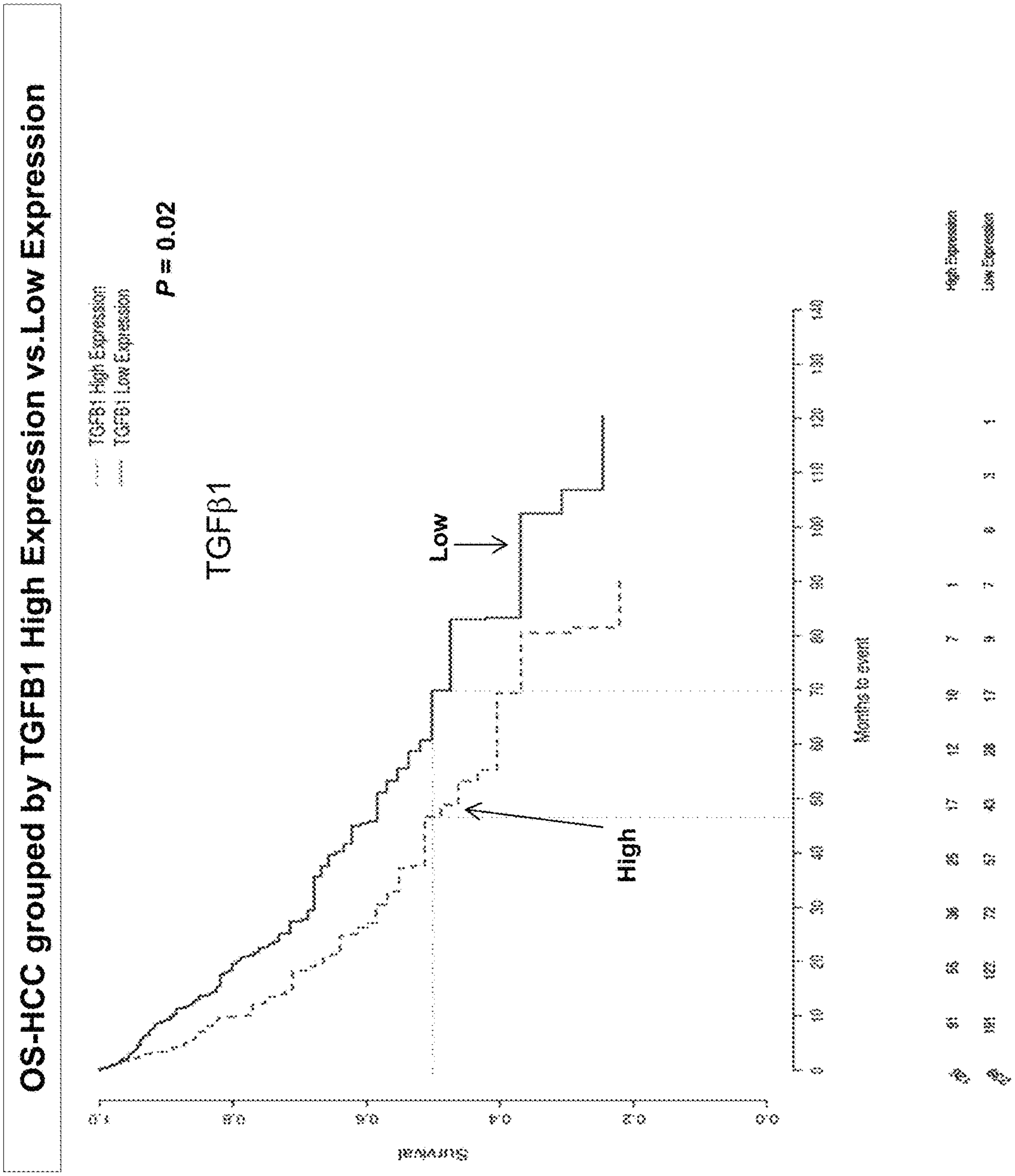
Figures 1A, 1B, 1C, 1D:
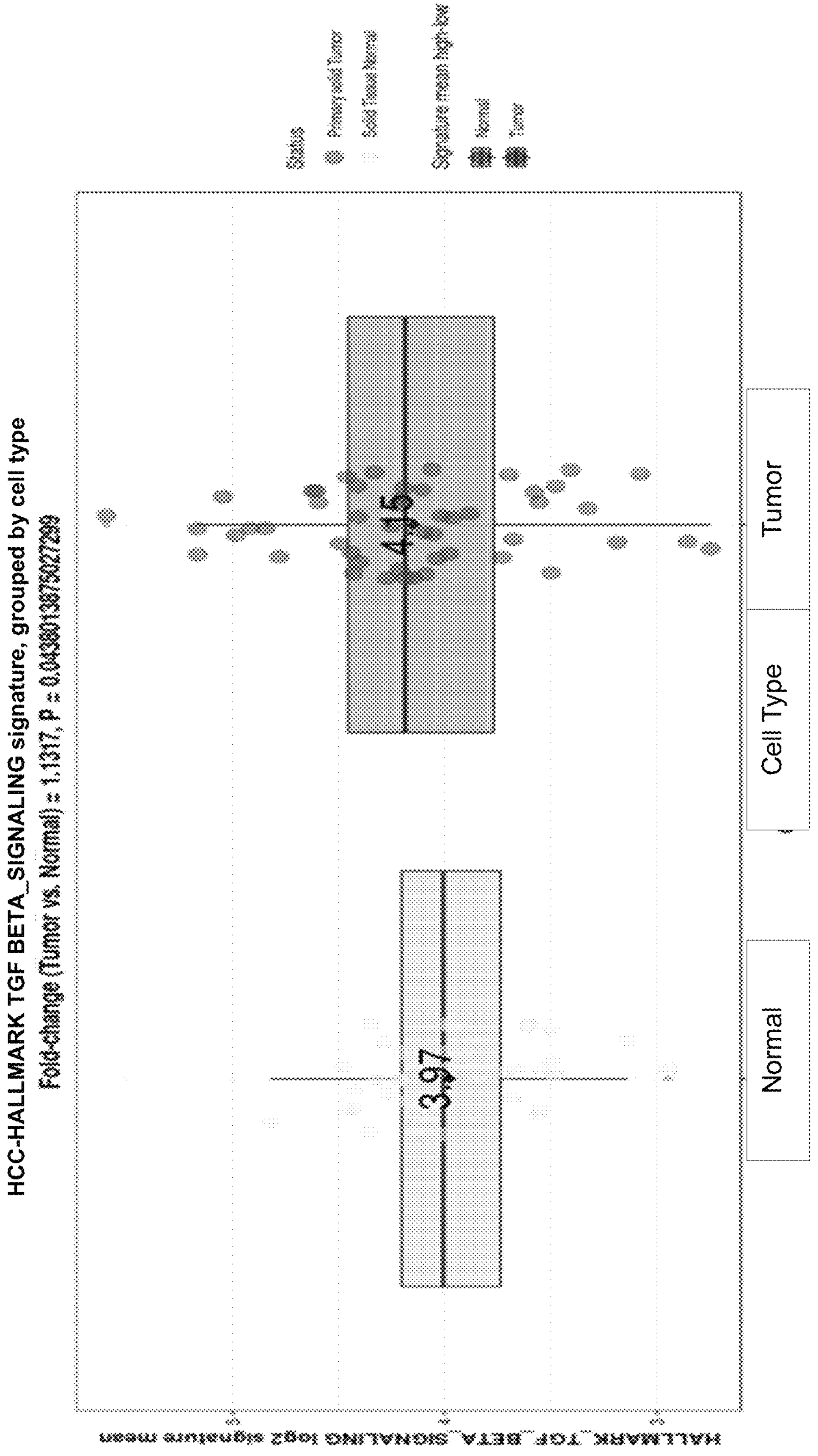
Figures 1A, 1B, 1C, 1D:
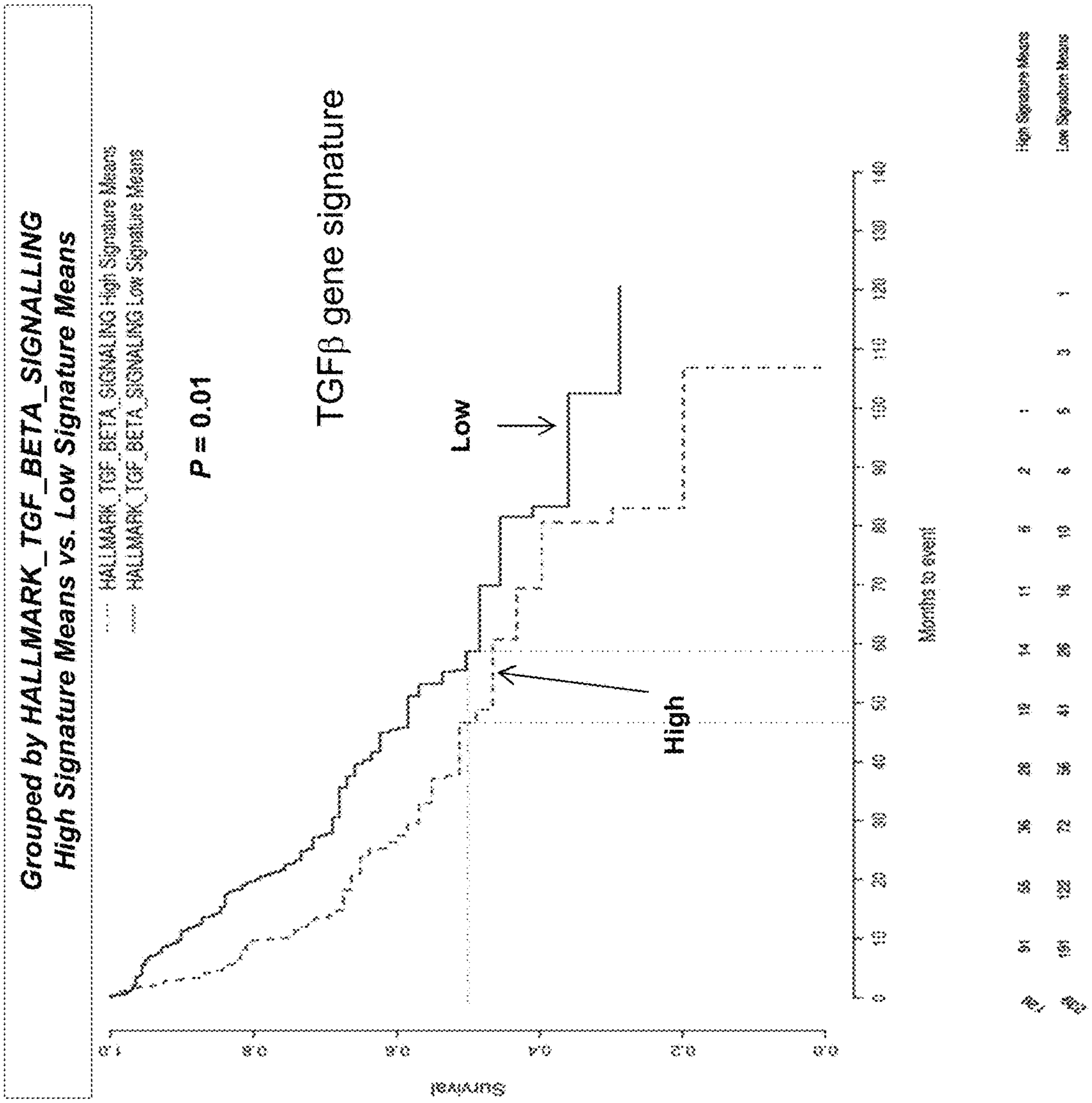

Unless defined otherwise, all technical and scientific terms used herein have the meaning commonly understood by a person skilled in the art to which this invention belongs. The following references provide one of skill with a general definition of many of the terms used in this invention: Singleton, et al., Dictionary of Microbiology and Molecular Biology (2nd ed. 1994); The Cambridge Dictionary of Science and Technology (Walker ed., 1988); The Glossary of Genetics, 5th Ed., R. Rieger, et al. (eds.), Springer Verlag (1991); and Hale & Marham, The Harper Collins Dictionary of Biology (1991). As used herein, the following terms have the meanings ascribed to them below, unless specified otherwise.

As used herein, the terms "comprise" and "include" and variations thereof (e.g., "comprises," "comprising," "includes," and "including") will be understood to indicate the inclusion of a stated component, feature, element, or step or group of components, features, elements or steps but not the exclusion of any other component, feature, element, or step or group of components, features, elements, or steps. Any of the terms "comprising,". "consisting essentially of," and "consisting of" may be replaced with either of the other two terms, while retaining their ordinary meanings.

As used herein, the singular forms "a," "an," and "the" include plural referents unless the context clearly indicates otherwise.

Percentages disclosed herein can vary in amount by ±10, 20, or 30% from values disclosed and remain within the scope of the contemplated disclosure.

Unless otherwise indicated or otherwise evident from the context and understanding of one of ordinary skill in the art, values herein that are expressed as ranges can assume any specific value or sub-range within the stated ranges in different embodiments of the disclosure, to the tenth of the unit of the lower limit of the range, unless the context clearly dictates otherwise.

As used herein, ranges and amounts can be expressed as "about" a particular value or range. The term "about" also includes the exact amount. For example, "about 5%" means "about 5%" and also "5%." The term "about" can also refer to ±10% of a given value or range of values. Therefore, about 5% also means 4.5%-5.5%, for example. Unless otherwise clear from context, all numerical values provided herein are modified by the term "about."

As used herein, the terms "or" and "and/or" can describe multiple components in combination or exclusive of one another. For example, "x, y, and/or z" can refer to "x" alone, "y" alone, "z" alone, "x, y, and z," "(x and y) or z," "x or (y and z)," or "x or y or z."

As used herein, the term "polypeptide" refers to a molecule composed of monomers (amino acids) linearly linked by amide bonds (also known as peptide bonds). The term "polypeptide" refers to any chain or chains of two or more amino acids. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms.

A "protein" as used herein can refer to a single polypeptide, i.e., a single amino acid chain as defined above, but can also refer to two or more polypeptides that are associated, e.g., by disulfide bonds, hydrogen bonds, or hydrophobic interactions, to produce a multimeric protein.

An "isolated" substance, e.g., isolated nucleic acid, is a substance that is not in its natural milieu, though it is not necessarily purified. For example, an isolated nucleic acid is a nucleic acid that is not produced or situated in its native or natural environment, such as a cell. An isolated substance can have been separated, fractionated, or at least partially purified by any suitable technique.

As used herein, the terms "antibody" and "antigen-binding fragment thereof" refer to at least the minimal portion of an antibody which is capable of binding to a specified antigen which the antibody targets, e.g., at least some of the complementarity determining regions (CDRs) of the variable domain of a heavy chain (VH) and the variable domain of a light chain (VL) in the context of a typical antibody produced by a B cell. Antibodies or antigen-binding fragments thereof can be or be derived from polyclonal, monoclonal, human, humanized, or chimeric antibodies, single chain antibodies, epitope-binding fragments, e.g., Fab, Fab' and F(ab')2, Fd, Fvs, single-chain Fvs (scFvs), single-chain antibodies, disulfide-linked Fvs (sdFvs), fragments comprising either a VL or VH domain alone or in conjunction with a portion of the opposite domain (e.g., a whole VL domain and a partial VH domain with one, two, or three CDRs), and fragments produced by a Fab expression library. ScFv molecules are known in the art and are described, e.g., in U.S. Pat. No. 5,892,019. Antibody molecules encompassed by this disclosure can be of or be derived from any type (e.g., IgG, IgE, IgM, IgD, IgA, and IgY), class (e.g., IgG1, IgG2, IgG3, IgG4, IgA1 and IgA2), or subclass of immunoglobulin molecule. The numbering of amino acids in the variable domain, complementarity determining region (CDRs) and framework regions (FR), of an antibody follow, unless otherwise indicated, the Kabat definition as set forth in Kabat et al. Sequences of Proteins of Immunological Interest, 5th Ed. Public Health Service, National Institutes of Health, Bethesda, MD (1991).

As used herein, the term "polynucleotide" includes a singular nucleic acid as well as multiple nucleic acids, and refers to an isolated nucleic acid molecule or construct, e.g., messenger RNA (mRNA) or plasmid DNA (pDNA). The term "nucleic acid" includes any nucleic acid type, such as DNA or RNA.

As used herein, the term "vector" can refer to a nucleic acid molecule as introduced into a host cell, thereby producing a transformed host cell. A vector can include nucleic acid sequences that permits it to replicate in a host cell, such as an origin of replication. A vector can also include one or more selectable marker gene and other genetic elements known in the art. Specific types of vector envisioned here can be associated with or incorporated into viruses to facilitate cell transformation.

A "transformed" cell, or a "host" cell, is a cell into which a nucleic acid molecule has been introduced by molecular biology techniques. All techniques by which a nucleic acid molecule can be introduced into such a cell, including transfection with viral vectors, transformation with plasmid vectors, and introduction of naked DNA by electroporation, lipofection, and particle gun acceleration are contemplated herein.

As used herein, the term "affinity" refers to a measure of the strength of the binding of an antigen or target (such as an epitope) to its cognate binding domain (such as a paratope). As used herein, the term "avidity" refers to the overall stability of the complex between a population of epitopes and paratopes (i.e., antigens and antigen binding domains).

As used herein, the terms "treat," "treatment," or "treatment of" when used in the context of treating cancer refer to reducing disease pathology, reducing or eliminating disease symptoms, promoting increased survival rates, and/or reducing discomfort. For example, treating can refer to the ability of a therapy when administered to a subject, to reduce disease symptoms, signs, or causes. Treating also refers to mitigating or decreasing at least one clinical symptom and/or inhibition or delay in the progression of the condition and/or prevention or delay of the onset of a disease or illness.

As used herein, the terms "subject," "individual," or "patient," refer to any subject, particularly a mammalian subject, for whom diagnosis, prognosis, or therapy is desired. Mammalian subjects include, for example, humans, non-human primates, dogs, cats, guinea pigs, rabbits, rats, mice, horses, cattle, bears, and so on.

As used herein, the term an "effective amount" or a "therapeutically effective amount" of an administered therapeutic substance, such as a CAR-T cell, is an amount sufficient to carry out a specifically stated or intended purpose, such as treating or treatment of cancer. An "effective amount" can be determined empirically in a routine manner in relation to the stated purpose.

2. Overview

The present disclosure is directed to compositions and methods for treating cancer using chimeric antigen receptor (CAR) cell therapy. More particularly, the present disclosure concerns CAR cell therapies in which the transformed cells, such as T cells, express CARs that for example target Glypican-3 (GPC3). The CAR constructs transformed cells expressing the constructs, and the therapies utilizing the transformed cells disclosed herein can provide robust cancer treatments with minimized risk of cytokine release syndrome (CRS) or indiscriminate cytokine release in non-GPC3 expressing cells.

Without wishing to be bound by theory, GPC3 is believed to be a viable cancer target across multiple modalities, including bispecific T cell engagers, CAR cells, as well as monoclonal antibodies and antibody-drug conjugates (ADCs). GPC3, an onco-fetal antigen, is a GPI-linked heparin sulfate proteoglycan. GPC3 stabilizes the Wnt-Fzd interaction, stimulating Wnt signaling. GPC3 competes with Patched for Hh binding, relieving Smoothened inhibition, and inducing GPC3 degradation. Both pathways have been shown to stimulate hepatocellular carcinoma (HCC) growth. And, GPC3 expression levels have been shown to correlate with stage and grade of HCC.

Further, it is believed that GPC3 is a promising target for CAR cell therapy. Therefore, antibodies and CAR constructs derivized from these antibodies have been developed as described herein.

An additional aspect of the present disclosure includes CAR-T cells, such as those targeting GPC3 and others that are armored with TGFβRIIDN to protect the CAR-T cells against TGF-β-associated immunosuppression for example, of solid tumors.

3. CAR Construct Design

CAR constructs of the present disclosure can have several components, many of which can be selected based upon a desired or refined function of the resultant CAR construct. In addition to an antigen-binding domain, CAR constructs can have a spacer domain, a hinge domain, a signal peptide domain, a transmembrane domain, and one or more costimulatory domains. Selection of one component over another (i.e., selection of a specific co-stimulatory domain from one receptor versus a co-stimulatory domain from a different receptor) can influence clinical efficacy and safety profiles.

4. Antigen Binding Domain

Antigen binding domains contemplated herein can include antibodies or one or more antigen-binding fragments thereof. One contemplated CAR construct targeting GPC3 comprises a single chain variable fragment (scFv) containing light and heavy chain variable regions from one or more antibodies specific for GPC3 that are either directly linked together or linked together via a flexible linker (e.g., a repeat of GGGGS having 1, 2, 3 or more repeats (SEQ ID NO: 48)).

The antigen-binding domain of a CAR as disclosed herein can vary in its binding affinity for the target protein. The relationship between binding affinity and efficacy can be more nuanced in the context of CARs as compared with antibodies, for which higher affinity is typically desirable. For example, preclinical studies on a receptor tyrosine kinase-like orphan receptor 1 (ROR1)-CAR derived from a high-affinity scFv (with a dissociation constant of 0.56 nM) resulted in an increased therapeutic index when compared with a lower-affinity variant. Conversely, other examples have been reported that engineering the scFv for lower affinity improves the discrimination among cells with varying antigen density. This could be useful for improving the therapeutic specificity for antigens differentially expressed on tumor versus normal tissues.

A variety of methods can be used to ascertain the binding affinity of the antigen-binding domain. In some embodiments, methodologies that exclude avidity effects can be used. Avidity effects involve multiple antigen-binding sites simultaneously interacting with multiple target epitopes, often in multimerized structures. Thus, avidity functionally represents the accumulated strength of multiple interactions. An example of a methodology that excludes avidity effects is any approach in which one or both of the interacting proteins is monomeric/monovalent since multiple simultaneous interactions are not possible if one or both partners contain only a single interaction site.

5. Spacer Domain

A CAR construct of the present disclosure can have a spacer domain to provide conformational freedom to facilitate binding to the target antigen on the target cell. The optimal length of a spacer domain may depend on the proximity of the binding epitope to the target cell surface. For example, proximal epitopes can require longer spacers and distal epitopes can require shorter ones. Besides promoting binding of the CAR to the target antigen, achieving an optimal distance between a CAR cell and a cancer cell may also help to occlude sterically large inhibitory molecules from the immunological synapse formed between the CAR cell and the target cancer cell. A CAR can have a long spacer, an intermediate spacer, or a shorter spacer. Long spacers can include a CH2CH3 domain (~220 amino acids) of immunoglobulin G1 (IgG1) or IgG4 (either native or with modifications common in therapeutic antibodies, such as a S228P mutation), whereas the CH3 region can be used on its own to construct an intermediate spacer (~120 amino acids). Shorter spacers can be derived from segments (<60 amino acids) of CD28, CD8α, CD3 or CD4. Short spacers can also be derived from the hinge regions of IgG molecules. These hinge regions may be derived from any IgG isotype and may or may not contain mutations common in therapeutic antibodies such as the S228P mutation mentioned above.

6. Hinge Domain

A CAR can also have a hinge domain. The flexible hinge domain is a short peptide fragment that provides conformational freedom to facilitate binding to the target antigen on the tumor cell. It may be used alone or in conjunction with a spacer sequence. The terms "hinge" and "spacer" are often used interchangeably—for example, IgG4 sequences can be considered both "hinge" and "spacer" sequences (i.e., hinge/spacer sequences).

A CAR can further include a sequence comprising a signal peptide. Signal peptides function to prompt a cell to translocate the CAR to the cellular membrane. Examples include an IgG1 heavy chain signal polypeptide, Ig kappa or lambda light chain signal peptides, granulocyte-macrophage colony stimulating factor receptor 2 (GM-CSFR2 or CSFR2) signal peptide, a CD8a signal polypeptide, or a CD33 signal peptide.

7. Transmembrane Domain

A CAR can further include a sequence comprising a transmembrane domain. The transmembrane domain can include a hydrophobic a helix that spans the cell membrane. The properties of the transmembrane domain have not been as meticulously studied as other aspects of CAR constructs, but they can potentially affect CAR expression and association with endogenous membrane proteins. Transmembrane domains can be derived, for example, from CD4, CD8a, or CD28.

8. Costimulatory Domain

A CAR can further include one or more sequences that form a co-stimulatory domain. A co-stimulatory domain is a domain capable of potentiating or modulating the response of immune effector cells. Co-stimulatory domains can include sequences, for example, from one or more of CD3zeta (or CD3z), CD28, 4-1BB, OX-40, ICOS, CD27, GITR, CD2, IL-2Rβ and MyD88/CD40. The choice of co-stimulatory domain influences the phenotype and metabolic signature of CAR cells. For example, CD28 co-stimulation yields a potent, yet short-lived, effector-like phenotype, with high levels of cytolytic capacity, interleukin-2 (IL-2) secretion, and glycolysis. By contrast, T cells modified with CARs bearing 4-1BB costimulatory domains tend to expand and persist longer in vivo, have increased oxidative metabolism, are less prone to exhaustion, and have an increased capacity to generate central memory T cells.

9. Cells

CAR-based cell therapies can be used with a variety of cell types, such as lymphocytes. Particular types of cells that can be used include T cells, Natural Killer (NK) cells, Natural Killer T (NKT) cells, Invariant Natural Killer T (iNKT) cells, alpha beta T cells, gamma delta T cells, viral-specific T (VST) cells, cytotoxic T lymphocytes (CTLs), and regulatory T cells (Tregs). In one embodiment, CAR cells for treating a subject are autologous. In other embodiments, the CAR cells may be from a genetically similar, but non-identical donor (allogeneic).

10. CAR Cell Production

CAR constructs of the present disclosure can include some combination of the modular components described herein. For example, in some embodiments of the present disclosure, a CAR construct comprises a GPC3 scFv antigen-binding domain. In some embodiments, a CAR comprises a GPC3-2 scFv antigen-binding domain. In some embodiments of the present disclosure, a CAR construct comprises a CSFR2 signal peptide. In some embodiments, a CAR construct comprises an IgG4P hinge/spacer domain carrying an S228P mutation. In some embodiments, a CAR construct comprises a CD28 transmembrane.

Different co-stimulatory domains can be utilized is the CAR constructs of the present disclosure. In some embodiments, a CAR construct comprises a co-stimulatory domain from the intracellular domain of CD3z. In some embodiments, a CAR construct comprises a CD28 co-stimulatory domain. In some embodiments, a CAR construct comprises a 4-1BB co-stimulatory domain. In some embodiments, a CAR construct comprises co-stimulatory domains from CD3z and CD28. In some embodiments, a CAR construct comprises co-stimulatory domains from CD3z and 4-1BB. In some embodiments, a CAR construct comprises co-stimulatory domains from all of CD3z, CD28, and 4-1BB. In some embodiments, a CAR construct comprises co-stimulatory domains from ICOS, OX-40, and/or GITR.

11. CAR Construct Assessment

Constructs of the present disclosure were compared and assessed based on safety as well as persistence and establishment of central memory. The lower affinity (high off-rate) scFv, GPC3, was assessed favorably on account of its improved safety. The 4-1BB and CD3z co-stimulatory domains (both in the same construct) were assessed favorably based on their contribution to improved persistence and favorable in vivo phenotype (more central memory).

12. CAR Embodiments

In some embodiments, the present disclosure provides an isolated nucleic acid sequence encoding a chimeric antigen receptor (CAR) that comprises an antigen-binding domain specific for a surface antigen on a tumor cell. In some embodiments, the cell surface antigen is a protein, a phosphorylated protein, a peptide-MHC, a carbohydrate, or a glycolipid molecule.

Examples of contemplated cell surface antigens include CD10, CD16, CD19, CD20, CD22, CD123, CD30, CD34, CD47, CD56, CD80, CD86, CD117, CD133, CD138, CD171, CD37, CD38, CD5, CD7, CD79, 5T4, AFP, AXL, BCMA, B7H3, CDH3, CDH6, CLDN6, CLDN18, CLL-1, CMV, CS1, DLL3, DR5, FBP, GD2, GFRA1, GPA33, GPC3, IL-1-RAP, IL17RA, ITGB7, EBV, ERBB1/EGFR, ERBB2/Her-2, ERBB3, ERBB4, cMet, EGFRvIII, FAP, FOLR1, CEA, CEACAM6, EphA2, HSV-1, HSV-2, HTLV, HPV16-E6, HPV16-E7, IL13Ra2, Igκ chain, LGR5, LMP1, LeY, LRP8, MG7, MR1, NRCAM, PMEL, NKG2D ligand, PRAME, PRLR, PVR, ROR1, ROR2, SSX2, STEAP1, STEAP2, TACI, TIM3, TRBC1, VEGFR-2, EPCAM1, VCAM1, VIPR2, MAGE-A1, MAGE-A3, MAGE-A4, mesothelin (MSLN), MUC1, MUC16, NY-ESO-1, WT1, PDL1, CAIX, CD70, PSMA, and PSCA. Other cell surface antigens are also contemplated herein.

In some embodiments, the present disclosure provides an isolated nucleic acid sequence encoding a chimeric antigen receptor (CAR) that comprises an antigen binding domain specific for glypican 3 (GPC3). The antigen binding domain has an equilibrium dissociation constant ($K_D$) of about 100 nanomolar (nM) or less, and the CAR construct does not induce cytokine production in GPC3-cells. In some embodiments, the antigen-binding domain includes an antibody or antigen-binding fragment thereof. The antigen-binding domain can be a Fab or a single chain variable fragment (scFv). In some embodiments, the antigen-binding domain is an scFv comprising the nucleic acid sequence of SEQ ID NO: 33 or SEQ ID NO: 34.

In some embodiments, the CAR further includes a transmembrane domain, a costimulatory domain, and a signal domain. The transmembrane domain can be a CD28 transmembrane domain. The costimulatory domain can be one or more of CD3zeta (or CD3z), CD28, 4-1BB, OX-40, ICOS, CD27, GITR, CD2, IL-2Rβ and MyD88/CD40 costimulatory domains. In one specific embodiment, the costimulatory domain is one or more of CD28, 4-1BB, and CD3zeta costimulatory domains. The signal domain can be a sequence encoding a CSFR2 signal peptide.

In some embodiments, the isolated nucleic acid sequence can include a hinge/spacer domain. The hinge/spacer domain can be an IgG4P hinge/spacer.

In some specific embodiments, an isolated nucleic acid sequence encoding a chimeric antigen receptor (CAR) can have the sequence of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, or SEQ ID NO: 26.

In other embodiments, the present disclosure provides an anti-GPC3 chimeric antigen receptor (CAR) including an antigen-binding domain. The antigen-binding domain can be an antibody, Fab, or scFv comprising a heavy chain variable region (VH) and a light chain variable region (VL). In some embodiments, the VH can have a CDR1 comprising the amino acid sequence of SEQ ID NO: 37, a CDR2 comprising the amino acid sequence of SEQ ID NO: 38, and a CDR3 comprising the amino acid sequence of SEQ ID NO: 39. In some embodiments, the VL can have a CDR1 comprising the amino acid sequence of SEQ ID NO: 40 or SEQ ID NO: 43, a CDR2 comprising the amino acid sequence of SEQ ID NO: 41 or SEQ ID NO: 44, and a CDR3 comprising the amino acid sequence of SEQ ID NO: 42 or SEQ ID NO: 45.

In some embodiments, the VH can be the amino acid sequence of SEQ ID NO: 27 or SEQ ID NO: 29, and the VL can be the amino acid sequence of SEQ ID NO: 28 or SEQ ID NO: 30. In some embodiments, the CAR further can have a transmembrane domain, a costimulatory domain, and a signal domain.

In some specific embodiments, the anti-GPC3 CAR can have the amino acid sequence of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 25.

In other embodiments, the present disclosure provides a vector comprising a nucleic acid sequence encoding a chimeric antigen receptor (CAR). The nucleic acid sequence can be SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 26, SEQ ID NO: 33, or SEQ ID NO: 34.

In other embodiments, the present disclosure provides a cell comprising a vector having a nucleic acid sequence of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 26, SEQ ID NO: 33, or SEQ ID NO: 34.

In other embodiments, the present disclosure provides a cell having a nucleic acid sequence encoding a chimeric antigen receptor (CAR), wherein the CAR comprises an antigen binding domain specific for glypican 3 (GPC3), wherein the antigen binding domain has an equilibrium dissociation constant ($K_D$) of about 100 nanomolar (nM) or less, and wherein the CAR construct does not induce cytokine production in GPC3-cells. For example, the nucleic acid sequence can be SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 26, SEQ ID NO: 33, or SEQ ID NO: 34.

In other embodiments, the present disclosure provides a cell expressing an anti-GPC3 chimeric antigen receptor (CAR) on an extracellular surface thereof. The CAR can have an antigen-binding domain that can be an antibody, a Fab, or an scFv each having a heavy chain variable region (VH) and a light chain variable region (VL). The VH can include a CDR1 comprising the amino acid sequence of SEQ ID NO: 37, a CDR2 comprising the amino acid sequence of SEQ ID NO: 38, and a CDR3 comprising the amino acid sequence of SEQ ID NO: 39. The VL can include a CDR1 comprising the amino acid sequence of SEQ ID NO: 40 or SEQ ID NO: 43, a CDR2 comprising the amino acid sequence of SEQ ID NO: 41 or SEQ ID NO: 44, and a CDR3 comprising the amino acid sequence of SEQ ID NO: 42 or SEQ ID NO: 45.

In some embodiments, the VH can have the amino acid sequence of SEQ ID NO: 27 or SEQ ID NO: 29. In some embodiments, the VL can have the amino acid sequence of SEQ ID NO: 28 or SEQ ID NO: 30. The CAR can further include a transmembrane domain, a costimulatory domain, and a signal domain. The cell express a CAR having an amino acid sequence of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 25.

In some embodiments, the present disclosure provides a T cell, a Natural Killer (NK) cell, a cytotoxic T lymphocyte (CTL), and/or a regulatory T cell that express a CAR on an extracellular surface thereof, and the CAR can have an amino acid sequence of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 25. Such cells can exhibit an anti-tumor immunity upon contacting a tumor cell expressing GPC3.

13. Treatment of Cancers with CARs

In some embodiments, the present disclosure provides CAR cells for treatment of cancer. The compositions (e.g., antibodies, CAR constructs, and CAR cells) and methods of their use described herein are especially useful for inhibiting neoplastic cell growth or spread. In some aspects, they are particularly useful for inhibiting neoplastic cell growth in which GPC3 plays a role.

Neoplasms treatable by the compositions of the disclosure include solid tumors, for example, those of the liver, lung, or ovary. However, the cancers listed herein are not intended to be limiting. For example, types of cancer that are contemplated for treatment herein include, for example, NSCLC, advanced solid malignancies, biliary tract neoplasms, bladder cancer, colorectal cancer, diffuse large b-cell lymphoma, esophageal neoplasms, esophageal squamous cell carcinoma, extensive stage small cell lung cancer, gastric adenocarcinoma, gastric cancer, gastroesophageal junction cancer, head and neck cancer, head and neck squamous cell carcinoma, hepatocellular carcinoma, Hodgkin lymphoma, lung cancer, melanoma, mesothelioma, metastatic clear cell renal carcinoma, metastatic melanoma, metastatic non-cutaneous melanoma, multiple myeloma, nasopharyngeal neoplasms, non-Hodgkin lymphoma, ovarian cancer, fallopian tube cancer, peritoneal neoplasms, pleural mesothelioma, prostatic neoplasms, recurrent or metastatic PD-L1 positive or negative SCCHN, recurrent squamous cell lung cancer, renal cell cancer, renal cell carcinoma, SCCHN, hypo pharyngeal squamous cell carcinoma, laryngeal squamous cell carcinoma, small cell lung cancer, squamous cell carcinoma of the head and neck, squamous cell lung carcinoma, TNBC, transitional cell carcinoma, unresectable or metastatic melanoma, urothelial cancer, and urothelial carcinoma.

In one embodiment, cancers contemplated for treatment here include any that express GPC3 on the cell surfaces of the cancer cells. In one specific example, cancers contemplated for treatment herein include hepatocellular carcinoma, non-small cell lung cancer, ovarian cancer, and squamous cell lung carcinoma.

14. Armoring

In some embodiments, the present disclosure provides "armored" cells, such as CAR-T cells that have one or more genetic modifications that enhance or optimize cell function by protecting the cell against an environmental insult, such as an immunosuppressive cytokine or an immunosuppressive TME. Genetic modifications include, but are not limited to, enhanced secretion of cytokines, expression of ligands that interact with immune cells such as T cell, macrophages, and regulatory T cells, or an alteration of functional characteristics. One of skill in the art will understand that armoring a cell, such as a T cell, can provide many additional benefits not described herein that allow for T cell survival in the immunosuppressive TME.

In some embodiments, a cell can include a chimeric antigen receptor (CAR) comprising a tumor specific antigen binding domain, wherein the antigen binding domain comprises an antibody, Fab, or an scFv comprising a heavy chain variable region (VH) and a light chain variable region (VL); and a Transforming Growth Factor beta (TGF-β) receptor type 2 dominant negative (TGFβRIIDN) armoring molecule.

In some embodiments, an armored cell can include a nucleic acid sequence encoding a chimeric antigen receptor (CAR), wherein the CAR comprises an antigen binding domain specific for glypican 3 (GPC3), wherein the antigen binding domain has an equilibrium dissociation constant ($K_D$) of about 100 nanomolar (nM) or less, wherein the CAR construct does not induce cytokine production in GPC3- cells, and wherein the cell expresses a TGFβRIIDN armoring molecule.

In some embodiments, an armored cell can include an anti-GPC3 chimeric antigen receptor (CAR) comprising an antigen binding domain, wherein the antigen binding domain comprises an antibody, Fab, or an scFv comprising a heavy chain variable region (VH) and a light chain variable region (VL), wherein the VH comprises a CDR1 comprising the amino acid sequence of SEQ ID NO: 37, a CDR2 comprising the amino acid sequence of SEQ ID NO: 38, and a CDR3 comprising the amino acid sequence of SEQ ID NO: 39, and wherein the VL comprises a CDR1 comprising the amino acid sequence of SEQ ID NO: 40 or SEQ ID NO: 43, a CDR2 comprising the amino acid sequence of SEQ ID NO: 41 or SEQ ID NO: 44, and a CDR3 comprising the amino acid sequence of SEQ ID NO: 42 or SEQ ID NO: 45; and a TGFβRIIDN armoring molecule.

15. Methods of Treatment

CAR-modified cells of the present invention, such as CAR-T cells, may be administered alone or as a pharmaceutical composition with a diluent and/or other components associated with cytokines or cell populations. Briefly, pharmaceutical compositions of the invention can include, for example, CAR-T cells as described herein, with one or more pharmaceutically or physiologically acceptable carrier, diluent, or excipient. Such compositions can comprise buffers such as neutral buffered saline, buffered saline, and the like; sulfates; carbohydrates such as glucose, mannose, sucrose, or dextrans, mannitol; proteins, polypeptides, or amino acids such as glycine; antioxidants; chelating agents such as EDTA or glutathione; adjuvants (e.g., aluminum hydroxide); and preservatives. The pharmaceutical compositions of the invention may be adapted to the treatment (or prophylaxis).

The CAR-modified cells can also be administered in conjunction with one or more additional therapies. In one embodiment, the additional therapies can include anti-cytokine antibodies. For example, one or more anti-TNFα antibodies can be used to attenuate toxicity and promote anti-tumor activity at higher CAR-T doses, which can be associated with CRS-like symptoms and weight loss.

The number of CAR cells administered per dose, the number of doses, and frequency of dosing will depend on various parameters such as the patient's age, weight, clinical assessment, tumor type, tumor burden, and/or other factors, including the judgment of the attending physician. Any acceptable route of administration is contemplated, such as, without limitation, administration intravenous (e.g., intravenous infusion), parenteral, or subcutaneous routes of administration.

In a particular embodiment, a treatment regimen contemplated can include one or more biological components, such as a CAR-T cell and an anticancer antibody and/or a chemotherapeutic component. For example, it is contemplated that a treatment regimen can additionally include an immune checkpoint inhibitor (ICI), such as those that target the PD-1/PD-L1 axis (PDX) and other immune-oncology (IO) treatments, such as immune system agonists.

Contemplated antibodies include an anti-PD-L1 antibody such as durvalumab (MEDI4736), avelumab, atezolizumab, KNO35, an anti-PD-1 antibody such as nivolumab, pembrolizumab, cemiplimab, SHR1210, IBI308, PDR001, Anti-PD-1, BGB-A317, BCD-100, and JS001, and an anti-CTLA4 antibody, such as tremelimumab or ipilimumab. Additional antibodies are also contemplated herein. Any therapeutically effective antibody subparts are also contemplated herein.

Information regarding durvalumab (or fragments thereof) for use in the methods provided herein can be found in U.S. Pat. Nos. 8,779,108; 9,493,565; and 10,400,039 the disclosures of which are incorporated herein by reference in their entirety. In a specific aspect, durvalumab or an antigen-binding fragment thereof for use in the methods provided herein comprises the variable heavy chain and variable light chain CDR sequences of the 2.14H90PT antibody as disclosed in the aforementioned U.S. patents.

Information regarding tremelimumab (or antigen-binding fragments thereof) for use in the methods provided herein can be found in U.S. Pat. No. 6,682,736 (in which tremelimumab is referred to as 11.2.1), the disclosure of which is incorporated herein by reference in its entirety.

Additional therapeutics (chemotherapies or biologics) contemplated herein include without limitation cisplatin/gemcitabine or methotrexate, vinblastine, ADRIAMYCIN™ (doxorubicin), cisplatin (MVAC), carboplatin-based regimen, or single-agent taxane or gemcitabine, temozolomide, or dacarbazine, vinflunine, docetaxel, paclitaxel, nab-paclitaxel, Vemurafenib, Erlotinib, Afatinib, Cetuximab, Bevacizumab, Erlotinib, Gefitinib, and/or Pemetrexed. Further examples include drugs targeting DNA damage repair systems, such as poly (ADP-ribose) polymerase 1 (PARP1) inhibitors and therapeutics inhibiting WEE1 protein kinase activity, ATR protein kinase activity, ATM protein kinase activity, Aurora B protein kinase activity, and DNA-PK activity.

Any therapeutic compositions or methods contemplated herein can be combined with one or more of any of the other therapeutic compositions and methods provided herein.

In some embodiments, the present disclosure provides a method of treating cancer including administering to a subject in need thereof an effective amount of a cell comprising an anti-GPC3 chimeric antigen receptor (CAR) comprising an antigen-binding domain and an armoring molecule that counters immunosuppression of the cell in a tumor microenvironment when expressed on a surface of the cell. In another aspect, the disclosure describes antigen-binding domain can be an antibody, Fab, or scFv comprising a heavy chain variable region (VH) and a light chain variable region (VL). The VH can include a CDR1 comprising the amino acid sequence of SEQ ID NO: 37, a CDR2 comprising the amino acid sequence of SEQ ID NO: 38, and a CDR3 comprising the amino acid sequence of SEQ ID NO: 39. The VL can include a CDR1 comprising the amino acid sequence of SEQ ID NO: 40 or SEQ ID NO: 43, a CDR2 comprising the amino acid sequence of SEQ ID NO: 41 or SEQ ID NO: 44, and a CDR3 comprising the amino acid sequence of SEQ ID NO: 42 or SEQ ID NO: 45. In some embodiments, the method further inhibits tumor growth, induces tumor regression, and/or prolongs survival of the subject.

In some embodiments, the armoring molecule is TGFβRIIDN.

In some embodiments, the cell is an autologous cell. For example, the autologous cell can be selected from the group consisting of a T cell, a Natural Killer (NK) cell, a cytotoxic T lymphocyte (CTL), and a regulatory T cell.

In some embodiments, the cancer treated by the method is a solid tumor. For example, the cancer can be hepatocellular carcinoma, non-small cell lung cancer, ovarian cancer, and/or squamous cell lung carcinoma. In a specific embodiment, the cancer is hepatocellular carcinoma.

It is to be understood that the particular aspects of the specification are described herein are not limited to specific embodiments presented, and can vary. It also will be understood that the terminology used herein is for the purpose of describing particular aspects only and, unless specifically defined herein, is not intended to be limiting. Moreover, particular embodiments disclosed herein can be combined with other embodiments disclosed herein, as would be recognized by a skilled person, without limitation.

EXAMPLES

The Examples that follow are illustrative of specific embodiments of the disclosure, and various uses thereof. They are set forth for explanatory purposes only and should not be construed as limiting the scope of the disclosure in any way. A description of terms is provided in Table 1.

TABLE 1

Description of terms

| Term | Description |
|---|---|
| GPC3-1 | Anti-GPC3 scFv (lower affinity) |
| GPC3-2 | Anti-GPC3 scFv (higher affinity) |
| GPC3-4 | Prior art anti-GPC3 scFv |
| GPC3-3 | Prior art anti-GPC3 scFv |
| BZ | Intracellular domain of CAR with two co-stimulatory domains of 4-1BB and CD3zeta |
| TZ | Intracellular domain of CAR with a truncated CD3zeta signaling domain (acting as a signaling incompetent control) |
| 28Z | Intracellular domain of CAR with two co-stimulatory domains of CD28 and CD3zeta |
| 28BZ | Intracellular domain of CAR with three co-stimulatory domains of CD28, 4-1BB, and CD3zeta |
| TGFβRIIDN | Dominant-negative TGF-β receptor type 2 molecule |
| GPC3-1 BZ | CAR with GPC3 scFv, CSFR2 signal peptide, IgG4P hinge region, and both 4-1BB and CD3z co-stimulatory domains |
| GPC3-2 BZ | CAR with GPC3-2 scFv, CSFR2 signal peptide, IgG4P hinge region, and both 4-1BB and CD3z co-stimulatory domains |
| aCART-T | CAR-T cell with GPC3 scFv, CSFR2 signal peptide, IgG4P hinge region, and both 4-1BB and CD3z co-stimulatory domains and armored with TGFβRIIDN |
| CSFR2 | Signal peptide used in all CAR constructs |
| IgG4P | Hinge sequence used in all CAR constructs |
| Hep3B | Hepatocellular carcinoma model |
| HUH7 | Resistant hepatocellular carcinoma (HCC) model |

Example 1: TGFβ Gene Expression and Signaling in Liver Hepatocellular Carcinoma Summary In the present example, TGFβ1 gene expression and TGFβ signaling were compared in normal liver versus liver hepatocellular carcinoma (LIHC).

Methods

Data from TCGA cohort was used for this analysis. TGFβ1 gene expression and TGFβ signaling signature in normal liver and tumor tissue from TCGA were compared using t-test. TGFβ signaling signature was formed from the mean expression levels of the following genes: TGFBR1, SMAD7, TGFB1, SMURF2, SMLRF1, BMPR2, SKIL, SKI, ACVR1, PMEPA1, NCOR2, SERPINE1, JUNB, SMAD1, SMAD6, PPP1R15A, TGIF1, FURIN, SMAD3, FKBP1A, MAP3K7, BMPR1A, CTNNB1, HIPK2, KLF10, BMP2, ENG, APC, PPM1A, XIAP, CDH1, ID1, LEFTY2, CDKN1C, TRIM33, RAB31, TJP1, SLC20A1, CDK9, ID3, NOG, ARID4B, IFNGR2, ID2, PPP1CA, SPTBN1, WWTR1, BCAR3, THBS1, FNTA, HDAC1, UBE2D3, LTBP2, and RHOA.

Kaplan-Meier analyses of overall survival (OS) were conducted with LIHC data from TCGA. The data were grouped according to high (≥66th) and low (<66th) TGFβ1 gene expression and TGFβ signaling signature. The P values were determined using the log-rank test.

Results

TGFβ1 gene expression was upregulated in primary solid tumor cells (LIHC) 1.74 fold compared to normal tissue. High expression of TGFβ1 in LIHC was associated with decreased OS compared to LIHC expressing low levels of TGFβ1 (median, 47 months and 70 months, respectively). See FIGS. 1A and 1B.

TGFβ gene signaling was increased in primary solid tumors 1.1317 fold compared to normal tissue. High TGFβ signaling in LIHC was associated with decreased cell survival compared to low TGFβ signaling. See FIGS. 1C and 1D.

Conclusion

These results demonstrate a statistically significant correlation between increased TGFβ1 gene expression and TGFβ signaling with decreased overall survival in patients with LIHC. Therefore, greater TGFβ1 gene expression and TGFβ signaling may play a causative role in cancer related mortality.

Example 2: TGF-β and Signaling in Liver Hepatocellular Carcinoma

Summary

In the present example, the expression of TGFβ and the intensity of TGFβ signaling (p-SMAD2) were compared in normal liver versus liver hepatocellular carcinoma (HCC) by immunohistochemistry analysis.

Methods

Three normal liver samples and 32 Hepatocellular carcinoma samples were stained by immunhistochemistry and the intensity scored. TGF-β1 and pSMAD2 immunohistochemistry were performed on the Ventana Discovery platform using anti-TGF-β1 (Abcam) and anti-pSAMD2 (Cell Signaling Technology) antibodies. TGF-β1 and pSMAD2 expression in FFPE normal liver and HCC specimens was scored semi-quantitatively by a pathologist. IHC staining intensity was define as: score 0, negative staining; score 1, minimal staining; score 2, moderate staining; score 3, strong staining.

Results

Figures 2A, 2B:
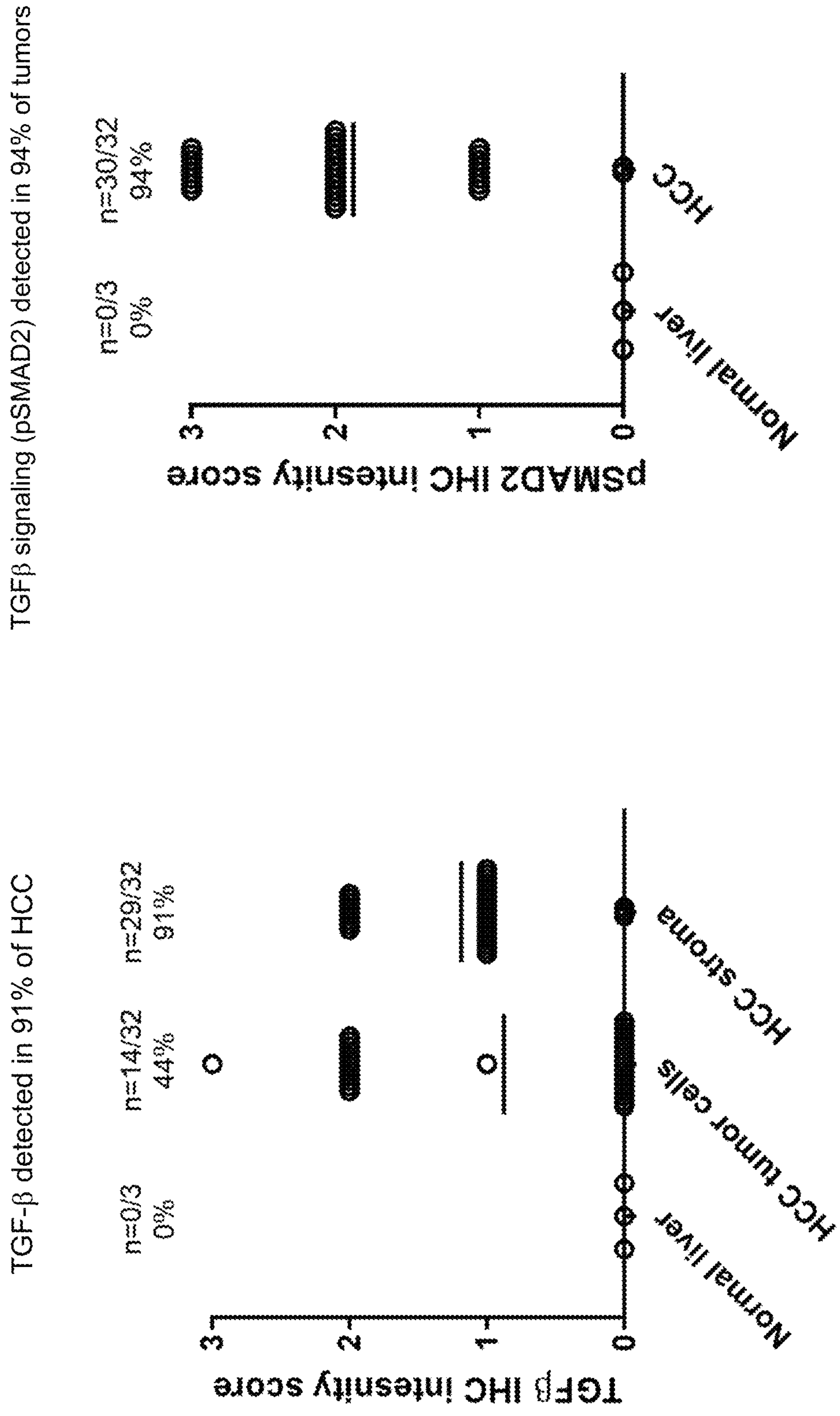
FIGS. 2A and 2B. Human HCC samples are positive for TGFβ and TGFβ signaling. Semi-quantitative pathological assessment of (2A) TGF-b1 and (2B) phosphorylated SMAD2 (pSMAD2) in FFPE normal liver and HCC specimens. Each circle represents the data from one surgical resection. IHC intensity was define as: score 0, negative staining; score 1, minimal staining; score 2, moderate staining; score 3, strong staining.

TGF-β was detected in 44% of tumor and 91% of stroma of HCC samples. TGF-β signaling, judged by the intensity phospo-SMAD2 (p-SMAD2), was tected in 91% of HCC samples. Normal liver was negative for both TGF-β and pSMAD-2 (FIGS. 2A and B).

Conclusions

TGF-β was expressed and actively signaling in the vast majority of HCC samples, demonstrating that it is common immune suppressive factor in HCC tumors and that armoring against it can benefit a large population of HCC patients.

Example 3: Armoring of GPC3 CAR-T Cells with TGFβRIIDN

Summary

Figures 3A, 3B:
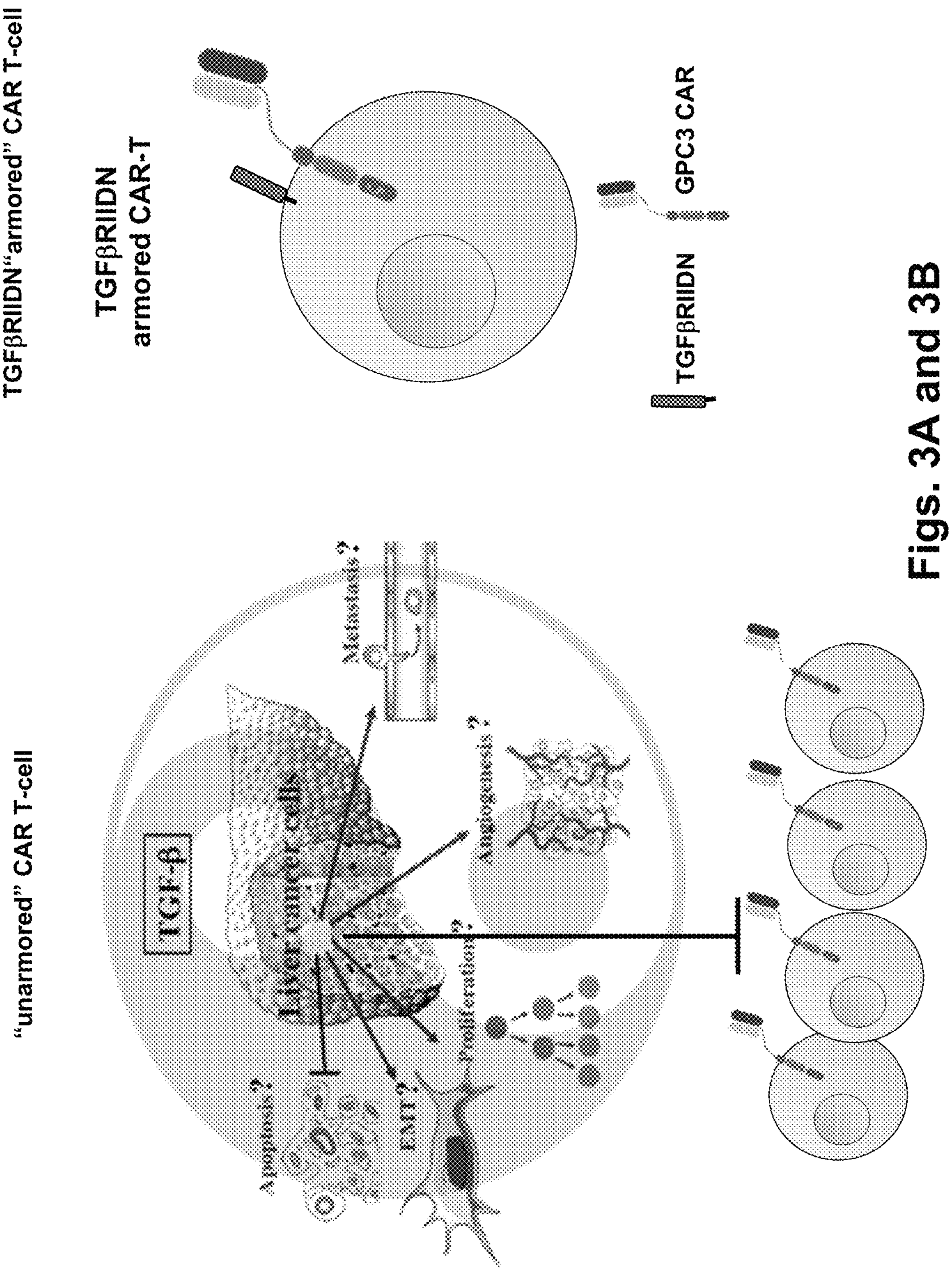
FIGS. 3A and 3B. Armoring of GPC3 CAR-T with TGFβRIIDN. As contemplated herein, it is believed that armoring of GPC3 CAR-T cells with TGFβRIIDN will confer resistance to TGFβ, resulting in improved CAR-T effector function and tumor control. 3A. A schematic of TGF-β-mediated immunosuppression of unarmored CAR-T cells (Figure modified from: Arrese et al, Current Protein & Peptide Science (2018) 19: 1172) 3B. A diagram of an armored CAR-T cell expressing a GPC3 CAR and a TGFβRIIDN armoring molecule. In some embodiments, a CAR and an armoring molecule can be fused, or separated from the CAR by a spacer peptide, at the C terminus.

In the present example, armoring of GPC3 BZ CAR-T cells with TGFβRIIDN was examined as a potential way to protect CAR-T cells against TGFβ-mediated immunosuppression to improve CAR-T cell effector function and tumor control. See FIGS. 3A and 3B.

Methods

TGFβRIIDN: Dominant-negative TGF-β receptor type 2 molecules were prepared by truncating the wild-type receptor at residue 194 so that the TGFβRIIDN receptor lacked an intracellular signaling domain.

Armored CAR-T cells: GPC3 BZ CAR-T cells were armored with TGFβRIIDN by expressing the TGFβRIIDN receptor as a C-terminal fusion to GPC3 BZ CAR with a T2A peptide separating the GPC3 BZ CAR and the TGFβRIIDN receptor.

Figure 4:
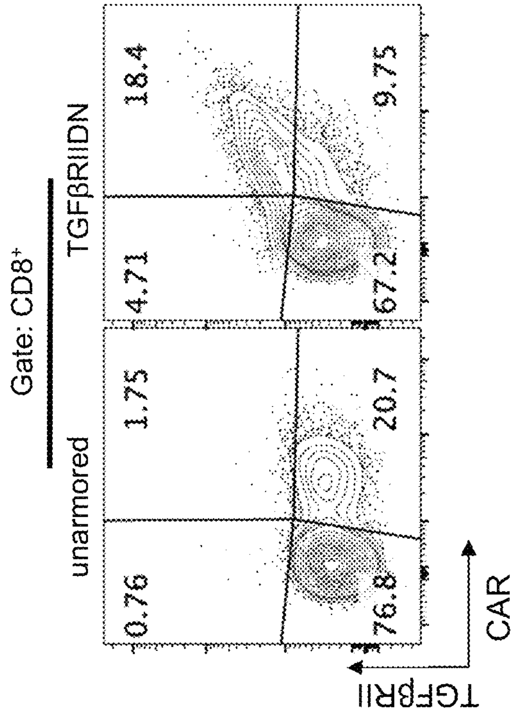
FIG. 4. Expression of TGFβRIIDN. Flow cytometric analysis of TGFβRII and CAR on the surface of unarmored and armored CAR-T cells.

Upon expansion, the expression of CAR and TGFβRII were analyzed on the surface of unarmored and armored CAR-T cells by flow cytometry. CAR expression was detected by using an AF647 anti-idiotypic antibody to the GPC3-CAR (FIG. 4).

Figure 5:
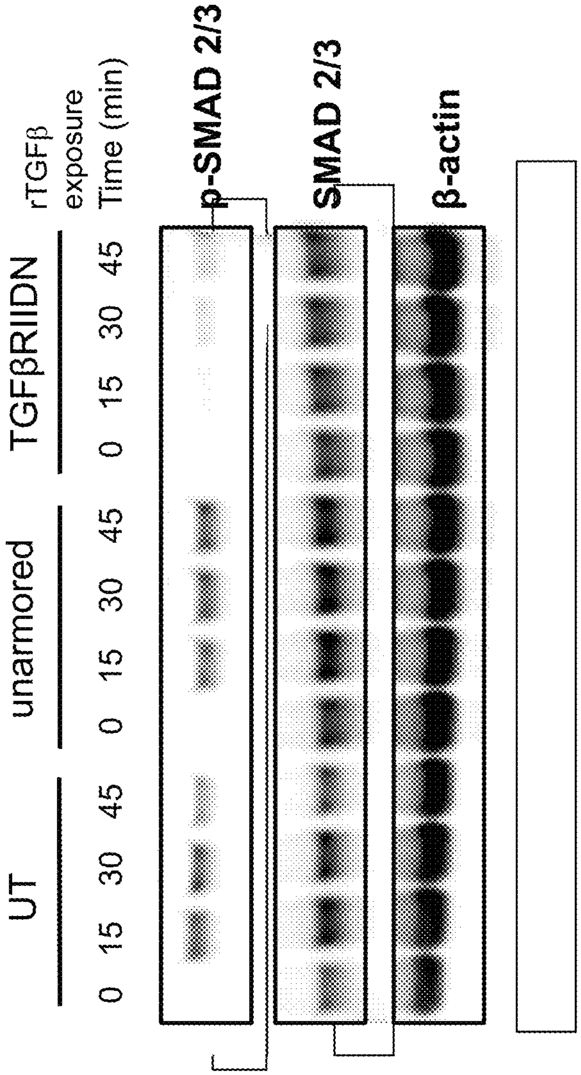
FIG. 5. TGFβRIIDN suppresses TGF-β signaling in CAR-T cells. 4B. Western blot analysis of phosphorylated SMAD2/3 and total SMAD 2/3 in untransduced (UT); unarmored, and armored (TGFβRIIDN) CAR-T cells after 0-45 minutes of rhTGFβ (1 ng/ml) exposure. β-Actin served as a positive loading control for all samples.

CAR-T cells were purified with anti-AF647 microbeads (Miltenyi) after staining with AF647 anti-idiotypic antibody to the GPC3-CAR. Purified cells were expanded for 5 more days, rested for overnight in the absence of IL-2 and serum, and stimulated with recombinant human TGF-β (1 ng/mL) for the indicated time. Cells were lysed in RIPA buffer containing proteases and phosphatases inhibitors and the expression of the indicated proteins analyzed by western blot. (FIG. 5).

Figures 6A, 6B:
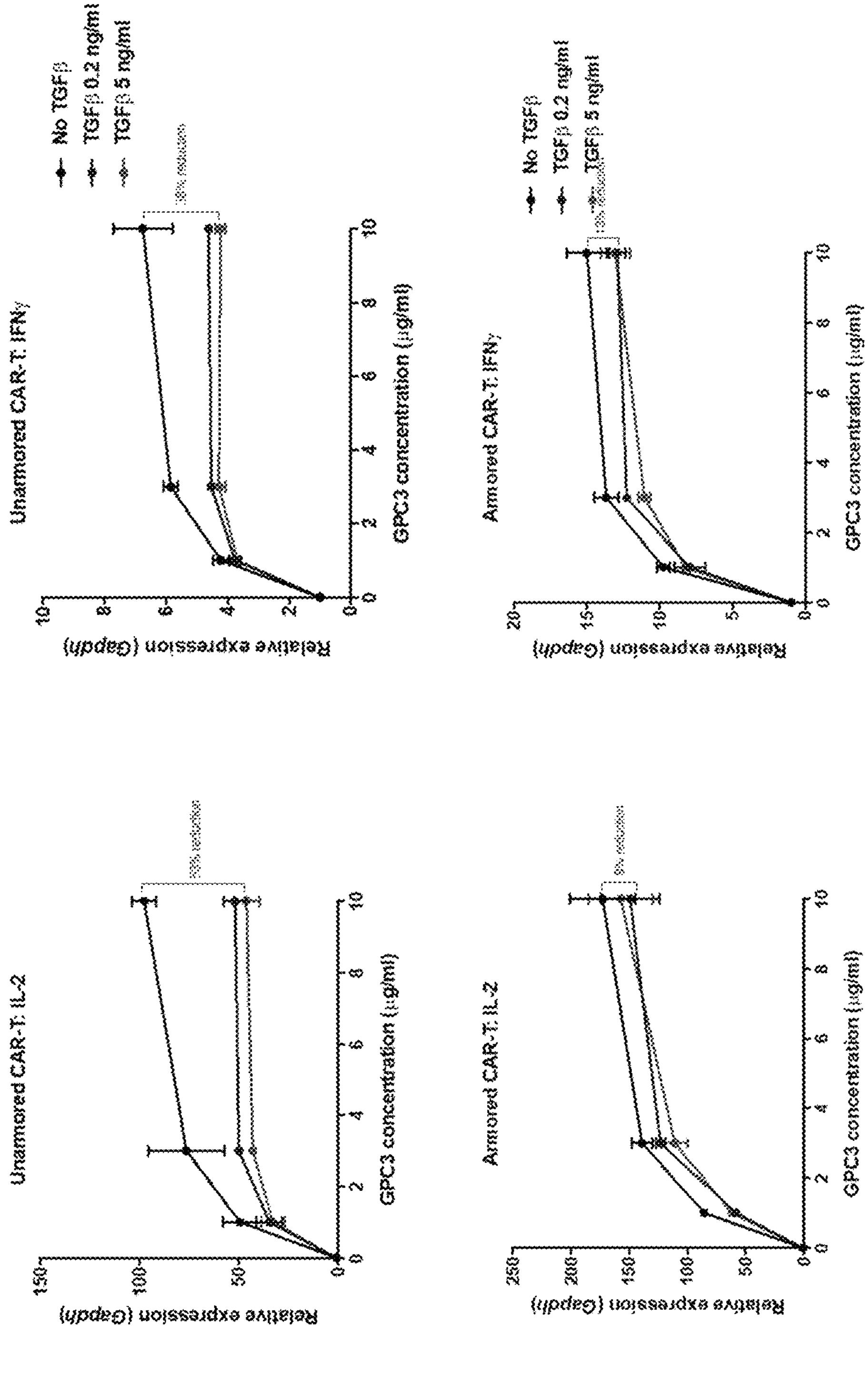
FIGS. 6A and 6B. Expression of TGFβRIIDN prevents TGF-β-induced suppression of effector cytokine transcription. (6A) IL2 and (6B) IFNG mRNA levels in purified TGFβRIIDN and unarmored GPC3 CAR-T cells stimulated for 6 hours with indicated concentration of plate-bound recombinant GPC3 and TGF-β1. Data are pooled from two independent experiments.

Unarmored or armored CAR-T cells were purified with anti-AF647 microbeads (Miltenyi) after staining with AF647 anti-idiotypic antibody to the GPC3-CAR. Purified cells were stimulated with plate-bound recombinant human GPC3 at the indicated concentration in the presence or absence of recombinant human TGF-β (0.2 or 5 ng/mL). After 6 hours cell were harvested, and total RNA was derived from cells using RNeasy Mini Kit (QIAGEN) and reversed transcribed using High Capacity cDNA Reverse Transcription Kit (Applied Biosystems). Quantitative real-time PCR was performed according to the protocol of TaqMan Gene Expression Master Mix (Applied Biosystems) with the following TaqMan primers: GAPDH, Hs02758991_m1; IL2, Hs00174114_m1 and IFNG, Hs00989291_m1. (FIG. 6)

Figures 7A, 7B:
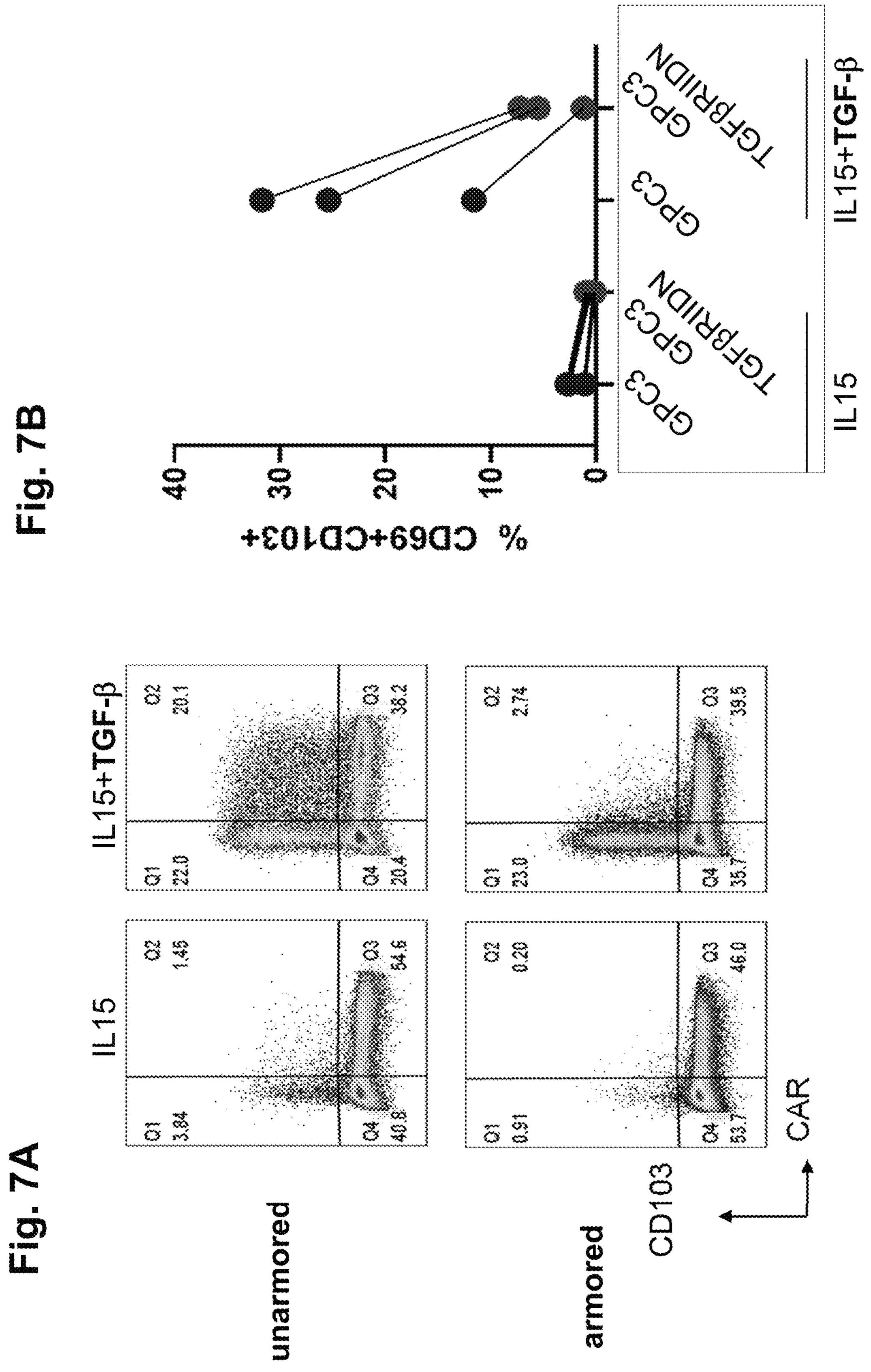
FIGS. 7A and 7B. TGFβRIIDN reduces TGF-β-mediated differentiation of GPC3 CAR-T cells to $T_{RM}$ phenotype. 7A. Flow cytometric analysis of TGF-β-mediated differentiation of GPC3 CAR-T cells to tissue resident memory ($T_{RM}$) cells in the absence (left scatter plots) and presence (right scatter plots) of TGF-β in unarmored (upper scatter plots) and armored (lower scatter plots) GPC3 CAR-T cells. Y-axis=CD103 expression; X-axis=CAR expression. 7B. Percent of $T_{RM}$ cell differentiation as evidenced by CD69+/CD103+ co-expression in unarmored (GPC3) and armored (GPC3 TGFβRIIDN) CAR-T cells treated with TGF-β.

CAR-T cells were stimulated with anti-CD3/CD28 beads (Dynabeads) in the presence of 20 ng/mL of IL-15, without IL-2. After 3 days, TGFβ (50 ng/mL) was added and the cells were assessed for the expression of CD103 by flow cytometry after 3 more days of culture (FIG. 7).

Results

Expression of TGFβRII on the surface of TGFβRIIDN CAR-T. Surface staining of TGFβRII on unarmored and armored CAR-T was evaluated by flow cytometry. The antibody does not distinguish between endogenous and DN TGFβRII since the extracellular portion is the same, but TGFβRIIDN CAR-T co-expressed TGFβRII and CAR, suggesting that the antibody is detecting the overexpressed DN receptor. See FIG. 4.

TGFβRIIDN inhibits SMAD 2/3 phosphorylation in CAR-T cells upon exposure to rhTGFβ: unarmored CAR-T cells demonstrated rhTGF-β-induced SMAD 2/3 phosphorylation similar to untransduced control cells at 0, 15, 30, and 45 minutes post-rhTGF-β exposure. TGF-βRIIDN armored CAR-T cells demonstrated attenuated SMAD 2/3 phosphorylation compared to unarmored CAR-T cells and untransduced control cells at 15, 30, and 45 minutes following rhTGF-β exposure. Total SMAD 2/3 protein and β-actin expression was consistent among all groups. See FIG. 5B.

Expression of TGFβRIIDN prevents TGF-β-mediated decrease of effector cytokine production. Stimulation with recombinant human GPC-3 induced the transcription of the effector cytokines IFN-γ and IL-2 in CAR-T cells. When present during the stimulation, TGF-β decreased the level of IFN-γ and IL-2 produced in unarmored but not in armored CAR-T cells. This result demonstrates that the expression of TGFβRIIDN protects CAR-T cells from the immunosuppressive effect of TGF-β. See FIGS. 6A and 6B.

Expression of TGFβRIIDN efficiently inhibits TGFβ signaling. Differentiation of $CD103^-$ T cells to $CD103^+$ $T_{RM}$ requires IL-15 and TGF-β in vitro. Accordingly, TGFβRIIDN CAR-T cells were not able to differentiate into $T_{RM}$ cells after incubation with TGF-β, as compared to $CAR^-$ cells or unarmored CAR-T cells. This result demonstrates that the expression of the TGFβRIIDN inhibits TGF-β-induced signaling during extended exposure. See FIGS. 7A and 7B.

Conclusion

TGFβRIIDN suppresses TGF-β signaling in armored CAR-T cells, prevents TGF-β mediated decrease of effector cytokine production and mutes TGF-β-mediated differentiation of TGFβRIIDN armored CAR-T cells to a $T_{RM}$ phenotype. Overall these results demonstrate that expression of the dominant negative TGFβRII is sufficient to inhibit TGF-β signaling and its biological effects.

Example 3: TGFβRIIDN Armored CAR-T Cell Cytotoxicity and Expansion During Co-Culture with GPC3+ Cells Summary In the present example, CAR-T cell-mediated cytotoxicity and expansion were compared among UT, unarmored, and TGFβRIIDN-armored CAR-T cells during co-culture with GPC3+ liver cancer cells.

Methods

Figure 8A:
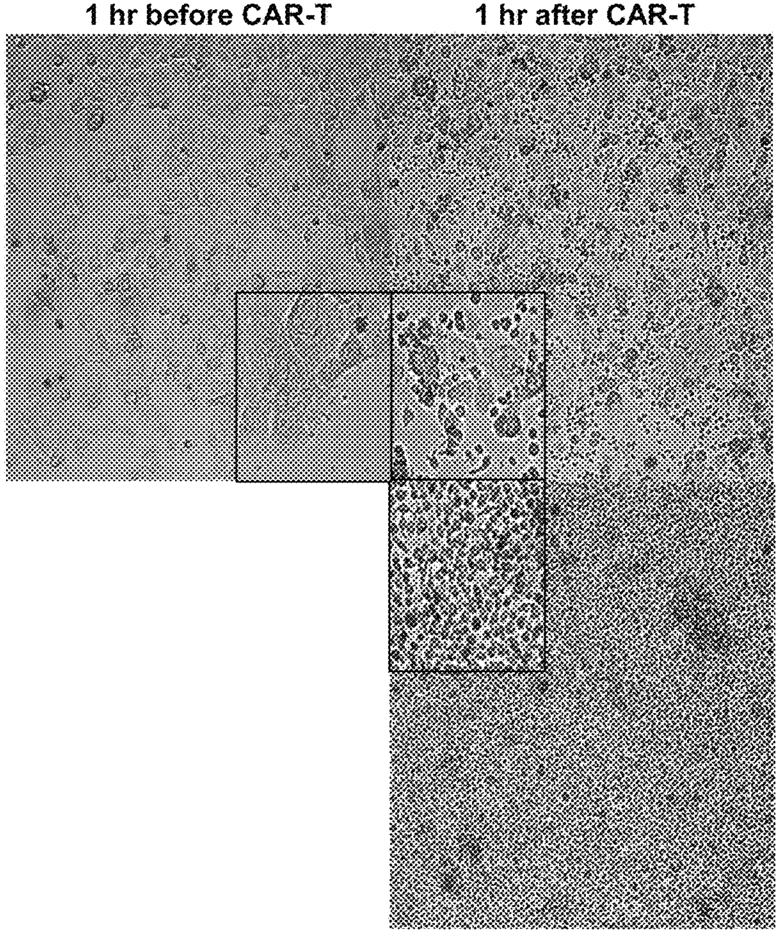
FIGS. 8A, 8B, and 8C. Exploratory in vitro readouts in unarmored and armored CAR-T cells. 8A. Bright field images of real-time monitoring of CAR-T-mediated cytotoxicity during co-culture with GPC3+ tumor cells. Expansion of CAR-T cells was observed visually while in co-culture with GPC3+ tumor cells. 8B. CAR-T-mediated cytotoxicity during co-culture with GPC3+ tumor cells evaluated by xCelligence® real time impedance-based killing assay (RTCA) and expressed as Cell Index. 8C. Quantification of tumor cell (HEP3B or HUH-7 cells)-induced CAR-T cell proliferation in unarmored and armored GPC3 CAR-T cells (AZ: in-house vector backbone; LN: Lentigen vector backbone) in the presence or absence of TGF-β. TGF-β suppresses tumor GPC3-induced proliferation of CAR-T cells after 4 days in co-culture. Armored GPC3 CAR-T cells were not susceptible to suppression.
Figure 8B:
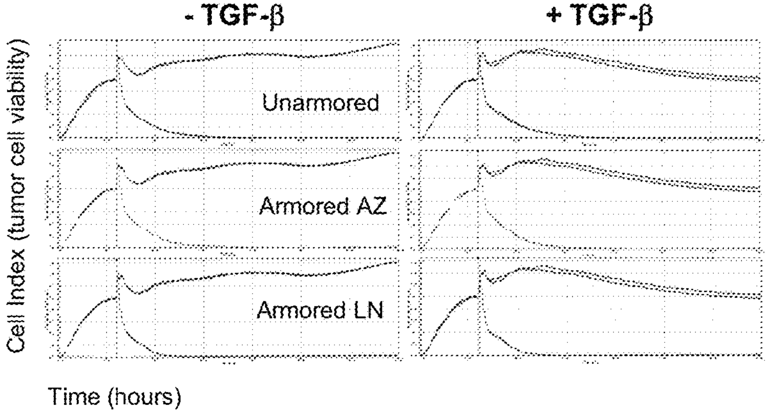
Figure 8C:
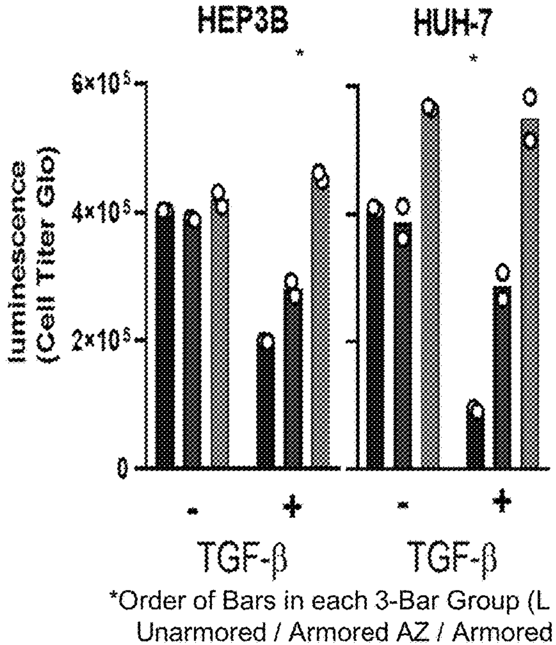

T cells (20,000 CAR+ cells/well) were co-cultured with a squamous cell carcinoma line engineered to express GPC3 (OE21 cells, 10,000 tumor cells per well) for 5 days on an xCELLigence eSight RTCA to simultaneously monitor real-time tumor cell viability by electrical impedance and CAR-T cell density by microscopy (See FIG. 8A). T cells (60,000 CAR+ cells/well) were then co-cultured with Hep3B cells (medium/low GPC3 expression) or Huh7 cells (low GPC3 expression) cells (30,000 tumor cells/well) for 5 days on an xCELLigence RTCA-MP (without microscopy) for 5 days (See FIG. 8B). Non-adherent cells were then removed from the wells and viable CAR-T were quantified using the CellTiter-Glo® Luminescent Cell Viability Assay (Promega, Madison, WI) (See FIG. 8C).

Results

Dramatic expansion of CAR-T cells was observed while in co-culture with GPC3+ tumor cells. See FIG. 8A. All CAR-T cells efficiently killed GPC3+ tumor cells and cytolytic ability was not modulated by TGFβRIIDN co-expression or by addition of exogenous TGF-β. See FIG. 8B. TGF-β suppressed tumor GPC3-induced proliferation of CAR-T cells after 5 days in co-culture. However, TGFβRIIDN armored CAR-T cells were not susceptible to this suppression. See FIG. 8C.

Conclusion

TGFβRIIDN-armored CAR-T cells exhibited significant GPC3+ tumor cell cytotoxicity, indicating that expression of the dominant negative receptor did not affect the ability of CAR-T to kill target cells in vitro. Conversely, unlike unarmored CAR-T cells, TGFβRIIDN armored CAR-T cells were not susceptible to TGF-β-mediated suppression of $GPC3^{+}$-induced proliferation.

Example 4: TGFβRIIDN Armored CAR-T-Cells In Vivo—Xenograft Model

Summary

In the present example, the effectiveness of TGFβRIIDN armored T cells against $GPC3^{+}$ tumor cells was determined in vivo.

Methods

Figure 9:
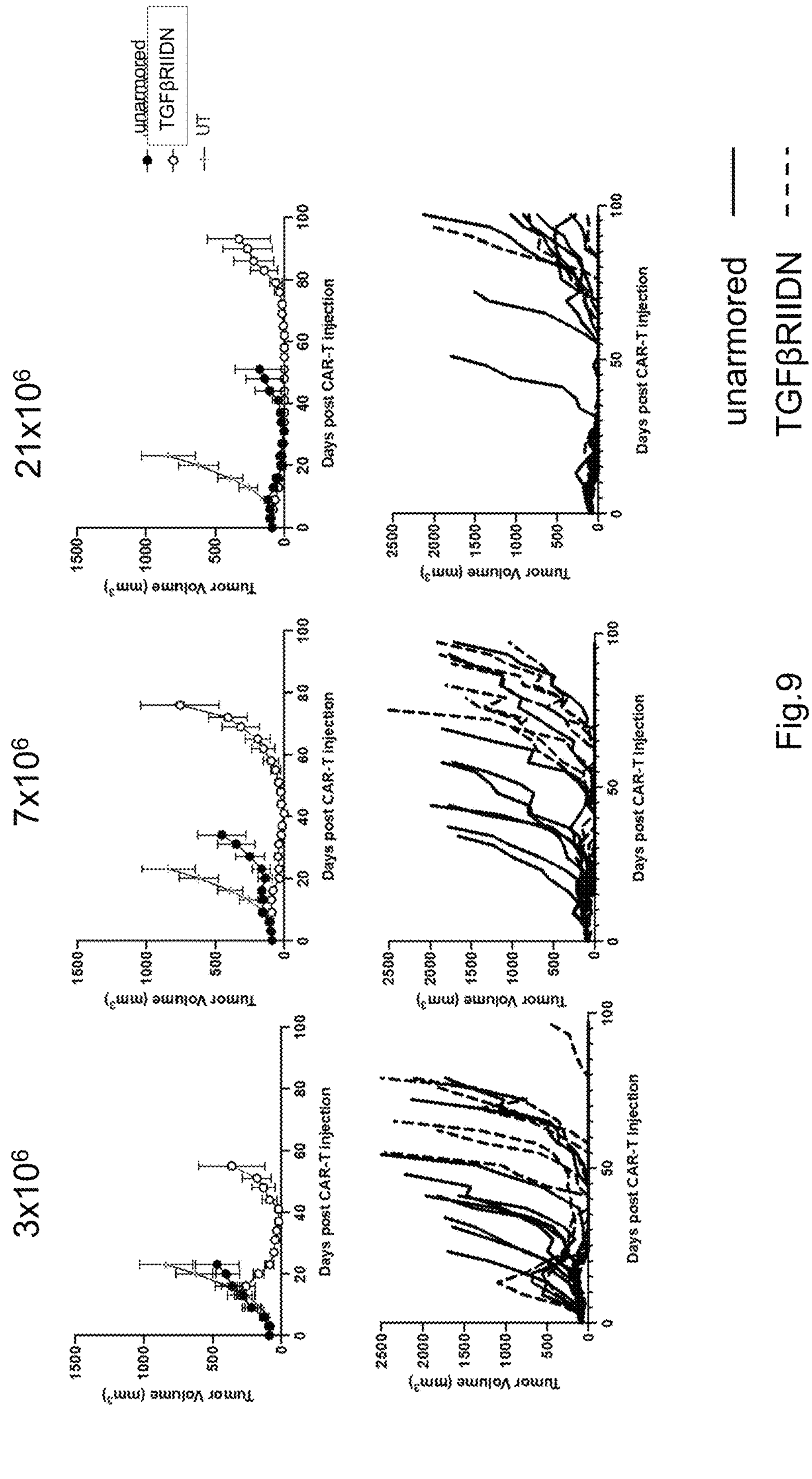
FIG. 9. TGFβRIIDN-armored CAR-T cells and in vivo reduction of tumor volume in xenograft model. Huh7-TGF-β over-expressing xenograft model. Untransduced T cells, unarmored or TGFβRIIDN-armored GPC3 CAR-T cells were infused in mice bearing Huh7 tumors engineered to over-express TGF-β. Tumor volume was measured by weekly (10 mice/group).

The hepatocellular carcinoma Huh7-TGF-β model, which overexpresses TGF-β was used to test the in vivo effectiveness of TGFβRIIDN-armored T cells in reducing tumor volume. Tumor cells were implanted in the flank of NSG mice (10 mice/group). When tumors reached an average volume of 150 $mm^3$, mice were dosed with 3, 7, or $21\times10^6$ of the indicated CAR-T or 21 million of untransduced T cells and tumors measured bi-weekly. Upper graphs: average tumor volume per group. Lower graphs: tumor volume for each individual mouse at the indicated dose (See FIG. 9).

Figure 10:
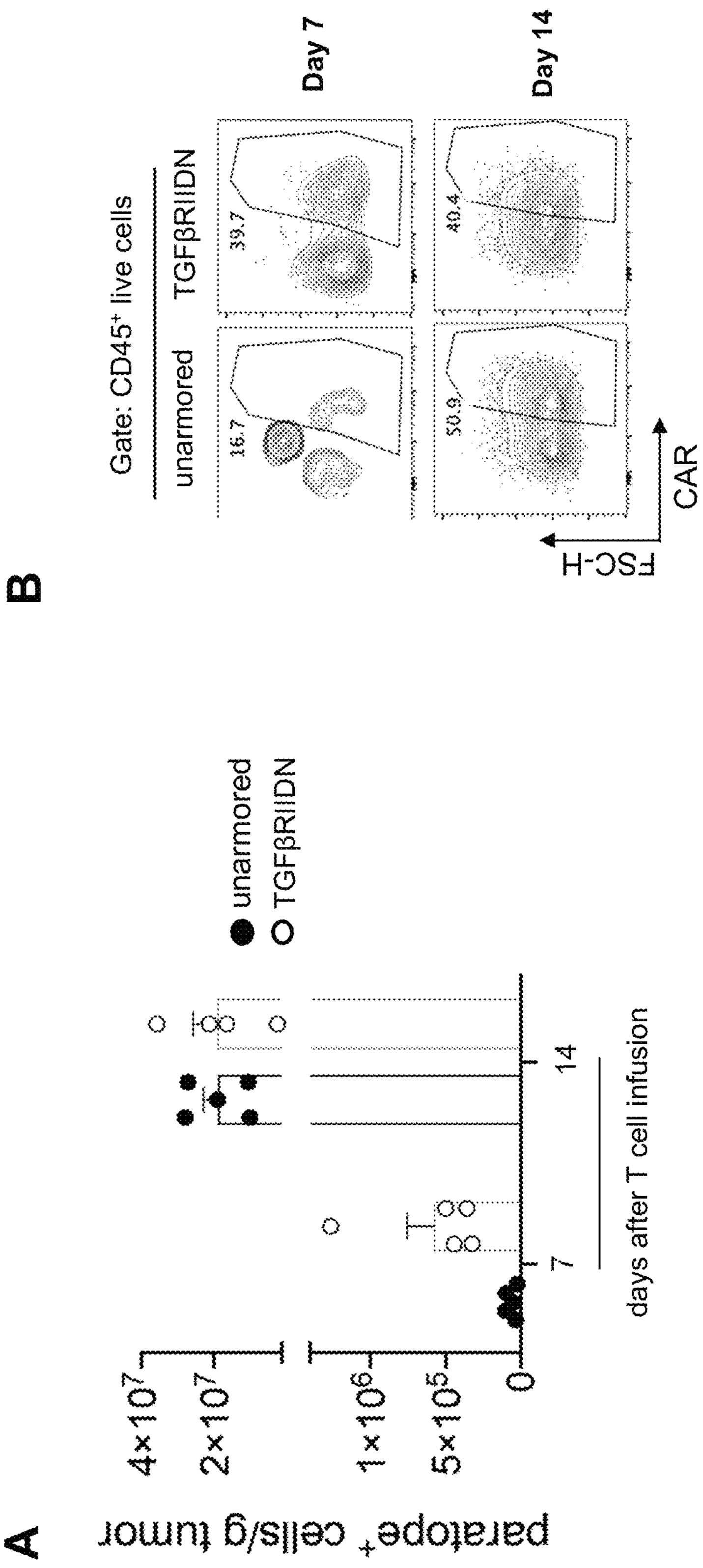
FIG. 10. Increased number of tumor-infiltrating lymphocytes in mice treated with TGFβRIIDN-armored CAR-T cells. Mice bearing Huh7-TGF-β over-expressing tumors were dosed with $7\times10^6$ untransduced T cells, unarmored or TGFβRIIDN-armored GPC3 CAR-T. 10A. Number of $CAR^+$ cells in the tumor of mice harvested at the indicated time points. 10B. Representative example of FACS data summarized in 10A.
Figure 11:
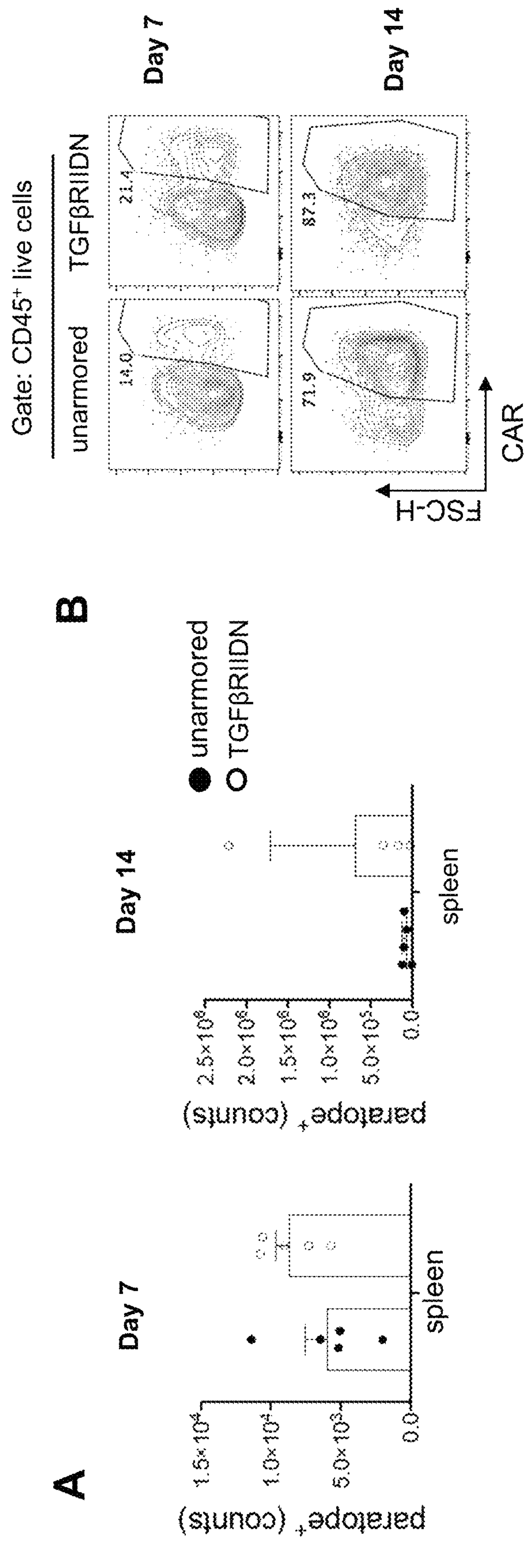
FIG. 11. Increased number of TGFβRIIDN-armored CAR-T cells in the spleen. Mice bearing Huh7-TGF-β over-expressing tumors were dosed with $7\times10^6$ untransduced T cells, unarmored or TGFβRIIDN-armored GPC3 CAR-T cells. 11A. Number of $CAR^+$ cells in the spleen of mice harvested at the indicated time points. 11B. Representative example of FACS data summarized in 11A.

Ex vivo analysis was performed on Huh7-TGFβ tumor bearing mice dosed with $7\times10^6$CAR-T. Seven or fourteen days after infusion, tumors and spleens were collected from 5 mice per group. The number of CAR+ cells was calculated by flow cytometry upon staining with AF647-labeled anti-idiotypic antibody to the GPC3-CAR and using AccuCheck Counting Beads. (See FIGS. 10 and 11).

Figure 12:
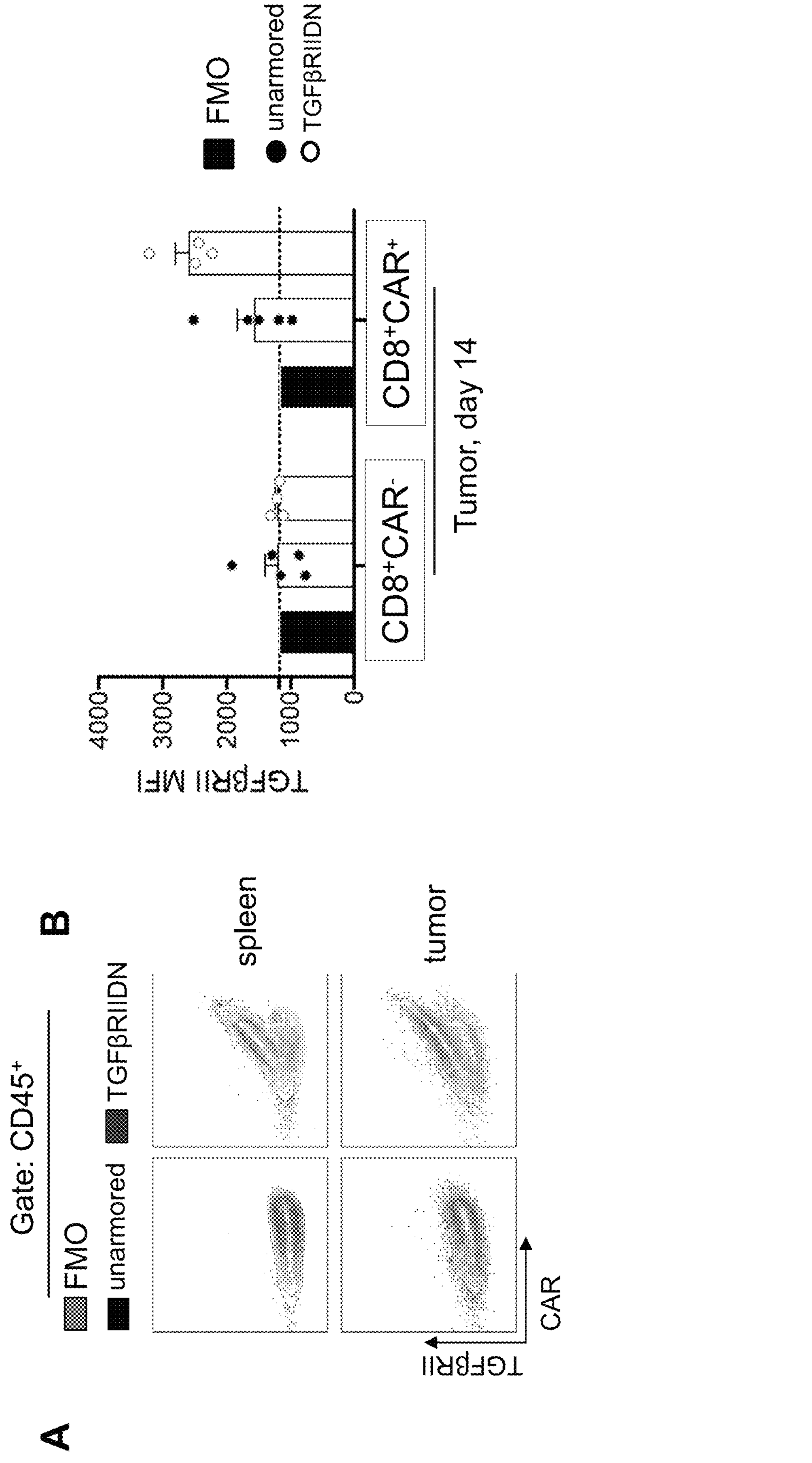
FIG. 12. Expression of TGFβRII on the surface of $CAR^+$ cells ex vivo. 12A. Expression of CAR and TGFβRII on the surface of lymphocytes infiltrating the spleen or the tumor 14 days after the infusion in mice bearing Huh7-TGF-β over-expressing tumors. (FMO: fluorescence minus one) 12B. Mean Fluorescence Intensity (MFI) of TGFβRII on the surface of $CAR^+$ or $CAR^-$ $CD8^+$ T cells in the tumor.

Mice bearing Huh-7-TGFβ tumors were dosed with $7\times10^6$CAR-T cells. Fourteen days after infusion, tumors were collected and the expression of the TGFβRII was evaluated by flow cytomety staining on CAR positive and CAR negative cells. (See FIG. 12).

Figure 13:
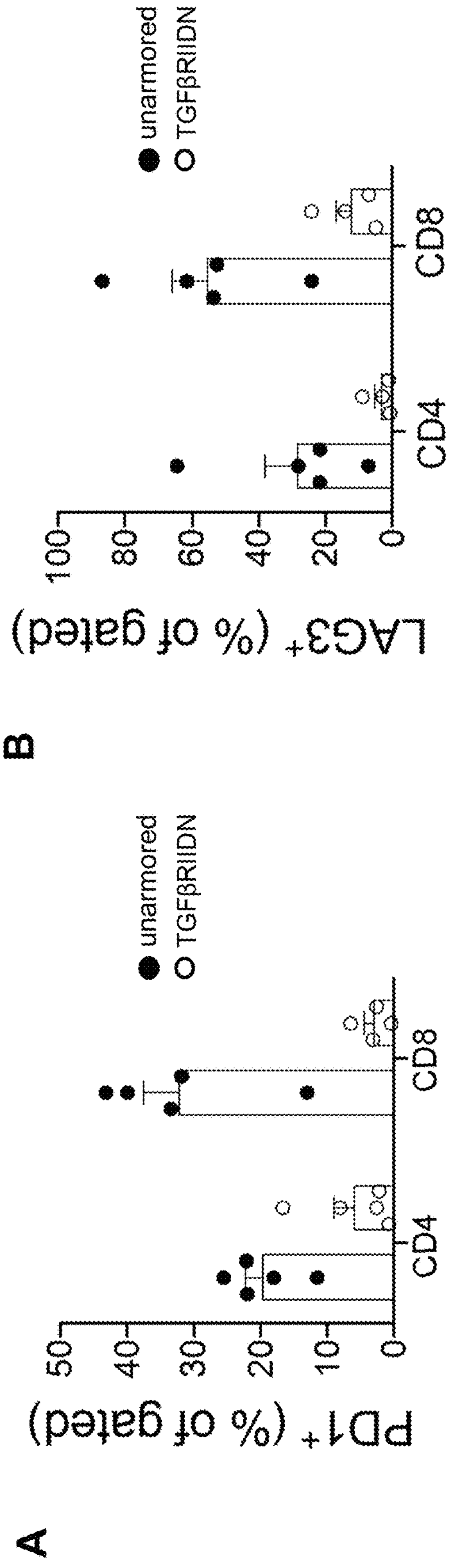
FIG. 13. Decreased PD1 and LAG3 expression on the surface of TGFβRIIDN-armored CAR-T cells in the tumor. Expression of PD1 (A) and LAG3 (B) on the surface of tumor-infiltrating $CD8^+$ and $CD4^+CAR^+$ T cells 14 days after the infusion in mice bearing Huh7-TGF-β over-expressing tumors.
Figure 14:
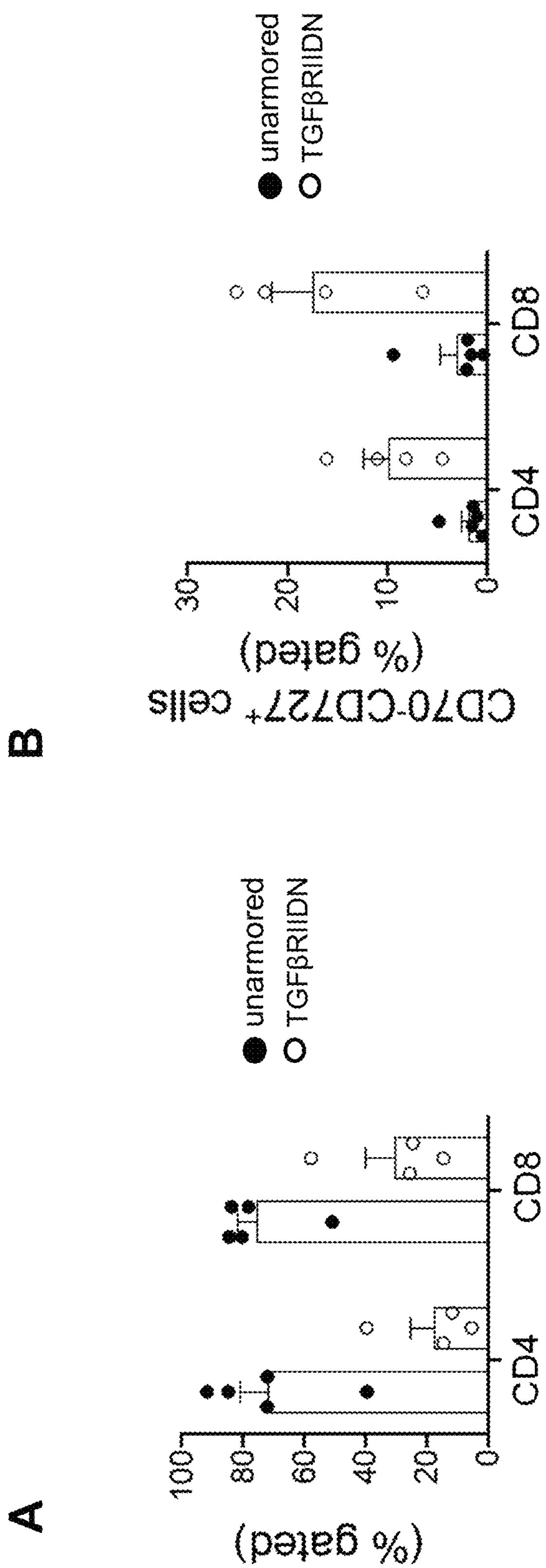
FIG. 14. Decreased expression of CD70 and increased expression of CD27 cells on the surface of TGFβRIIDN-armored CAR-T cells in the tumor. Frequency of $CD70^+$ $CD27^-$ (A) and of $CD70^+CD27^-$ (B) on the surface of tumor-infiltrating $CD8^+$ and $CD4^+CAR^+$ T cells 14 days after the infusion in mice bearing Huh7-TGF-β over-expressing tumors.

Mice bearing Huh-7-TGFβ tumors were dosed with $7\times10^6$CAR-T cells. Fourteen days after infusion, tumors were collected and the expression of PD1, LAG3, CD27 and CD70 was evaluated on the surface of CAR-T. (See FIGS. 13 and 14).

Figure 15:
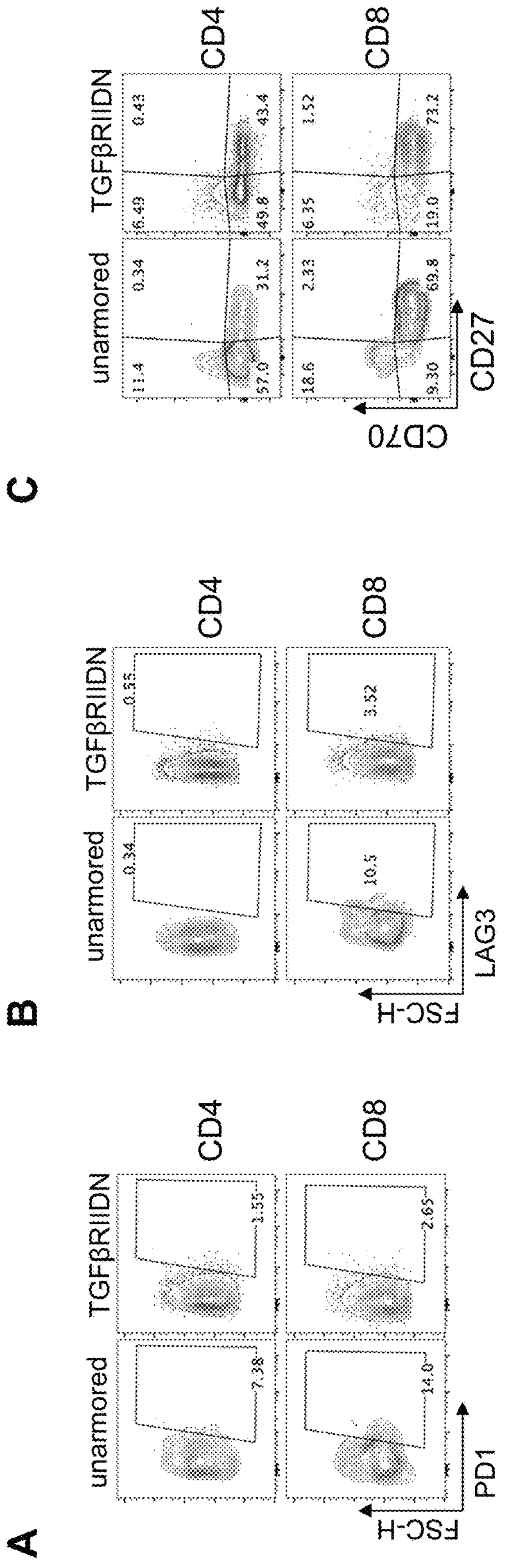
FIG. 15. Immunophenotype of CAR-T cells in the spleen. Expression of PD1 (15A), LAG3 (15B), and CD27/CD70 (15C) on the surface of $CD8^+$ and $CD4^+CAR^+$ T cells in the spleen 14 days after the infusion in mice bearing Huh7-TGF-β over-expressing tumors.

Mice bearing Huh-7-TGFβ tumors were dosed with $7\times10^6$CAR-T cells. Fourteen days after infusion, spleens were collected and the expression of PD1, LAG3, CD27 and CD70 was evaluated by flow cytometry staining. (See FIG. 15).

Figure 16:
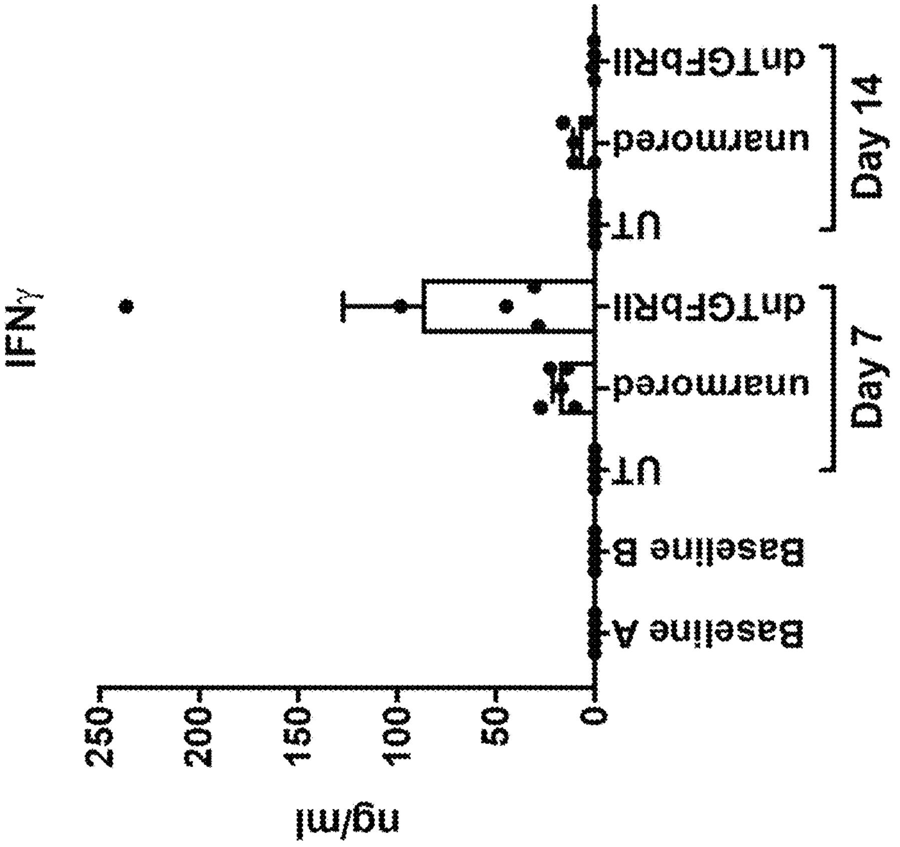
FIG. 16. Analysis of serum IFN-γ. Concentration of IFN-γ detected in the serum of mice bearing Huh7-TGF-β over-expressing tumors. and infused with untransduced T cells, unarmored or armored GPC3 CAR-T cells (Baseline A: before tumor implantantion; Baseline B: before CAR-T infusion).
Figure 17:
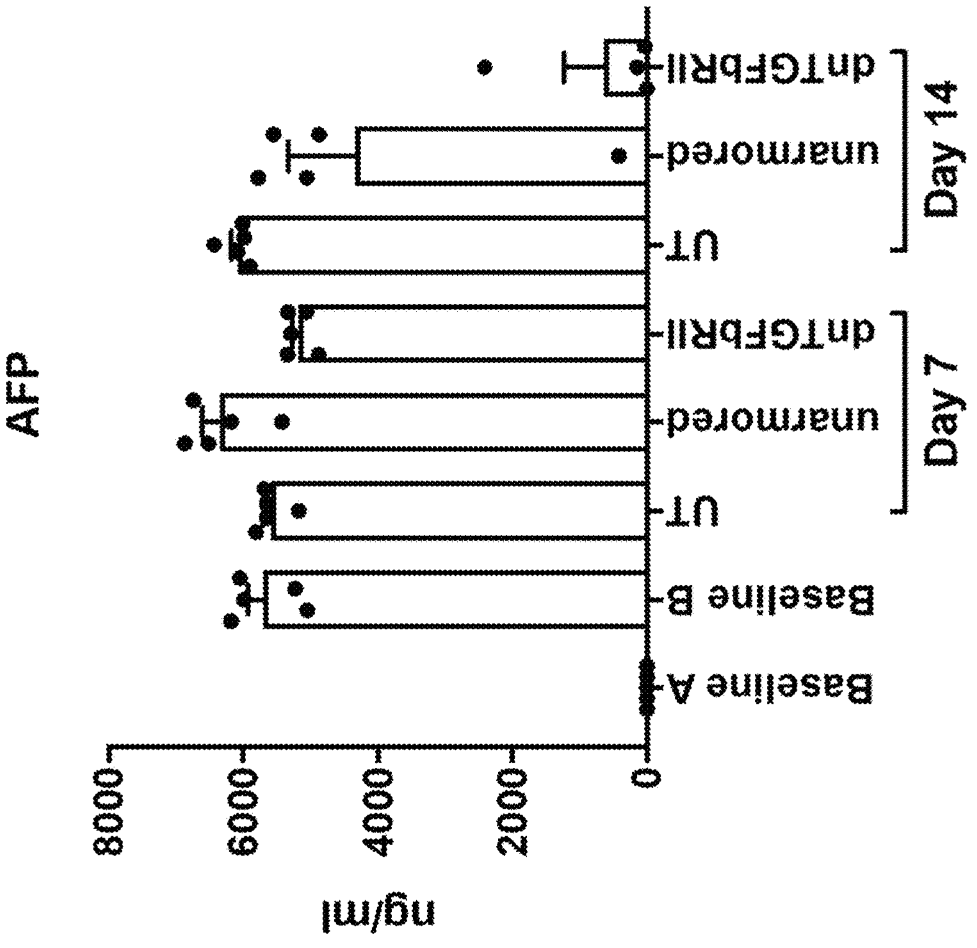
FIG. 17. Analysis of serum AFP. Concentration of AFP detected in the serum of mice bearing Huh7-TGF-β over-expressing tumors and infused with untransduced T cells, unarmored or armored GPC3 CAR-T cells (Baseline A: before tumor implantantion; Baseline B: before CAR-T infusion).

Mice bearing Huh-7-TGFβ tumors were dosed with $7\times10^6$CAR-T cells. For serum cytokine and AFP analysis, blood was harvested in small volumes at the indicated time points and serum separated using BD Microtainer Serum Separator Tubes. Cytokine levels were determined using MSD assays, while AFP was assessed by sandwich ELISA. Five mice per group were bled before tumor implantation (Baseline A), before CAR-T infusion (Baseline B), 7- and 14-days post infusion. (See FIGS. 16 and 17).

Results

Untransduced T cells had no discernable effect on tumor growth. Treatment with unarmored CAR-T cells resulted in minor reduction in tumor volume at the lowest dose (3 million cells/mouse) while a more profound effect was evident at higher doses, resulting in complete tumor regression. In contrast, administration of TGFβRIIDN armored CAR-T cells induced a profound reduction of tumor volume and complete regression even at the lowest dose. Moreover, progression-free survival was significantly extended at all treatment doses of TGFβRIIDN armored CAR-T cell compared to unarmored CAR-T (See FIG. 9). Ex vivo analysis of CAR-T cells was performed on mice infused with $7\times10^6$ cells. In line with the enhanced efficacy, an increased number of tumor-infiltrating lymphocytes (TILs) was detected in the TGFβRIIDN treated mice 7 days after infusion, indicating an ongoing active immune response and associated proliferation that plateaued at day 14 post-treatment (See FIG. 10). Conversely, increased number of CAR-T cells was observed 14 days after infusion in the spleen of TGFβRIIDN armored CAR-T-treated mice, suggesting enhanced proliferation by the CAR-T cells and more $CAR^{+}$ cells were therefore detectable in the circulation (See FIG. 11). To investigate if the TGFβRIIDN was detectable on CAR-T cells upon in vivo expansion, we analyzed the expression of TGFβRII on TILs and lymphocytes in the spleen 14 days after infusion. While TGFβRII was barely detectable on unarmored cells, lymphocytes of mice treated with the armored CAR-T cells co-expressed CAR and TGFβRII. Therefore, it is reasonable to assume that the TGFβRII expressed on the TGFβRIIDN TILs is the dominant negative receptor, detectable ex vivo after an active immune response and associated antigen-dependent proliferation (See FIG. 12). Notably, TGFβRIIDN TILs expressed low level of the exhaustion markers LAG3 and PD1 (See FIG. 13), the latter being directly regulated by TGF-β in a SMAD3-dependent fashion (Park, B. V., Freeman, Z. T., Ghasemzadeh, A., Chattergoon, M. A., Rutebemberwa, A., Steigner, J. et al. (2016). TGFβ1-Mediated SMAD3 Enhances PD-1 Expression on Antigen-Specific T Cells in Cancer. *Cancer Discov,* 6(12), 1366-1381). Moreover, TGFβRIIDN TILs expressed less CD70 and conversely more CD27 compared to unarmored TILs (See FIG. 14). This result agrees with previous evidence showing that TGF-β upregulates CD70 expression and induces exhaustion of effector memory T cells, and reinforce the concept that expression of the dominant negative receptor protects CAR-T cells from TGF-β mediated immunosuppression (Yang, Z Z., Grote, D., Xiu, B. et al. TGF-β upregulates CD70 expression and induces exhaustion of effector memory T cells in B-cell non-Hodgkin's lymphoma. Leukemia 28, 1872-1884 (2014). https://doi.org/10.1038/leu.2014.84). In contrast to TILs, CAR-T cells in the periphery did not express co-inhibitory markers or CD70 and were mostly CD27 positive consistently with a non-activated status (See FIG. 15). In line with enhanced efficacy and higher number of TILs, more IFN-γ was detected in the serum of mice infused with TGFβRIIDN CAR-T 7 days after infusion, and a dramatic decrease in the serum concentration of the tumor marker AFP 14 days after infusion (See FIGS. 16 and 17). This result demonstrates that expression of TGFβRIIDN increases the efficacy of CAR-T therapy by counteracting the immunosuppressive action of TGF-β in vivo.

Conclusion

TGFβRIIDN armored CAR-T cells exhibit considerable promise for being an effective treatment for GPC3+ tumors in vivo.

Example 5: TGFβRIIDN Armored CAR-T-Cells In Vivo—Hepatocellular Carcinoma Patient-Derived Xenograft Models Summary In the present example, the effectiveness of TGFβRIIDN armored CAR-T cells in a number of $GPC3^{+}$ hepatocellular carcinoma patient derived xenograft cells was determined in vivo.

Methods

Figure 18:
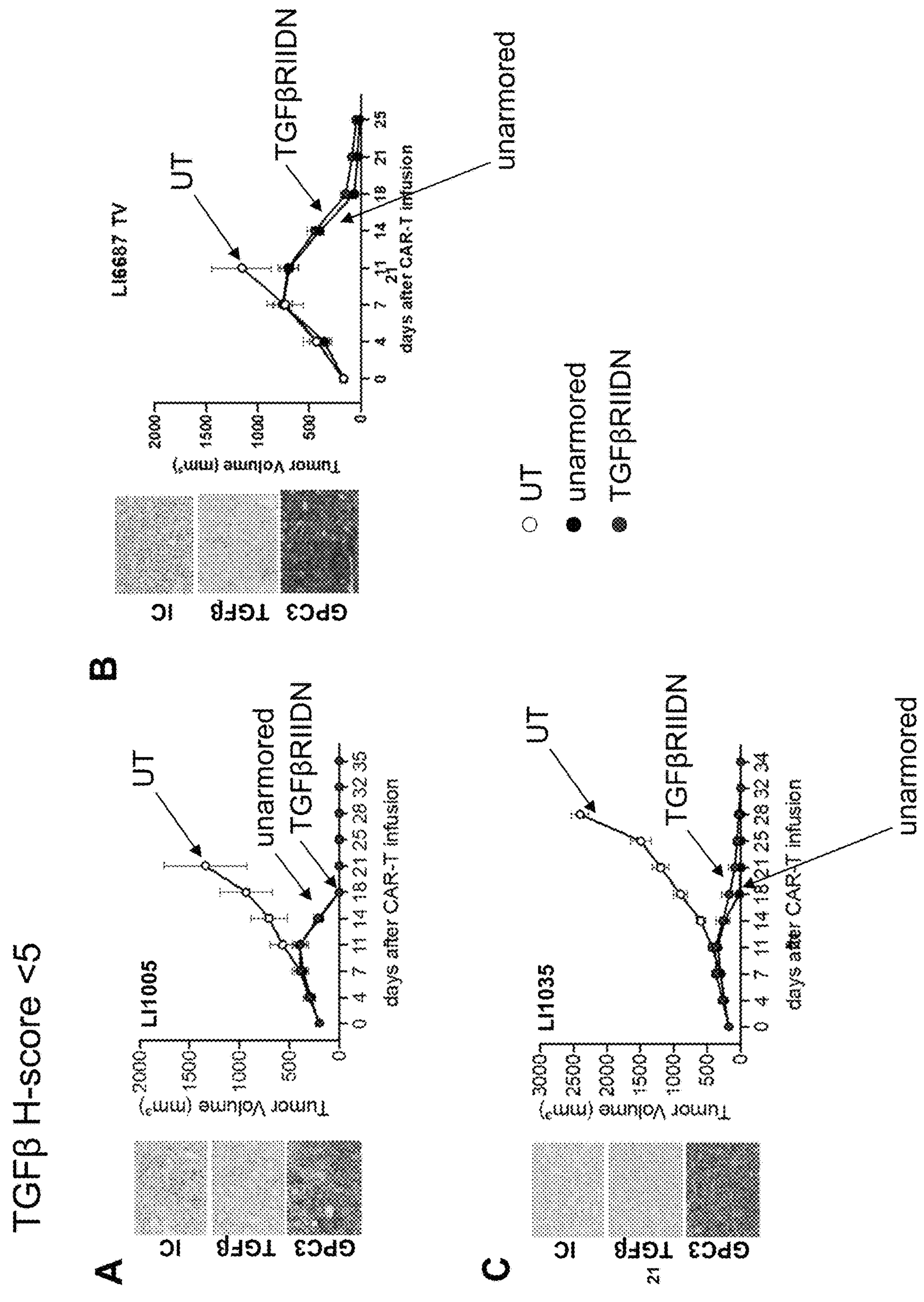
FIG. 18. TGFβRIIDN-armored CAR-T cells and in vivo reduction of tumor volume in TGFβ(−) PDX models. A-C represent the tumor volume of three different $GPC3^+$ TGF-β-Hepatocellular Carcinoma (HCC) patient derived xenograft (PDX) models. For each model, $5\times10^6$ untransduced T cells, unarmored or armored GPC3 CAR-T cells were infused in tumor-bearing mice, and tumor volume was measured bi-weekly (5 mice/group).
Figure 19:
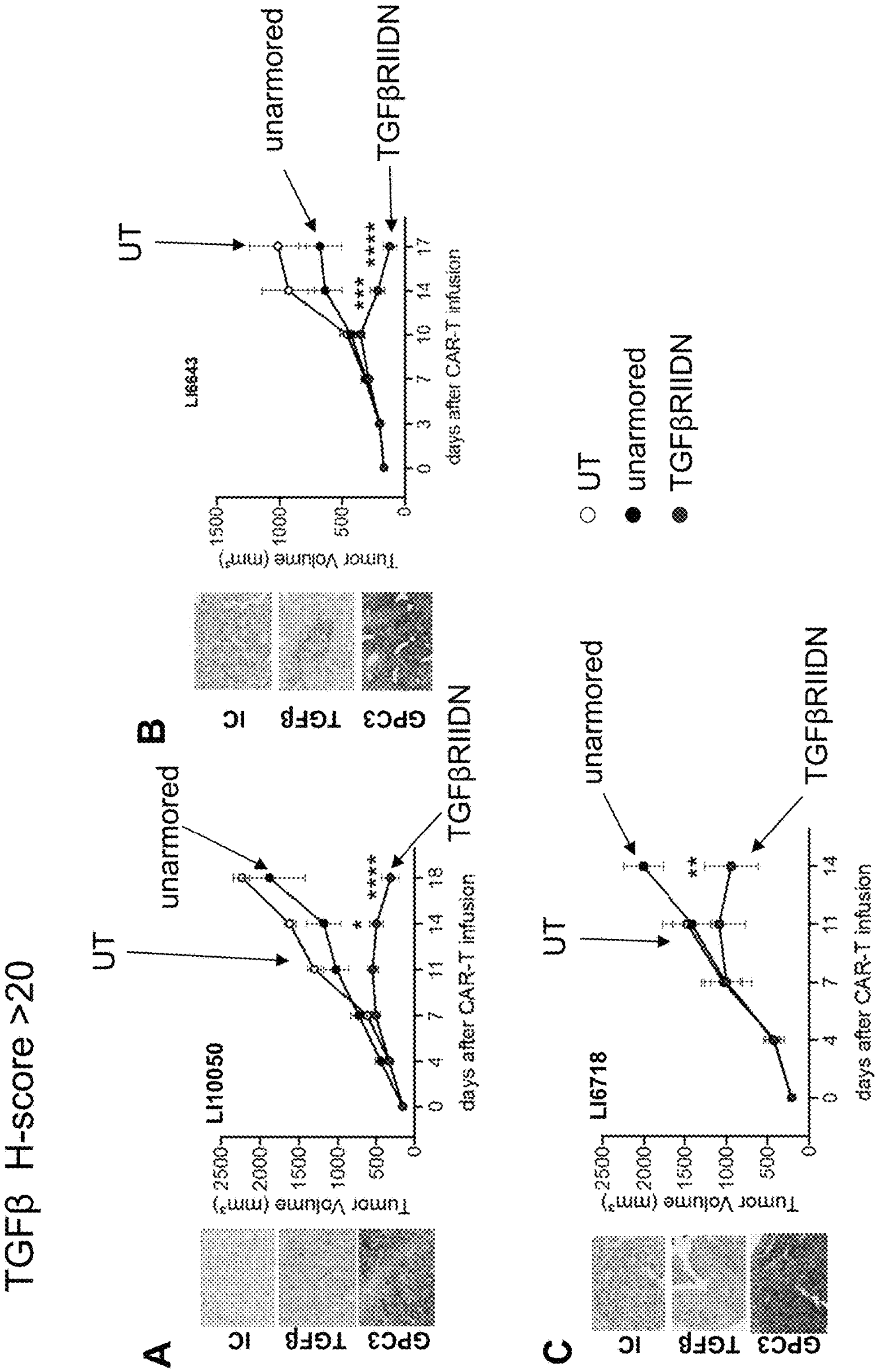
FIG. 19. TGFβRIIDN-armored CAR-T cells and in vivo reduction of tumor volume in TGFβ(+) PDX models. A-E represent the tumor volume of five different $GPC3^+$ $TGF\text{-}\beta^+$ Hepatocellular Carcinoma (HCC) patient derived xenograft (PDX) models. For each model $5\times10^6$ untransduced T cells, unarmored or armored GPC3 CAR-T cells were infused in tumor bearing mice, and tumor volume was measured bi-weekly (5 mice/group).
Figure 19:
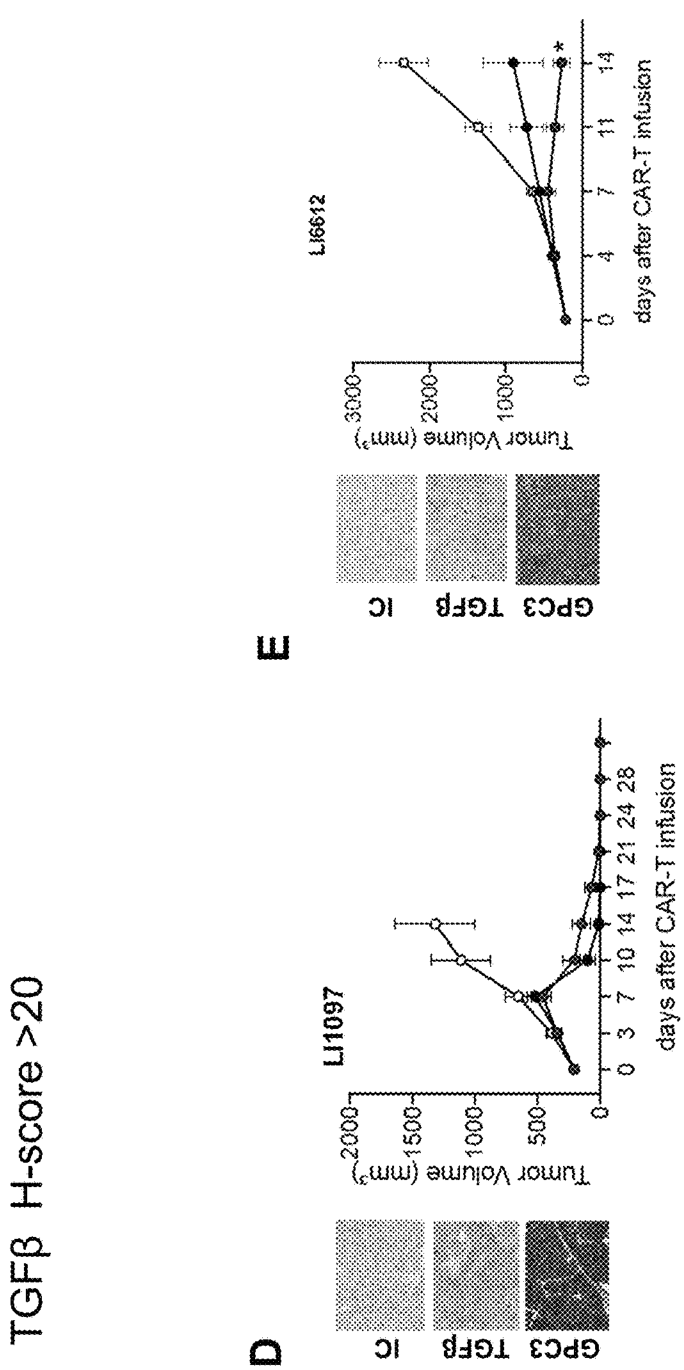

This study was conducted by Crown Bioscience Inc. Eight PDX models were selected based on expression of GPC3 and TGF-β evaluated by IHC and RNA-sequencing, performed by Crown Bioscience. All the models selected were GPC3 high (IHC score >100), but three of them expressed no TGF-β (IHC score <5) while the other 5 models were TGF-β positive (IHC score >20). According to Crown Bioscience study protocol, tumor fragments from stock mice were harvested and used for inoculation into NCG mice. Each mouse was inoculated subcutaneously in the right front flank with a specific PDX tumor fragment (3×3×3 mm) for tumor development. Mice were randomized when the mean tumor size reached approximately 150-250 $mm^3$. Tumor bearing mice were dosed with 5 million of unarmored or armored CAR-T cells, and untransduced T cells provided by AstraZeneca (5 mice/group), and tumor volume was measured bi-weekly. (See FIGS. 18 and 19).

Results

Tumors grew in the mice that received untransduced T cells. However, in the absence of TGF-β, unarmored and armored cells were equally effective and induced fast and complete regression of all the mice included in the study (See FIG. 18). When infused in TGF-β expressing models, unarmored CAR-T cells had a much less pronounced effect, in contrast TGFβRIIDN armored CAR-T cells were consistently more potent and induced significant tumor regression.

Conclusion

PDX models simulate human tumor biology allowing for natural cancer progression. Therefore, these observations confirm and reinforce the evidence obtained with the Huh7-TGF-β xenograft model. Overall, these data demonstrate that TGFβRIIDN armored GPC3 CAR-T cells might be an effective treatment for $GPC3^+$ tumors in vivo and can maintain their efficacy even in the presence of the immune suppressive factor TGF-β.

The embodiments described herein can be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the embodiments claimed. Thus, it should be understood that although the present description has been specifically disclosed by embodiments, optional features, modification and variation of the concepts herein disclosed may be resorted to by those skilled in the art, and that such modifications and variations are considered to be within the scope of these embodiments as defined by the description and the appended claims. Although some aspects of the present disclosure can be identified herein as particularly advantageous, it is contemplated that the present disclosure is not limited to these particular aspects of the disclosure.

Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group.

It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein.

All patents and publications mentioned in this specification are herein incorporated by reference to the same extent as if each independent patent and publication was specifically and individually indicated to be incorporated by reference. Citation or identification of any reference in any section of this application shall not be construed as an admission that such reference is available as prior art to the present invention.

TABLE 5

Sequences used in the Examples.

| | |
|---|---|
| SEQ ID NO: 1 | GPC3 scFv amino acid sequence |
| SEQ ID NO: 2 | GPC3-2 scFv amino acid sequence |
| SEQ ID NO: 3 | GPC3 BZ CAR amino acid sequence |
| SEQ ID NO: 4 | GPC3 TZ CAR amino acid sequence |
| SEQ ID NO: 5 | GPC3 28Z CAR amino acid sequence |
| SEQ ID NO: 6 | GPC3 28 BZ CAR amino acid sequence |
| SEQ ID NO: 7 | GPC3-2 BZ CAR amino acid sequence |
| SEQ ID NO: 8 | GPC3-2 TZ CAR amino acid sequence |
| SEQ ID NO: 9 | GPC3-2 28Z CAR amino acid sequence |
| SEQ ID NO: 10 | GPC3-2 28BZ CAR amino acid sequence |
| SEQ ID NO: 11 | GPC3 BZ CAR nucleic acid sequence |
| SEQ ID NO: 12 | GPC3 TZ CAR nucleic acid sequence |
| SEQ ID NO: 13 | GPC3 28Z CAR nucleic acid sequence |
| SEQ ID NO: 14 | GPC3 28BZ CAR nucleic acid sequence |
| SEQ ID NO: 15 | GPC3-2 BZ CAR nucleic acid sequence |
| SEQ ID NO: 16 | GPC3-2 TZ CAR nucleic acid sequence |
| SEQ ID NO: 17 | GPC3-2 28Z CAR nucleic acid sequence |
| SEQ ID NO: 18 | GPC3-2 28BZ CAR nucleic acid sequence |
| SEQ ID NO: 19 | GPC3-3 BZ CAR amino acid sequence |
| SEQ ID NO: 20 | GPC3-3 28BZ CAR amino acid sequence |
| SEQ ID NO: 21 | GPC3-4 BZ CAR amino acid sequence |
| SEQ ID NO: 22 | GPC3-3 BZ CAR nucleic acid sequence |
| SEQ ID NO: 23 | GPC3-3 28BZ CAR nucleic acid sequence |
| SEQ ID NO: 24 | GPC3-4 CAR nucleic acid sequence |
| SEQ ID NO: 25 | GPC3 BZ CAR amino acid sequence (WPRE-deleted) |
| SEQ ID NO: 26 | GPC3 BZ CAR nucleic acid sequence (WPRE-deleted) |
| SEQ ID NO: 27 | GPC3 VH |
| SEQ ID NO: 28 | GPC3 VL |
| SEQ ID NO: 29 | GPC3-2 VH |
| SEQ ID NO: 30 | GPC3-2 VL |
| SEQ ID NO: 31 | GPC3-3 scFv amino acid sequence |
| SEQ ID NO: 32 | GPC3-4 scFv amino acid sequence |
| SEQ ID NO: 33 | GPC3 scFv nucleic acid sequence |
| SEQ ID NO: 34 | GPC3-2 scFv nucleic acid sequence |
| SEQ ID NO: 35 | GPC3-3 scFv nucleic acid sequence |
| SEQ ID NO: 36 | GPC3-4 scFv nucleic acid sequence |
| SEQ ID NO: 37 | GPC3 and GPC3-2 VH CDR1 |
| SEQ ID NO: 38 | GPC3 and GPC3-2 VH CDR2 |
| SEQ ID NO: 39 | GPC3 and GPC3-2 VH CDR3 |
| SEQ ID NO: 40 | GPC3 VL CDR1 |
| SEQ ID NO: 41 | GPC3 VL CDR2 |
| SEQ ID NO: 42 | GPC3 VL CDR3 |
| SEQ ID NO: 43 | GPC3-2 VL CDR1 |
| SEQ ID NO: 44 | GPC3-2 VL CDR2 |
| SEQ ID NO: 45 | GPC3-2 VL CDR3 |
| SEQ ID NO: 46 | GPC3 BZ CAR and Dominant-negative TGF-β receptor type 2 nucleic acid sequence |
| SEQ ID NO: 47 | GPC3 BZ CAR and Dominant-negative TGF-β receptor type 2 amino acid sequence |

TABLE 6

| Sequences | |
|---|---|
| SEQ ID NO: 1 | EVQLLESGGGLVQPGGSLRLSCAASGFTFSSYAMSWVRQAPG<br>KGLEWVSAISGSGGSTYYADSVKGRFTISRDNSKNTLYLQMN<br>SLRAEDTAVYYCARGKRYFDYWGQGTMVTVSSGGGGSGGG<br>GSGGGGSSYELTQPPSASGTPGQRVTISCSGGSSNIGSNTVNW<br>FRQLPGTAPKLLVYFNNQRPSGVPDRFSGSKSGTSASLAIGGL<br>QSDDEADYYCVAWDDSLNAPVFGGGTKVTVL |
| SEQ ID NO: 2 | EVQLLESGGGLVQPGGSLRLSCAASGFTFSSYAMSWVRQAPG<br>KGLEWVSAISGSGGSTYYADSVKGRFTISRDNSKNTLYLQMN<br>SLRAEDTAVYYCAKGKRYFDYWGQGTMVTVSSGGGGSGGG<br>GSGGGGSQSVLTQPPSASGTPGQRVTISCSGGSSDIGSNTVNW<br>YQQLPGTAPKLLIYYNNQRPSGVPDRFSGSKSGTSASLAISGL<br>QSEDEADYYCATWDDRMYSPVFGGGTKLTVL |
| SEQ ID NO: 3 | MLLLVTSLLLCELPHPAFLLIPGVHSEVQLLESGGGLVQPGGS<br>LRLSCAASGFTFSSYAMSWVRQAPGKGLEWVSAISGSGGSTY<br>YADSVKGRFTISRDNSKNTLYLQMNSLRAEDTAVYYCARGK<br>RYFDYWGQGTMVTVSSGGGGSGGGGSGGGGSSYELTQPPSA<br>SGTPGQRVTISCSGGSSNIGSNTVNWFRQLPGTAPKLLVYFNN<br>QRPSGVPDRFSGSKSGTSASLAIGGLQSDDEADYYCVAWDDS<br>LNAPVFGGGTKVTVLESKYGPPCPPCPFWVLVVVGGVLACYS<br>LLVTVAFIIFWVKRGRKKLLYIFKQPFMRPVQTTQEEDGCSCR<br>FPEEEEGGCELRVKFSRSADAPAYQQGQNQLYNELNLGRREE<br>YDVLDKRRGRDPEMGGKPRRKNPQEGLYNELQKDKMAEAY<br>SEIGMKGERRRGKGHDGLYQGLSTATKDTYDALHMQALPPR<br>* |
| SEQ ID NO: 4 | MLLLVTSLLLCELPHPAFLLIPGVHSEVQLLESGGGLVQPGGS<br>LRLSCAASGFTFSSYAMSWVRQAPGKGLEWVSAISGSGGSTY<br>YADSVKGRFTISRDNSKNTLYLQMNSLRAEDTAVYYCARGK<br>RYFDYWGQGTMVTVSSGGGGSGGGGSGGGGSSYELTQPPSA<br>SGTPGQRVTISCSGGSSNIGSNTVNWFRQLPGTAPKLLVYFNN<br>QRPSGVPDRFSGSKSGTSASLAIGGLQSDDEADYYCVAWDDS<br>LNAPVFGGGTKVTVLESKYGPPCPPCPFWVLVVVGGVLACYS<br>LLVTVAFIIFWVRVKFSRSADAPA* |
| SEQ ID NO: 5 | MLLLVTSLLLCELPHPAFLLIPGVHSEVQLLESGGGLVQPGGS<br>LRLSCAASGFTFSSYAMSWVRQAPGKGLEWVSAISGSGGSTY<br>YADSVKGRFTISRDNSKNTLYLQMNSLRAEDTAVYYCARGK<br>RYFDYWGQGTMVTVSSGGGGSGGGGSGGGGSSYELTQPPSA<br>SGTPGQRVTISCSGGSSNIGSNTVNWFRQLPGTAPKLLVYFNN<br>QRPSGVPDRFSGSKSGTSASLAIGGLQSDDEADYYCVAWDDS<br>LNAPVFGGGTKVTVLESKYGPPCPPCPFWVLVVVGGVLACYS<br>LLVTVAFIIFWVRSKRSRLLHSDYMNMTPRRPGPTRKHYQPY<br>APPRDFAAYRSRVKFSRSADAPAYQQGQNQLYNELNLGRRE<br>EYDVLDKRRGRDPEMGGKPRRKNPQEGLYNELQKDKMAEA<br>YSEIGMKGERRRGKGHDGLYQGLSTATKDTYDALHMQALPP<br>R* |
| SEQ ID NO: 6 | MLLLVTSLLLCELPHPAFLLIPGVHSEVQLLESGGGLVQPGGS<br>LRLSCAASGFTFSSYAMSWVRQAPGKGLEWVSAISGSGGSTY<br>YADSVKGRFTISRDNSKNTLYLQMNSLRAEDTAVYYCARGK<br>RYFDYWGQGTMVTVSSGGGGSGGGGSGGGGSSYELTQPPSA<br>SGTPGQRVTISCSGGSSNIGSNTVNWFRQLPGTAPKLLVYFNN<br>QRPSGVPDRFSGSKSGTSASLAIGGLQSDDEADYYCVAWDDS<br>LNAPVFGGGTKVTVLESKYGPPCPPCPFWVLVVVGGVLACYS<br>LLVTVAFIIFWVRSKRSRLLHSDYMNMTPRRPGPTRKHYQPY<br>APPRDFAAYRSKRGRKKLLYIFKQPFMRPVQTTQEEDGCSCR<br>FPEEEEGGCELRVKFSRSADAPAYQQGQNQLYNELNLGRREE<br>YDVLDKRRGRDPEMGGKPRRKNPQEGLYNELQKDKMAEAY<br>SEIGMKGERRRGKGHDGLYQGLSTATKDTYDALHMQALPPR<br>* |
| SEQ ID NO: 7 | MLLLVTSLLLCELPHPAFLLIPEVQLLESGGGLVQPGGSLRLSC<br>AASGFTFSSYAMSWVRQAPGKGLEWVSAISGSGGSTYYADS<br>VKGRFTISRDNSKNTLYLQMNSLRAEDTAVYYCAKGKRYFD<br>YWGQGTMVTVSSGGGGSGGGGSGGGGSQSVLTQPPSASGTP<br>GQRVTISCSGGSSDIGSNTVNWYQQLPGTAPKLLIYYNNQRPS<br>GVPDRFSGSKSGTSASLAISGLQSEDEADYYCATWDDRMYSP<br>VFGGGTKLTVLESKYGPPCPPCPFWVLVVVGGVLACYSLLVT<br>VAFIIFWVKRGRKKLLYIFKQPFMRPVQTTQEEDGCSCRFPEE<br>EEGGCELRVKFSRSADAPAYQQGQNQLYNELNLGRREEYDV<br>LDKRRGRDPEMGGKPRRKNPQEGLYNELQKDKMAEAYSEIG<br>MKGERRRGKGHDGLYQGLSTATKDTYDALHMQALPPR* |
| SEQ ID NO: 8 | MLLLVTSLLLCELPHPAFLLIPEVQLLESGGGLVQPGGSLRLSC<br>AASGFTFSSYAMSWVRQAPGKGLEWVSAISGSGGSTYYADS<br>VKGRFTISRDNSKNTLYLQMNSLRAEDTAVYYCAKGKRYFD |

TABLE 6-continued

| | Sequences |
|---|---|
| | YWGQGTMVTVSSGGGGSGGGGSGGGGSQSVLTQPPSASGTP<br>GQRVTISCSGGSSDIGSNTVNWYQQLPGTAPKLLIYYNNQRPS<br>GVPDRFSGSKSGTSASLAISGLQSEDEADYYCATWDDRMYSP<br>VFGGGTKLTVLESKYGPPCPPCPFWVLVVVGGVLACYSLLVT<br>VAFIIFWVRVKFSRSADAPA* |
| SEQ ID NO: 9 | MLLLVTSLLLCELPHPAFLLIPEVQLLESGGGLVQPGGSLRLSC<br>AASGFTFSSYAMSWVRQAPGKGLEWVSAISGSGGSTYYADS<br>VKGRFTISRDNSKNTLYLQMNSLRAEDTAVYYCAKGKRYFD<br>YWGQGTMVTVSSGGGGSGGGGSGGGGSQSVLTQPPSASGTP<br>GQRVTISCSGGSSDIGSNTVNWYQQLPGTAPKLLIYYNNQRPS<br>GVPDRFSGSKSGTSASLAISGLQSEDEADYYCATWDDRMYSP<br>VFGGGTKLTVLESKYGPPCPPCPFWVLVVVGGVLACYSLLVT<br>VAFIIFWVRSKRSRLLHSDYMNMTPRRPGPTRKHYQPYAPPR<br>DFAAYRSRVKFSRSADAPAYQQGQNQLYNELNLGRREEYDV<br>LDKRRGRDPEMGGKPRRKNPQEGLYNELQKDKMAEAYSEIG<br>MKGERRRGKGHDGLYQGLSTATKDTYDALHMQALPPR* |
| SEQ ID NO: 10 | MLLLVTSLLLCELPHPAFLLIPEVQLLESGGGLVQPGGSLRLSC<br>AASGFTFSSYAMSWVRQAPGKGLEWVSAISGSGGSTYYADS<br>VKGRFTISRDNSKNTLYLQMNSLRAEDTAVYYCAKGKRYFD<br>YWGQGTMVTVSSGGGGSGGGGSGGGGSQSVLTQPPSASGTP<br>GQRVTISCSGGSSDIGSNTVNWYQQLPGTAPKLLIYYNNQRPS<br>GVPDRFSGSKSGTSASLAISGLQSEDEADYYCATWDDRMYSP<br>VFGGGTKLTVLESKYGPPCPPCPFWVLVVVGGVLACYSLLVT<br>VAFIIFWVRSKRSRLLHSDYMNMTPRRPGPTRKHYQPYAPPR<br>DFAAYRSKRGRKKLLYIFKQPFMRPVQTTQEEDGCSCRFPEEE<br>EGGCELRVKFSRSADAPAYQQGQNQLYNELNLGRREEYDVL<br>DKRRGRDPEMGGKPRRKNPQEGLYNELQKDKMAEAYSEIG<br>MKGERRRGKGHDGLYQGLSTATKDTYDALHMQALPPR* |
| SEQ ID NO: 11 | atgctgctgctggtgacaagcctgctgctgtgcgaactgccccatcccgccttcctgctgattcctg<br>gtgtacactccgaggtgcagctgttggagtctgggggaggcttggtacagcctggggggtccctg<br>agactctcctgtgcagcctctggattcacctttagcagctatgccatgagctgggtccgccaggctc<br>cagggaaggggctggagtgggtctcagctattagtggtagtggtggtagcacatactacgcagac<br>tccgtgaagggccggttcaccatctccagagacaattccaagaacacgctgtatctgcaaatgaac<br>agcctgagagccgaggacacggccgtgtattactgtgcgagaggaaagcgatactttgactactg<br>gggccaggggacaatggtcaccgtctcgagtggtggggggggcagcggtggtggaggctctg<br>gtggaggagggagctcctatgagctgactcagccaccctcagcgtctgggacccccgggcaga<br>gggtcaccatctcttgttctggaggcagctccaacatcggaagtaatactgtaaactggttccggca<br>gctcccaggaacggcccccaaactcctcgtttattttaataatcagcgaccctcaggggtccctga<br>ccgattctctggctccaagtctggcacctcggcctccctggccatcggtgggctccagtctgacga<br>tgaggctgactattactgtgtagcatgggatgactctctgaatgctccggtgttcggcggagggac<br>caaggtcaccgtcctagagagcaaatatggaccaccatgccctccatgtccttttttgggtcctggtg<br>gtcgtgggaggcgtgctggcatgttattctctgctggtcacagtggctttcatcatcttctgggtcaa<br>gcgaggccggaagaaactgctgtacatcttcaaacagccttttatgcgcccagtgcagacaactc<br>aggaggaagacggctgctcttgtcggttccccgaggaagaggaagggggatgtgagctgcgcg<br>tgaagttttctcgaagtgccgatgctcctgcatatcagcagggacagaaccagctgtacaacgagc<br>tgaatctgggccggagagagaggaatacgacgtgctggataagaggcgcggcagagacccagaa<br>atgggcgggaagccacgacggaaaaaccccccaggaggggctgtataatgaactgcagaagga<br>caaaatggccgaggcttacagcgaaatcgggatgaagggagagagaaggcgcggaaaaggc<br>cacgatggactgtatcagggcctgagcactgccaccaaggacacctacgatgctctgcacatgca<br>ggcactgccacccaggtga |
| SEQ ID NO: 12 | atgctgctgctggtgacaagcctgctgctgtgcgaactgccccatcccgccttcctgctgattcctg<br>gtgtacactccgaggtgcagctgttggagtctgggggaggcttggtacagcctggggggtccctg<br>agactctcctgtgcagcctctggattcacctttagcagctatgccatgagctgggtccgccaggctc<br>cagggaaggggctggagtgggtctcagctattagtggtagtggtggtagcacatactacgcagac<br>tccgtgaagggccggttcaccatctccagagacaattccaagaacacgctgtatctgcaaatgaac<br>agcctgagagccgaggacacggccgtgtattactgtgcgagaggaaagcgatactttgactactg<br>gggccaggggacaatggtcaccgtctcgagtggtggggggggcagcggtggtggaggctctg<br>gtggaggagggagctcctatgagctgactcagccaccctcagcgtctgggacccccgggcaga<br>gggtcaccatctcttgttctggaggcagctccaacatcggaagtaatactgtaaactggttccggca<br>gctcccaggaacggcccccaaactcctcgtttattttaataatcagcgaccctcaggggtccctga<br>ccgattctctggctccaagtctggcacctcggcctccctggccatcggtgggctccagtctgacga<br>tgaggctgactattactgtgtagcatgggatgactctctgaatgctccggtgttcggcggagggac<br>caaggtcaccgtcctagagagcaaatatggaccaccatgccctccatgtccttttttgggtcctggtg<br>gtcgtgggaggcgtgctggcatgttattctctgctggtcacagtggctttcatcatcttctgggtccg<br>cgtgaagttttctcgaagtgccgatgctcctgcatga |
| SEQ ID NO: 13 | atgctgctgctggtgacaagcctgctgctgtgcgaactgccccatcccgccttcctgctgattcctg<br>gtgtacactccgaggtgcagctgttggagtctgggggaggcttggtacagcctggggggtccctg<br>agactctcctgtgcagcctctggattcacctttagcagctatgccatgagctgggtccgccaggctc<br>cagggaaggggctggagtgggtctcagctattagtggtagtggtggtagcacatactacgcagac<br>tccgtgaagggccggttcaccatctccagagacaattccaagaacacgctgtatctgcaaatgaac<br>agcctgagagccgaggacacggccgtgtattactgtgcgagaggaaagcgatactttgactactg<br>gggccaggggacaatggtcaccgtctcgagtggtggggggggcagcggtggtggaggctctg<br>gtggaggagggagctcctatgagctgactcagccaccctcagcgtctgggacccccgggcaga |

TABLE 6-continued

| | Sequences |
|---|---|
| | gggtcaccatctcttgttctggaggcagctccaacatcggaagtaatactgtaaactggttccggca<br>gctcccaggaacggcccccaaactcctcgtttattttaataatcagcgaccctcaggggtccctga<br>ccgattctctggctccaagtctggcacctcggcctccctggccatcggtgggctccagtctgacga<br>tgaggctgactattactgtgtagcatgggatgactctctgaatgctccggtgttcggcggagggac<br>caaggtcaccgtcctagagagcaaatatggaccaccatgccctccatgtcctttttgggtcctggtg<br>gtcgtgggaggcgtgctggcatgttattccctgctggtcactgtggccttcatcatcttctgggtgcg<br>gagcaagcggagccggctgctgcactctgactacatgaacatgactccacggagacccggccct<br>acccggaaacattatcagccctacgccccacccagagattttgccgcttataggtccagggtgaa<br>gtttctcgcagtgcagatgcccctgcttatcagcagggacagaatcagctgtacaacgagctgaa<br>tctgggcaggcgcgaggaatacgacgtgctggataagcgacggggcagagaccccgaaatgg<br>gagggaagcccagaaggaaaaaccctcaggagggctgtataatgaactgcagaaggacaaa<br>atggcagaggcctacagtgaaatcgggatgaagggagagcgccgacggggaaaggccacg<br>atggactgtatcagggcctgtctactgccaccaaggacacctacgatgccctgcacatgcaggct<br>ctgcctccacgctga |
| SEQ ID NO: 14 | atgctgctgctggtgacaagcctgctgctgtgcgaactgccccatcccgccttcctgctgattcctg<br>gtgtacactccgaggtgcagctgttggagtctgggggaggcttggtacagcctggggggtccctg<br>agactctcctgtgcagcctctggattcacctttagcagctatgccatgagctgggtccgccaggctc<br>cagggaaggggctggagtgggtctcagctattagtggtagtggtggtagcacatactacgcagac<br>tccgtgaagggccggttcaccatctccagagacaattccaagaacacgctgtatctgcaaatgaac<br>agcctgagagccgaggacacggccgtgtattactgtgcgagaggaaagcgatactttgactactg<br>gggccaggggacaatggtcaccgtctcgagtggtgggggggcagcggtggtggaggctctg<br>gtggaggagggagctcctatgagctgactcagccaccctcagcgtctgggacccccgggcaga<br>gggtcaccatctcttgttctggaggcagctccaacatcggaagtaatactgtaaactggttccggca<br>gctcccaggaacggcccccaaactcctcgtttattttaataatcagcgaccctcaggggtccctga<br>ccgattctctggctccaagtctggcacctcggcctccctggccatcggtgggctccagtctgacga<br>tgaggctgactattactgtgtagcatgggatgactctctgaatgctccggtgttcggcggagggac<br>caaggtcaccgtcctagagagcaaatatggaccaccatgccctccatgtcctttttgggtcctggtg<br>gtcgtgggaggcgtgctggcatgttattccctgctggtcactgtggccttcatcatcttctgggtgcg<br>gagcaagcggagccggctgctgcactctgactacatgaacatgactccacggagacccggccct<br>acccggaaacattatcagccctacgccccacccagagattttgccgcttataggtccaagcgcgg<br>ccgaaagaaactgctgtacatcttcaaacagcccttcatgagacccgtccagacaactcaggagg<br>aagacggctgcagctgtaggttccccgaggaagaggaagggggatgtgagctgagggtgaagt<br>tttctcgcagtgcagatgcccctgcttatcagcagggacagaatcagctgtacaacgagctgaatc<br>tgggcaggcgcgaggaatacgacgtgctggataagcgacggggcagagaccccgaaatggg<br>agggaagcccagaaggaaaaaccctcaggagggctgtataatgaactgcagaaggacaaaat<br>ggcagaggcctacagtgaaatcgggatgaagggagagcgccgacggggaaaggccacgat<br>ggactgtatcagggcctgtctactgccaccaaggacacctacgatgccctgcacatgcaggctct<br>gcctccacgctga |
| SEQ ID NO: 15 | atgctgctgctggtgacaagcctgctgctgtgcgaactgccccatcccgccttcctgctgattcctg<br>aggtccagctgctggagagcggaggaggactggtgcagcctggaggaagtctgcgactgtcat<br>gcgccgctagcggcttcaccttcagctcctatgcaatgagctgggtgcgacaggcaccaggcaa<br>ggggctggagtgggtctccgctatctccggctctggaggctctacttactatgcagacagtgtgaa<br>ggggcggttcacaatctccagagataactctaagaacactctgtacctgcagatgaactctctgag<br>agctgaggacaccgcagtgtactattgcgccaagggcaaaaggtactttgattattggggacagg<br>gcactatggtgaccgtctctagtggaggaggaggaagcggaggaggaggatccggcggagga<br>ggcagtcagtcagtgctgacacagccacctagcgcctccggaaccccaggacagcgggtcaca<br>atctcttgtagtgggggatcaagcgacattgggagcaacaccgtgaattggtatcagcagctgcct<br>ggaacagctccaaagctgctgatctactataacaatcagaggccctccggcgtccctgatcgcttc<br>tcaggcagcaaatccgggacttctgcaagtctggccattagtggcctgcagtcagaggacgaag<br>ccgattactattgtgctacctgggacgataggatgtactctcccgtgttcggcgggggaacaaagc<br>tgactgtcctggagagcaaatatggaccaccatgccctccatgtcctttttgggtcctggtggtcgtg<br>ggaggcgtgctggcatgttattctctgctggtcacagtggctttcatcatcttctgggtcaagcgagg<br>ccggaagaaactgctgtacatcttcaaacagccttttatgcgcccagtgcagacaactcaggagg<br>aagacggctgctcttgtcggttccccgaggaagaggaagggggatgtgagctgcgcgtgaagtt<br>ttctcgaagtgccgatgctcctgcatatcagcagggacagaaccagctgtacaacgagctgaatct<br>gggccggagagaggaatacgacgtgctggataagaggcgcggcagagacccagaaatgggc<br>gggaagccacgacggaaaaaccccaggagggctgtataatgaactgcagaaggacaaaat<br>ggccgaggcttacagcgaaatcgggatgaagggagagagaaggcgcggaaaaggccacgat<br>ggactgtatcagggcctgagcactgccaccaaggacacctacgatgctctgcacatgcaggcac<br>tgccacccaggtga |
| SEQ ID NO: 16 | atgctgctgctggtgacaagcctgctgctgtgcgaactgccccatcccgccttcctgctgattcctg<br>aggtccagctgctggagagcggaggaggactggtgcagcctggaggaagtctgcgactgtcat<br>gcgccgctagcggcttcaccttcagctcctatgcaatgagctgggtgcgacaggcaccaggcaa<br>ggggctggagtgggtctccgctatctccggctctggaggctctacttactatgcagacagtgtgaa<br>ggggcggttcacaatctccagagataactctaagaacactctgtacctgcagatgaactctctgag<br>agctgaggacaccgcagtgtactattgcgccaagggcaaaaggtactttgattattggggacagg<br>gcactatggtgaccgtctctagtggaggaggaggaagcggaggaggaggatccggcggagga<br>ggcagtcagtcagtgctgacacagccacctagcgcctccggaaccccaggacagcgggtcaca<br>atctcttgtagtgggggatcaagcgacattgggagcaacaccgtgaattggtatcagcagctgcct<br>ggaacagctccaaagctgctgatctactataacaatcagaggccctccggcgtccctgatcgcttc<br>tcaggcagcaaatccgggacttctgcaagtctggccattagtggcctgcagtcagaggacgaag<br>ccgattactattgtgctacctgggacgataggatgtactctcccgtgttcggcgggggaacaaagc<br>tgactgtcctggagagcaaatatggaccaccatgccctccatgtcctttttgggtcctggtggtcgtg<br>ggaggcgtgctggcatgttactccctgctggtcactgtggccttcatcatcttctgggtgcgggtga<br>agttttctcgcagtgccgacgctcccgcatga |

TABLE 6-continued

| Sequences | |
|---|---|
| SEQ ID NO: 17 | atgctgctgctggtgacaagcctgctgctgtgcgaactgccccatcccgccttcctgctgattcctg<br>aggtccagctgctggagagcggaggaggactggtgcagcctggaggaagtctgcgactgtcat<br>gcgccgctagcggcttcaccttcagctcctatgcaatgagctgggtgcgacaggcaccaggcaa<br>ggggctggagtgggtctccgctatctccggctctggaggctctacttactatgcagacagtgtgaa<br>ggggcggttcacaatctccagagataactctaagaacactctgtacctgcagatgaactctctgag<br>agctgaggacaccgcagtgtactattgcgccaagggcaaaaggtactttgattattggggacagg<br>gcactatggtgaccgtctctagtggaggaggaggaagcggaggaggaggatccggcggagga<br>ggcagtcagtcagtgctgacacagccacctagcgcctccggaaccccaggacagcgggtcaca<br>atctcttgtagtgggggatcaagcgacattgggagcaacaccgtgaattggtatcagcagctgcct<br>ggaacagctccaaagctgctgatctactataacaatcagaggccctccggcgtccctgatcgcttc<br>tcaggcagcaaatccgggacttctgcaagtctggccattagtggcctgcagtcagaggacgaag<br>ccgattactattgtgctacctgggacgataggatgtactctcccgtgttcggcggggggaacaaagc<br>tgactgtcctggagagcaaatatggaccaccatgccctccatgtcctttttgggtcctggtggtcgtg<br>ggaggcgtgctggcatgttattccctgctggtcacagtggccttcatcatcttctgggtgcggagca<br>agcggagccggctgctgcactctgactacatgaacatgacccccccggagacccggccctacaa<br>gaaagcattatcagccttacgccccacccagggacttcgcagcttatcgctcccgagtgaaattttc<br>tcgcagtgcagatgcccccgcttatcagcagggccagaatcagctgtacaacgagctgaatctgg<br>ggaggcgcgaggaatacgacgtgctggataagcgacggggccgggaccccgaaatgggagg<br>aaagcctagaaggaaaaacccacaggagggcctgtataatgaactgcagaaggacaaaatggc<br>agaggcctacagcgaaatcggaatgaagggagagcgccgacggggcaaaggacacgatggc<br>ctgtatcaggggctgagcaccgccacaaaggacacctacgatgccctgcacatgcaggctctgc<br>ctccacgctga |
| SEQ ID NO: 18 | atgctgctgctggtgacaagcctgctgctgtgcgaactgccccatcccgccttcctgctgattcctg<br>aggtccagctgctggagagcggaggaggactggtgcagcctggaggaagtctgcgactgtcat<br>gcgccgctagcggcttcaccttcagctcctatgcaatgagctgggtgcgacaggcaccaggcaa<br>ggggctggagtgggtctccgctatctccggctctggaggctctacttactatgcagacagtgtgaa<br>ggggcggttcacaatctccagagataactctaagaacactctgtacctgcagatgaactctctgag<br>agctgaggacaccgcagtgtactattgcgccaagggcaaaaggtactttgattattggggacagg<br>gcactatggtgaccgtctctagtggaggaggaggaagcggaggaggaggatccggcggagga<br>ggcagtcagtcagtgctgacacagccacctagcgcctccggaaccccaggacagcgggtcaca<br>atctcttgtagtgggggatcaagcgacattgggagcaacaccgtgaattggtatcagcagctgcct<br>ggaacagctccaaagctgctgatctactataacaatcagaggccctccggcgtccctgatcgcttc<br>tcaggcagcaaatccgggacttctgcaagtctggccattagtggcctgcagtcagaggacgaag<br>ccgattactattgtgctacctgggacgataggatgtactctcccgtgttcggcggggggaacaaagc<br>tgactgtcctggagagcaaatatggaccaccatgccctccatgtcctttttgggtcctggtggtcgtg<br>ggaggcgtgctggcatgttattccctgctggtcactgtggccttcatcatcttctgggtgcggagca<br>agcggagccggctgctgcactctgactacatgaacatgactccacggagacccggccctacccg<br>gaaacattatcagccctacgccccacccagagattttgccgcttataggtccaagcgcggccgaa<br>agaaactgctgtacatcttcaaacagcccttcatgagacccgtccagacaactcaggaggaagac<br>ggctgcagctgtaggttccccgaggaagaggaaggggggatgtgagctgagggtgaagttttctc<br>gcagtgcagatgcccctgcttatcagcagggacagaatcagctgtacaacgagctgaatctgggc<br>aggcgcgaggaatacgacgtgctggataagcgacggggcagagaccccgaaatgggaggga<br>agcccagaaggaaaaaccctcaggaggggctgtataatgaactgcagaaggacaaaatggcag<br>aggcctacagtgaaatcgggatgaagggagagcgccgacggggaaaaggccacgatggactg<br>tatcagggcctgtctactgccaccaaggacacctacgatgccctgcacatgcaggctctgcctcca<br>cgctga |
| SEQ ID NO: 19 | MLLLVTSLLLCELPHPAFLLIPDVVMTQSPLSLPVTPGEPASIS<br>CRSSQSLVHSNRNTYLHWYLQKPGQSPQLLIYKVSNRFSGVP<br>DRFSGSGSGTDFTLKISRVEAEDVGVYYCSQNTHVPPTFGQGT<br>KLEIKGGGGSGGGGSGGGGSQVQLVQSGAEVKKPGASVKVS<br>CKASGYTFTDYEMHWVRQAPGQGLEWMGALDPKTGDTAYS<br>QKFKGRVTLTADKSTSTAYMELSSLTSEDTAVYYCTRFYSYT<br>YWGQGTLVTVSSDKTHTCPPCPFWVLVVVGGVLACYSLLVT<br>VAFIIFWVKRGRKKLLYIFKQPFMRPVQTTQEEDGCSCRFPEE<br>EEGGCELRVKFSRSADAPAYQQGQNQLYNELNLGRREEYDV<br>LDKRRGRDPEMGGKPQRRKNPQEGLYNELQKDKMAEAYSEI<br>GMKGERRRGKGHDGLYQGLSTATKDTYDALHMQALPPR* |
| SEQ ID NO: 20 | MLLLVTSLLLCELPHPAFLLIPDVVMTQSPLSLPVTPGEPASIS<br>CRSSQSLVHSNRNTYLHWYLQKPGQSPQLLIYKVSNRFSGVP<br>DRFSGSGSGTDFTLKISRVEAEDVGVYYCSQNTHVPPTFGQGT<br>KLEIKGGGGSGGGGSGGGGSQVQLVQSGAEVKKPGASVKVS<br>CKASGYTFTDYEMHWVRQAPGQGLEWMGALDPKTGDTAYS<br>QKFKGRVTLTADKSTSTAYMELSSLTSEDTAVYYCTRFYSYT<br>YWGQGTLVTVSSDKTHTCPPCPFWVLVVVGGVLACYSLLVT<br>VAFIIFWVRSKRSRLLHSDYMNMTPRRPGPTRKHYQPYAPPR<br>DFAAYRSKRGRKKLLYIFKQPFMRPVQTTQEEDGCSCRFPEEE<br>EGGCELRVKFSRSADAPAYQQGQNQLYNELNLGRREEYDVL<br>DKRRGRDPEMGGKPQRRKNPQEGLYNELQKDKMAEAYSEIG<br>MKGERRRGKGHDGLYQGLSTATKDTYDALHMQALPPR* |
| SEQ ID NO: 21 | MLLLVTSLLLCELPHPAFLLIPQVQLVQSGGGVVQPGRSLRLS<br>CAASGFTFSSYGLHWVRQAPGKGLEWVAAISYDGSKKYYAD<br>SVKGRLTISRDNSKNTLYLQMNSLRPDDTALYFCARGWFVEP<br>LSWGQGTLVTVSSGGGGSGGGGSGGGGSQSVLTQPPSASGTP |

TABLE 6-continued

| | Sequences |
|---|---|
| | GQRVTISCSGSSSNIGSNTVNWYQQLPGTAPKLLIYSNNQRPS<br>GVPDRFSGSKSGTSASLAISGLQSEDEADYYCAAWDDSLNGY<br>VFGTGTKLTVLESKYGPPCPPCPFWVLVVVGGVLACYSLLVT<br>VAFIIFWVKRGRKKLLYIFKQPFMRPVQTTQEEDGCSCRFPEE<br>EEGGCELRVKFSRSADAPAYQQGQNQLYNELNLGRREEYDV<br>LDKRRGRDPEMGGKPRRKNPQEGLYNELQKDKMAEAYSEIG<br>MKGERRRGKGHDGLYQGLSTATKDTYDALHMQALPPR* |
| SEQ ID NO: 22 | atgctgctgctggtgacaagcctgctgctgtgcgaactgccccatcccgccttcctgctgattcctg<br>atgtcgtgatgacgcagagccctctctctcttcccgttacccctggtgaacccgcatcaataagttg<br>ccgctccagtcaatcacttgtacattcaaatcgcaatacctacctgcactggtatttgcagaagccg<br>ggacaatcccctcaattgttgatatataaggtatccaatcgcttttctggagttcctgatagattcagc<br>ggatccgggtctggtactgatttcactctgaaaatatccagggtcgaagctgaggacgtaggcgta<br>tattattgctctcagaacacgcatgtcccgccgactttcggccagggcactaaacttgagatcaagg<br>gtgggggggcagcggtggtggaggctctggtggaggagggagccaggtccaactcgttcaa<br>agtggcgcagaggtcaaaaagccaggcgcgagcgttaaagtatcatgtaaggccagcggttata<br>ctttcactgattatgaaatgcactgggtgcgacaagcccccgggcaaggtcttgagtggatgggtg<br>cacttgatccaaaaactggggatactgcctatagccagaaattcaaagggcgcgtcacactcactg<br>ccgacaaaagtacgagcacagcttatatggaattgagttcactgacgagcgaggatacggcagtt<br>tattactgtacgcgcttctactcttacacttattgggggcaaggcactttggttactgtgtcctctgaca<br>agacccatacgtgtccaccgtgtcccttctgggtattggttgtggtcggcggtgtccttgcttgttaca<br>gccttctcgtgacagtcgcattcataatttttgggtgaaaagaggtcggaaaaagttgctgtatatttt<br>caaacaaccctttatgagacctgtacaaacgactcaggaagaggatggttgtagttgcaggtttcc<br>ggaggaggaggaaggtgggtgcgaactgcgggtgaaatttagtagaagcgctgacgcaccag<br>cttaccaacaaggacagaaccaattgtacaacgagcttaacttgggtaggagggaggaatatgat<br>gtactggacaaaaggcgaggtcgcgatccggaaatgggaggcaagccacagcgccggaaaaa<br>cccgcaggaaggcttgtacaacgaacttcagaaagataaaatggcagaagcatactccgaaata<br>gggatgaaaggtgaacggcggcgaggcaagggccacgacggtctgtaccaagggttgtcaac<br>ggcaactaaagacacgtatgatgcacttcatatgcaagctctgccacccaggtga |
| SEQ ID NO: 23 | atgctgctgctggtgacaagcctgctgctgtgcgaactgccccatcccgccttcctgctgattcctg<br>atgtcgtgatgacgcagagccctctctctcttcccgttacccctggtgaacccgcatcaataagttg<br>ccgctccagtcaatcacttgtacattcaaatcgcaatacctacctgcactggtatttgcagaagccg<br>ggacaatcccctcaattgttgatatataaggtatccaatcgcttttctggagttcctgatagattcagc<br>ggatccgggtctggtactgatttcactctgaaaatatccagggtcgaagctgaggacgtaggcgta<br>tattattgctctcagaacacgcatgtcccgccgactttcggccagggcactaaacttgagatcaagg<br>gtgggggggcagcggtggtggaggctctggtggaggagggagccaggtccaactcgttcaa<br>agtggcgcagaggtcaaaaagccaggcgcgagcgttaaagtatcatgtaaggccagcggttata<br>ctttcactgattatgaaatgcactgggtgcgacaagcccccgggcaaggtcttgagtggatgggtg<br>cacttgatccaaaaactggggatactgcctatagccagaaattcaaagggcgcgtcacactcactg<br>ccgacaaaagtacgagcacagcttatatggaattgagttcactgacgagcgaggatacggcagtt<br>tattactgtacgcgcttctactcttacacttattgggggcaaggcactttggttactgtgtcctctgaca<br>agacccatacgtgtccaccgtgtcccttctgggtattggttgtggtcggcggtgtccttgcttgttaca<br>gccttctcgtgacagtcgcattcataatttttgggtgcggagcaagcggagccggctgctgcactc<br>tgactacatgaacatgactccacggagacccggccctacccggaaacattatcagccctacgccc<br>cacccagagattttgccgcttataggtccaaaagaggtcggaaaaagttgctgtatattttcaaaca<br>accctttatgagacctgtacaaacgactcaggaagaggatggttgtagttgcaggtttccggagga<br>ggaggaaggtgggtgcgaactgcgggtgaaatttagtagaagcgctgacgcaccagcttaccaa<br>caaggacagaaccaattgtacaacgagcttaacttgggtaggagggaggaatatgatgtactgga<br>caaaaggcgaggtcgcgatccggaaatgggaggcaagccacagcgccggaaaaacccgcag<br>gaaggcttgtacaacgaacttcagaaagataaaatggcagaagcatactccgaaatagggatgaa<br>aggtgaacggcggcgaggcaagggccacgacggtctgtaccaagggttgtcaacggcaactaa<br>agacacgtatgatgcacttcatatgcaagctctgccacccaggtga |
| SEQ ID NO: 24 | atgctgctgctggtgacaagcctgctgctgtgcgaactgccccatcccgccttcctgctgattcctc<br>aggtccagcttgtgcaaagcggaggaggagtggtacagcctggccgctctttgagactgtcttgt<br>gcggccagtggatttacattctcttcttatgggttgcattgggtcagacaagcaccgggcaaaggat<br>tggaatgggtcgcggccattagctatgatggctcaaagaaatattatgccgattccgtaaaaggga<br>ggttgacaataagccgggataacagcaagaacactttgtatcttcagatgaatagcctccgaccgg<br>acgacacggcactgtatttttgcgcacgcgggtggtttgtagaacccctgagttggggacaaggta<br>ctcttgtcacggtatcttctggcggaggtgggagtggtgggggtggcagtggcgggggtgggtc<br>acaaagcgtgcttacacaacctccttctgcgagcggaactccgggacaacgggttacgatttcatg<br>ctccggctcaagtagcaatataggatcaaatacagtgaattggtatcaacaactccctggcacagc<br>gcccaagctgctgatctactctaataaccagaggccgagtggtgtgccagataggttcagtggctc<br>taaatcaggtactagcgcgagcctcgccatttcaggacttcaatcagaggatgaagcggactacta<br>ctgtgccgcgtgggatgattcacttaatggatatgttttcgggaccggaacaaaattgacggtattg<br>gagagcaaatatggaccaccatgccctccatgtcctttttgggtcctggtggtcgtgggaggcgtg<br>ctggcatgttattctctgctggtcacagtggctttcatcatcttctgggtcaagcgaggccggaagaa<br>actgctgtacatcttcaaacagccttttatgcgcccagtgcagacaactcaggaggaagacggctg<br>ctcttgtcggttccccgaggaagaggaaggggggatgtgagctgcgcgtgaagttttctcgaagtg<br>ccgatgctcctgcatatcagcagggacagaaccagctgtacaacgagctgaatctgggccggag<br>agaggaatacgacgtgctggataagaggcgcggcagagacccagaaatgggcgggaagcca<br>cgacggaaaaaccccccaggagggcctgtataatgaactgcagaaggacaaaatggccgaggct<br>tacagcgaaatcgggatgaagggagagagaaggcgcggaaaaggccacgatggactgtatca<br>gggcctgagcactgccaccaaggacacctacgatgctctgcacatgcaggcactgccacccag<br>gTGA |

TABLE 6-continued

| Sequences | |
|---|---|
| SEQ ID NO: 25 | MLLLVTSLLLCELPHPAFLLIPEVQLLESGGGLVQPGGSLRLSC AASGFTFSSYAMSWVRQAPGKGLEWVSAISGSGGSTYYADS VKGRFTISRDNSKNTLYLQMNSLRAEDTAVYYCARGKRYFD YWGQGTMVTVSSGGGGSGGGGSGGGGSSYELTQPPSASGTP GQRVTISCSGGSSNIGSNTVNWFRQLPGTAPKLLVYFNNQRPS GVPDRFSGSKSGTSASLAIGGLQSDDEADYYCVAWDDSLNAP VFGGGTKVTVLESKYGPPCPPCPFWVLVVVGGVLACYSLLVT VAFIIFWVKRGRKKLLYIFKQPFMRPVQTTQEEDGCSCRFPEE EEGGCELRVKFSRSADAPAYQQGQNQLYNELNLGRREEYDV LDKRRGRDPEMGGKPRRKNPQEGLYNELQKDKMAEAYSEIG MKGERRRGKGHDGLYQGLSTATKDTYDALHMQALPPR |
| SEQ ID NO: 26 | ATGCTGCTGCTGGTGACAAGCCTGCTGCTGTGCGAACTGCC CCATCCCGCCTTCCTGCTGATTCCTGAGGTGCAGCTGTTGG AGTCTGGGGGAGGCTTGGTACAGCCTGGGGGGTCCCTGAG ACTCTCCTGTGCAGCCTCTGGATTCACCTTTAGCAGCTATG CCATGAGCTGGGTCCGCCAGGCTCCAGGGAAGGGGCTGGA GTGGGTCTCAGCTATTAGTGGTAGTGGTGGTAGCACATACT ACGCAGACTCCGTGAAGGGCCGGTTCACCATCTCCAGAGA CAATTCCAAGAACACGCTGTATCTGCAAATGAACAGCCTG AGAGCCGAGGACACGGCCGTGTATTACTGTGCGAGAGGAA AGCGATACTTTGACTACTGGGGCCAGGGGACAATGGTCAC CGTCTCGAGTGGTGGGGGGGGCAGCGGTGGTGGAGGCTCT GGTGGAGGAGGGAGCTCCTATGAGCTGACTCAGCCACCCT CAGCGTCTGGGACCCCCGGGCAGAGGGTCACCATCTCTTGT TCTGGAGGCAGCTCCAACATCGGAAGTAATACTGTAAACT GGTTCCGGCAGCTCCCAGGAACGGCCCCCAAACTCCTCGTT TATTTTAATAATCAGCGACCCTCAGGGGTCCCTGACCGATT CTCTGGCTCCAAGTCTGGCACCTCGGCCTCCCTGGCCATCG GTGGGCTCCAGTCTGACGATGAGGCTGACTATTACTGTGTA GCATGGGATGACTCTCTGAATGCTCCGGTGTTCGGCGGAG GGACCAAGGTCACCGTCCTAGAGAGCAAATATGGACCACC ATGCCCTCCATGTCCTTTTTGGGTCCTGGTGGTCGTGGGAG GCGTGCTGGCATGTTATTCTCTGCTGGTCACAGTGGCTTTC ATCATCTTCTGGGTCAAGCGAGGCCGGAAGAAACTGCTGT ACATCTTCAAACAGCCTTTTATGCGCCCAGTGCAGACAACT CAGGAGGAAGACGGCTGCTCTTGTCGGTTCCCCGAGGAAG AGGAAGGGGGATGTGAGCTGCGCGTGAAGTTTTCTCGAAG TGCCGATGCTCCTGCATATCAGCAGGGACAGAACCAGCTG TACAACGAGCTGAATCTGGGCCGGAGAGAGGAATACGACG TGCTGGATAAGAGGCGCGGCAGAGACCCAGAAATGGGCG GGAAGCCACGACGGAAAAACCCCCAGGAGGGGCTGTATA ATGAACTGCAGAAGGACAAAATGGCCGAGGCTTACAGCGA AATCGGGATGAAGGGAGAGAGAAGGCGCGGAAAAGGCCA CGATGGACTGTATCAGGGCCTGAGCACTGCCACCAAGGAC ACCTACGATGCTCTGCACATGCAGGCACTGCCACCCAGG |
| SEQ ID NO: 27 | EVQLLESGGGLVQPGGSLRLSCAASGFTFSSYAMSWVRQAPG KGLEWVSAISGSGGSTYYADSVKGRFTISRDNSKNTLYLQMN SLRAEDTAVYYCARGKRYFDYWGQGTMVTVSS |
| SEQ ID NO: 28 | SYELTQPPSASGTPGQRVTISCSGGSSNIGSNTVNWFRQLPGT APKLLVYFNNQRPSGVPDRFSGSKSGTSASLAIGGLQSDDEAD YYCVAWDDSLNAPVFGGGTKVTVL |
| SEQ ID NO: 29 | EVQLLESGGGLVQPGGSLRLSCAASGFTFSSYAMSWVRQAPG KGLEWVSAISGSGGSTYYADSVKGRFTISRDNSKNTLYLQMN SLRAEDTAVYYCAKGKRYFDYWGQGTMVTVSS |
| SEQ ID NO: 30 | QSVLTQPPSASGTPGQRVTISCSGGSSDIGSNTVNWYQQLPGT APKLLIYYNNQRPSGVPDRFSGSKSGTSASLAISGLQSEDEAD YYCATWDDRMYSPVFGGGTKLTVL |
| SEQ ID NO: 31 | DVVMTQSPLSLPVTPGEPASISCRSSQSLVHSNRNTYLHWYLQ KPGQSPQLLIYKVSNRFSGVPDRFSGSGSGTDFTLKISRVEAED VGVYYCSQNTHVPPTFGQGTKLEIKGGGGSGGGGSGGGGSQ VQLVQSGAEVKKPGASVKVSCKASGYTFTDYEMHWVRQAP GQGLEWMGALDPKTGDTAYSQKFKGRVTLTADKSTSTAYM ELSSLTSEDTAVYYCTRFYSYTYWGQGTLVTVSS |
| SEQ ID NO: 32 | QVQLVQSGGGVVQPGRSLRLSCAASGFTFSSYGLHWVRQAP GKGLEWVAAISYDGSKKYYADSVKGRLTISRDNSKNTLYLQ MNSLRPDDTALYFCARGWFVEPLSWGQGTLVTVSSGGGGSG GGGSGGGGSQSVLTQPPSASGTPGQRVTISCSGSSSNIGSNTV NWYQQLPGTAPKLLIYSNNQRPSGVPDRFSGSKSGTSASLAIS GLQSEDEADYYCAAWDDSLNGYVFGTGTKLTVL |

TABLE 6-continued

| | Sequences |
|---|---|
| SEQ ID NO: 33 | gaggtgcagctgttggagtctgggggaggcttggtacagcctggggggtccctgagactctcctg<br>tgcagcctctggattcacctttagcagctatgccatgagctgggtccgccaggctccagggaagg<br>ggctggagtgggtctcagctattagtggtagtggtggtagcacatactacgcagactccgtgaag<br>ggccggttcaccatctccagagacaattccaagaacacgctgtatctgcaaatgaacagcctgag<br>agccgaggacacggccgtgtattactgtgcgagaggaaagcgatactttgactactggggccag<br>gggacaatggtcaccgtctcgagtggtgggggggcagcggtggtggaggctctggtggagg<br>agggagctcctatgagctgactcagccaccctcagcgtctgggacccccgggcagagggtcac<br>catctcttgttctggaggcagctccaacatcggaagtaatactgtaaactggttccggcagctccca<br>ggaacggcccccaaactcctcgtttattttaataatcagcgaccctcaggggtccctgaccgattct<br>ctggctccaagtctggcacctcggcctccctggccatcggtgggctccagtctgacgatgaggct<br>gactattactgtgtagcatgggatgactctctgaatgctccggtgttcggcggagggaccaaggtc<br>accgtccta |
| SEQ ID NO: 34 | gaggtccagctgctggagagcggaggaggactggtgcagcctggaggaagtctgcgactgtca<br>tgcgccgctagcggcttcaccttcagctcctatgcaatgagctgggtgcgacaggcaccaggcaa<br>ggggctggagtgggtctccgctatctccggctctggaggctctacttactatgcagacagtgtgaa<br>ggggcggttcacaatctccagagataactctaagaacactctgtacctgcagatgaactctctgag<br>agctgaggacaccgcagtgtactattgcgccaagggcaaaaggtactttgattattggggacagg<br>gcactatggtgaccgtctctagtggaggaggaggaagcggaggaggaggatccggcggagga<br>ggcagtcagtcagtgctgacacagccacctagcgcctccggaaccccaggacagcgggtcaca<br>atctcttgtagtggggggatcaagcgacattgggagcaacaccgtgaattggtatcagcagctgcct<br>ggaacagctccaaagctgctgatctactataacaatcagaggccctccggcgtccctgatcgcttc<br>tcaggcagcaaatccgggacttctgcaagtctggccattagtggcctgcagtcagaggacgaag<br>ccgattactattgtgctacctgggacgataggatgtactctcccgtgttcggcggggggaacaaagc<br>tgactgtcctg |
| SEQ ID NO: 35 | gatgtcgtgatgacgcagagccctctctctcttcccgttacccctggtgaacccgcatcaataagtt<br>gccgctccagtcaatcacttgtacattcaaatcgcaatacctacctgcactggtatttgcagaagcc<br>gggacaatcccctcaattgttgatatataaggtatccaatcgcttttctggagttcctgatagattcag<br>cggatccgggtctggtactgatttcactctgaaaatatccagggtcgaagctgaggacgtaggcgt<br>atattattgctctcagaacacgcatgtcccgccgactttcggccagggcactaaacttgagatcaag<br>ggtgggggggcagcggtggtggaggctctggtggaggagggagccaggtccaactcgttca<br>aagtggcgcagaggtcaaaaagccaggcgcgagcgttaaagtatcatgtaaggccagcggttat<br>actttcactgattatgaaatgcactgggtgcgacaagcccccgggcaaggtcttgagtggatgggt<br>gcacttgatccaaaaactggggatactgcctatagccagaaattcaaagggcgcgtcacactcact<br>gccgacaaaagtacgagcacagcttatatggaattgagttcactgacgagcgaggatacggcagt<br>ttattactgtacgcgcttctactcttacacttattgggggcaaggcactttggttactgtgtcctct |
| SEQ ID NO: 36 | caggtccagcttgtgcaaagcggaggaggagtggtacagcctggccgctctttgagactgtcttgt<br>gcggccagtggatttacattctcttcttatgggttgcattgggtcagacaagcaccgggcaaaggat<br>tggaatgggtcgcggccattagctatgatggctcaaagaaatattatgccgattccgtaaaggga<br>ggttgacaataagccgggataacagcaagaacactttgtatcttcagatgaatagcctccgaccgg<br>acgacacggcactgtatttttgcgcacgcgggtggtttgtagaacccctgagttggggacaaggta<br>ctcttgtcacggtatcttctggcggaggtgggagtggtgggggtggcagtggcgggggtgggtc<br>acaaagcgtgcttacacaacctccttctgcgagcggaactccgggacaacgggttacgatttcatg<br>ctccggctcaagtagcaatataggatcaaatacagtgaattggtatcaacaactccctggcacagc<br>gcccaagctgctgatctactctaataaccagaggccgagtggtgtgccagataggttcagtggctc<br>taaatcaggtactagcgcgagcctcgccatttcaggacttcaatcagaggatgaagcggactacta<br>ctgtgccgcgtgggatgattcacttaatggatatgttttcgggaccggaacaaaattgacggtattg |
| SEQ ID NO: 37 | GFTFS**SYAMS** |
| SEQ ID NO: 38 | AISGSGGSTYYADSVKG |
| SEQ ID NO: 39 | GKRYFDY |
| SEQ ID NO: 40 | SGGSSNIGSNTVN |
| SEQ ID NO: 41 | FNNQRPS |
| SEQ ID NO: 42 | VAWDDSLNAPV |
| SEQ ID NO: 43 | SGGSSDIGSNTVN |
| SEQ ID NO: 44 | YNNQRPS |
| SEQ ID NO: 45 | ATWDDRMYSPV |
| SEQ ID NO: 46 | ATGCTGCTGCTGGTGACAAGCCTGCTGCTGTGCGAACTGCC<br>CCATCCCGCCTTCCTGCTGATTCCTGAGGTGCAGCTGTTGG<br>AGTCTGGGGGAGGCTTGGTACAGCCTGGGGGGTCCCTGAG<br>ACTCTCCTGTGCAGCCTCTGGATTCACCTTTAGCAGCTATG<br>CCATGAGCTGGGTCCGCCAGGCTCCAGGGAAGGGGCTGGA<br>GTGGGTCTCAGCTATTAGTGGTAGTGGTGGTAGCACATACT<br>ACGCAGACTCCGTGAAGGGCCGGTTCACCATCTCCAGAGA<br>CAATTCCAAGAACACGCTGTATCTGCAAATGAACAGCCTG<br>AGAGCCGAGGACACGGCCGTGTATTACTGTGCGAGAGGAA<br>AGCGATACTTTGACTACTGGGGCCAGGGGACAATGGTCAC |

TABLE 6-continued

| | Sequences |
|---|---|
| | CGTCTCGAGTGGTGGGGGGGGCAGCGGTGGTGGAGGCTCT<br>GGTGGAGGAGGGAGCTCCTATGAGCTGACTCAGCCACCCT<br>CAGCGTCTGGGACCCCCGGGCAGAGGGTCACCATCTCTTGT<br>TCTGGAGGCAGCTCCAACATCGGAAGTAATACTGTAAACT<br>GGTTCCGGCAGCTCCCAGGAACGGCCCCCAAACTCCTCGTT<br>TATTTTAATAATCAGCGACCCTCAGGGGTCCCTGACCGATT<br>CTCTGGCTCCAAGTCTGGCACCTCGGCCTCCCTGGCCATCG<br>GTGGGCTCCAGTCTGACGATGAGGCTGACTATTACTGTGTA<br>GCATGGGATGACTCTCTGAATGCTCCGGTGTTCGGCGGAG<br>GGACCAAGGTCACCGTCCTAGAGAGCAAATATGGACCACC<br>ATGCCCTCCATGTCCTTTTTGGGTCCTGGTGGTCGTGGGAG<br>GCGTGCTGGCATGTTATTCTCTGCTGGTCACAGTGGCTTTC<br>ATCATCTTCTGGGTCAAGCGAGGCCGGAAGAAACTGCTGT<br>ACATCTTCAAACAGCCTTTTATGCGCCCAGTGCAGACAACT<br>CAGGAGGAAGACGGCTGCTCTTGTCGGTTCCCCGAGGAAG<br>AGGAAGGGGGATGTGAGCTGCGCGTGAAGTTTTCTCGAAG<br>TGCCGATGCTCCTGCATATCAGCAGGGACAGAACCAGCTG<br>TACAACGAGCTGAATCTGGGCCGGAGAGAGGAATACGACG<br>TGCTGGATAAGAGGCGCGGCAGAGACCCAGAAATGGGCG<br>GGAAGCCACGACGGAAAAACCCCCAGGAGGGGCTGTATA<br>ATGAACTGCAGAAGGACAAAATGGCCGAGGCTTACAGCGA<br>AATCGGGATGAAGGGAGAGAGAAGGCGCGGAAAAGGCCA<br>CGATGGACTGTATCAGGGCCTGAGCACTGCCACCAAGGAC<br>ACCTACGATGCTCTGCACATGCAGGCACTGCCACCCAGGG<br>GTAGCGGCGAGGGCAGAGGAAGTCTTCTAACATGCGGTGA<br>CGTGGAGGAGAATCCCGGCCCTATGGGTCGGGGGCTGCTC<br>AGGGGCCTGTGGCCGCTGCACATCGTCCTGTGGACGCGTAT<br>CGCCAGCACGATCCCACCGCACGTTCAGAAGTCGGTTAAT<br>AACGACATGATAGTCACTGACAACAACGGTGCAGTCAAGT<br>TTCCACAACTGTGTAAATTTTGTGATGTGAGATTTTCCACC<br>TGTGACAACCAGAAATCCTGCATGAGCAACTGCAGCATCA<br>CCTCCATCTGTGAGAAGCCACAGGAAGTCTGTGTGGCTGTA<br>TGGAGAAAGAATGACGAGAACATAACACTAGAGACAGTTT<br>GCCATGACCCCAAGCTCCCCTACCATGACTTTATTCTGGAA<br>GATGCTGCTTCTCCAAAGTGCATTATGAAGGAAAAAAAAA<br>AGCCTGGTGAGACTTTCTTCATGTGTTCCTGTAGCTCTGAT<br>GAGTGCAATGACAACATCATCTTCTCAGAAGAATATAACA<br>CCAGCAATCCTGACTTGTTGCTAGTCATATTTCAAGTGACA<br>GGCATCAGCCTCCTGCCACCACTGGGAGTTGCCATATCTGT<br>CATCATCATCTTCTACTGCTACCGCGTTAACCGGCAG |
| SEQ ID NO: 47 | MLLLVTSLLLCELPHPAFLLIPEVQLLESGGGLVQPGGSLRLSC<br>AASGFTFSSYAMSWVRQAPGKGLEWVSAISGSGGSTYYADS<br>VKGRFTISRDNSKNTLYLQMNSLRAEDTAVYYCARGKRYFD<br>YWGQGTMVTVSSGGGGSGGGGSGGGGSSYELTQPPSASGTP<br>GQRVTISCSGGSSNIGSNTVNWFRQLPGTAPKLLVYFNNQRPS<br>GVPDRFSGSKSGTSASLAIGGLQSDDEADYYCVAWDDSLNAP<br>VFGGGTKVTVLESKYGPPCPPCPFWVLVVVGGVLACYSLLVT<br>VAFIIFWVKRGRKKLLYIFKQPFMRPVQTTQEEDGCSCRFPEE<br>EEGGCELRVKFSRSADAPAYQQGQNQLYNELNLGRREEYDV<br>LDKRRGRDPEMGGKPRRKNPQEGLYNELQKDKMAEAYSEIG<br>MKGERRRGKGHDGLYQGLSTATKDTYDALHMQALPPRGSG<br>EGRGSLLTCGDVEENPGPMGRGLLRGLWPLHIVLWTRIASTIP<br>PHVQKSVNNDMIVTDNNGAVKFPQLCKFCDVRFSTCDNQKS<br>CMSNCSITSICEKPQEVCVAVWRKNDENITLETVCHDPKLPYH<br>DFILEDAASPKCIMKEKKKPGETFFMCSCSSDECNDNIIFSEEY<br>NTSNPDLLLVIFQVTGISLLPPLGVAISVIIIFYCYRVNRQ |

What is claimed is:

1. An isolated nucleic acid sequence encoding
   a) a chimeric antigen receptor (CAR), wherein the CAR comprises an antigen-binding domain specific for a cell surface antigen; and
   b) an armoring molecule, wherein the armoring molecule comprises a TGF-β receptor type 2 dominant-negative (TGFβRIIDN), wherein the TGFβRIIDN comprises a wild-type TGF-β receptor type 2 truncated at residue 194, and wherein the antigen-binding domain is a single chain variable fragment (scFv) comprising the nucleic acid sequence of SEQ ID NO: 33.

2. The isolated nucleic acid sequence according to claim 1, further comprising a transmembrane domain, a costimulatory domain, and a signal domain.

3. The isolated nucleic acid sequence of claim 2, wherein the transmembrane domain comprises a CD28 transmembrane domain.

4. The isolated nucleic acid sequence of claim 2, wherein the costimulatory domain comprises one or more of CD28, 4-1BB, CD3zeta, OX-40, ICOS, CD27, GITR, and MyD88/CD40 costimulatory domains.

5. The isolated nucleic acid sequence of claim 2, wherein the costimulatory domain comprises one or more of CD28, 4-1BB, and CD3zeta costimulatory domains.

6. The isolated nucleic acid sequence of claim 2, wherein the signal domain comprises a sequence encoding a CSFR2 signal peptide.

7. The isolated nucleic acid sequence according to claim 5, further comprising a hinge/spacer domain.

8. The isolated nucleic acid sequence of claim 7, wherein the hinge/spacer domain is an IgG4P hinge/spacer.

9. The isolated nucleic acid sequence of claim 1, wherein the TGF-β receptor type 2 dominant-negative (TGFβRIIDN) counters immunosuppression of a cell in a tumor microenvironment when expressed on a surface of the cell.

10. The isolated nucleic acid sequence of claim 1, encoded by the nucleic acid sequence of SEQ ID NO: 46.

11. The isolated nucleic acid of claim 1, wherein the cell surface antigen comprises GPC3.

12. A vector, comprising a nucleic acid sequence encoding a chimeric antigen receptor (CAR), wherein the CAR comprises an antigen-binding domain specific for a cell surface antigen and an armoring molecule, wherein the nucleic acid sequence comprises SEQ ID NO: 46.

13. A cell comprising the vector of claim 12.

14. A cell, comprising:

a nucleic acid sequence encoding a chimeric antigen receptor (CAR), and a TGFβRIIDN armoring molecule expressed on a surface of the cell, wherein the TGFβRIIDN comprises a wild-type TGF-β receptor type 2 truncated at residue 194, wherein the CAR comprises an antigen-binding domain, a transmembrane domain, a costimulatory domain, and a signal domain, and wherein the antigen-binding domain is a single chain variable fragment (scFv) comprising the nucleic acid sequence of SEQ ID NO: 33.

15. A cell, comprising:

an anti-GPC3 chimeric antigen receptor (CAR) comprising an antigen binding domain, wherein the antigen binding domain comprises an antibody, Fab, or an scFv comprising a heavy chain variable region (VH) and a light chain variable region (VL), wherein the VH comprises a CDR1 comprising the amino acid sequence of SEQ ID NO: 37, a CDR2 comprising the amino acid sequence of SEQ ID NO: 38, and a CDR3 comprising the amino acid sequence of SEQ ID NO: 39, and wherein the VL comprises a CDR1 comprising the amino acid sequence of SEQ ID NO: 40 or SEQ ID NO: 43, a CDR2 comprising the amino acid sequence of SEQ ID NO: 41 or SEQ ID NO: 44, and a CDR3 comprising the amino acid sequence of SEQ ID NO: 42 or SEQ ID NO: 45; and a TGFβRIIDN armoring molecule comprising amino acids 478 to 671 of SEQ ID NO: 47.

16. The cell of claim 15, wherein the VH comprises the amino acid sequence of SEQ ID NO: 27 or SEQ ID NO: 29.

17. The cell of claim 15, wherein the VL comprises the amino acid sequence of SEQ ID NO: 28 or SEQ ID NO: 30.

18. The cell of claim 15, wherein the anti-GPC3 chimeric antigen receptor (CAR) and TGFβRIIDN armoring molecules comprise the amino acid sequence of SEQ ID NO: 47.

19. The cell of claim 13, wherein the cell is selected from the group consisting of a T cell, a Natural Killer (NK) cell, a cytotoxic T lymphocyte (CTL), and a regulatory T cell.

20. A cell, comprising:

an anti-GPC3 chimeric antigen receptor (CAR) comprising an antigen binding domain, wherein the antigen binding domain comprises a scFv comprising a heavy chain variable region (VH) and a light chain variable region (VL), wherein the VH comprises a CDR1 comprising the amino acid sequence of SEQ ID NO: 37, a CDR2 comprising the amino acid sequence of SEQ ID NO: 38, and a CDR3 comprising the amino acid sequence of SEQ ID NO: 39, and wherein the VL comprises a CDR1 comprising the amino acid sequence of SEQ ID NO: 40, a CDR2 comprising the amino acid sequence of SEQ ID NO: 41, and a CDR3 comprising the amino acid sequence of SEQ ID NO: 42; and a TGFβRIIDN armoring molecule expressed on the surface of the cell comprising amino acids 478 to 671 of SEQ ID NO: 47.

21. The cell of claim 20, wherein the VH comprises the amino acid sequence of SEQ ID NO: 27 and the VL comprises the amino acid sequence of SEQ ID NO: 28.

22. The cell of claim 20, wherein the scFv comprises the amino acid sequence of SEQ ID NO: 1.

23. The cell of claim 20, wherein the CAR comprises the amino acid sequence of SEQ ID NO: 25.

24. The cell of claim 20, wherein the CAR and TGFBRI-IDN armoring molecule comprise the amino acid sequence of SEQ ID NO: 47.

* * * * *